United States Patent
Katti et al.

(10) Patent No.: US 11,547,720 B2
(45) Date of Patent: Jan. 10, 2023

(54) AYURVEDIC ENCAPSULATED GOLD NANOPARTICLES, FABRICATION METHODS AND CANCER THERAPEUTIC METHODS

(71) Applicant: The Curators of the University of Missouri, Columbia, MO (US)

(72) Inventors: Kattesh Katti, Columbia, MO (US); Menka Khoobchandani, Columbia, MO (US); Kavita Katti, Columbia, MO (US); Alsam Khan, Columbia, MO (US); Chintamani Joshi, Columbia, MO (US); Vinay Mutalik, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 436 days.

(21) Appl. No.: 16/479,767

(22) PCT Filed: Feb. 8, 2018

(86) PCT No.: PCT/US2018/017421
§ 371 (c)(1),
(2) Date: Jul. 22, 2019

(87) PCT Pub. No.: WO2018/152002
PCT Pub. Date: Aug. 23, 2018

(65) Prior Publication Data
US 2021/0008103 A1    Jan. 14, 2021

Related U.S. Application Data

(60) Provisional application No. 62/459,388, filed on Feb. 15, 2017.

(51) Int. Cl.
*A61K 33/242* (2019.01)
*A61K 9/48* (2006.01)
(Continued)

(52) U.S. Cl.
CPC .......... *A61K 33/242* (2019.01); *A61K 9/4866* (2013.01); *A61K 9/4875* (2013.01);
(Continued)

(58) Field of Classification Search
CPC .................................................. A61K 33/242
See application file for complete search history.

(56) References Cited

U.S. PATENT DOCUMENTS 8,211,205 B1    7/2012  Didenko et al.
8,569,063 B1    10/2013 Sahi et al.
(Continued)

FOREIGN PATENT DOCUMENTS

CA    2660507      12/2017
CN    104070179    10/2014
(Continued)

OTHER PUBLICATIONS

Shah et al., "*Mangifera indica* (Mango)", Pharmacognosy Review, 2010, pp. 1-14, vol. 4, No. 7, Pharmacognosy Reviews.
(Continued)

*Primary Examiner* — Benjamin J Packard
(74) *Attorney, Agent, or Firm* — Greer, Burns & Crain, Ltd.; Steven P. Fallon

(57) ABSTRACT

Ayurvedic encapsulated gold nanoparticles, methods of fabrication and methods of treatment are provided. A method of fabrication includes mixing dried gooseberry product or mango peel product or phytochemical existent therein, into a liquid medium to form a reducing agent solution. Gold salts are mixed into the reducing agent solution. Reaction of the gold salts proceeds, in the absence of any other reducing agent, to form a nanoparticle solution of stabilized, biocompatible Ayurvedic encapsulated gold nanoparticles. An Ayurvedic medicine consists of a non-radioactive gold nanoparticle encapsulated with phytochemical existent in
(Continued)

mango peal or gooseberry in a capsule with curcumin extract and gum Arabic.

15 Claims, 49 Drawing Sheets

(51) Int. Cl.
    *A61K 31/12* (2006.01)
    *A61K 31/7048* (2006.01)
    *A61K 36/185* (2006.01)
    *A61K 36/22* (2006.01)

(52) U.S. Cl.
    CPC .......... *A61K 31/12* (2013.01); *A61K 31/7048* (2013.01); *A61K 36/185* (2013.01); *A61K 36/22* (2013.01)

(56) References Cited

U.S. PATENT DOCUMENTS

| | | |
|---|---|---|
| 2007/0051202 A1 | 3/2007 | Raghuraman et al. |
| 2009/0074674 A1 | 3/2009 | Katti et al. |
| 2013/0129618 A1* | 5/2013 | Katti .................. A61K 31/353 424/1.29 |

FOREIGN PATENT DOCUMENTS

| | | |
|---|---|---|
| WO | 2013141722 | 9/2013 |
| WO | 2016046845 | 3/2016 |

OTHER PUBLICATIONS

Philip, "Rapid green synthesis of spherical gold nanoparticles using Mangifera indica leaf", Spectrochimica Acta Part A: Molecular and Biomolecular Spectroscopy, 2010, pp. 807-810, vol. 77, Elsevier B.V.

Joshi et al., "Early Human Safety Study of Turmeric Oil (*Curcuma longa* Oil) Administered Orally in Healthy Volunteers", Journal of the Association of Physicians of India, Nov. 2003, pp. 1055-1060, vol. 51.

Nair et al., "Delivery of anti-inflammatory nutraceuticals by nanoparticles for the prevention and treatment of cancer", Biochemical Pharmacology, Dec. 15, 2010, pp. 1-26, vol. 80, No. 12, Elsevier Inc.

International Search Report and Written Opinion from the corresponding International Patent Application No. PCT/US2017/054945, dated Nov. 12, 2017.

International Search Report and Written Opinion from the corresponding International Patent Application No. PCT/US2018/017421, dated Apr. 2, 2018.

Indian Office Action from the corresponding Indian Patent Application No. 201947017150, dated Feb. 26, 2020.

Gold-Smith et al., "Magniferin and Cancer: Mechanisms of Action", Nutrients, 2016, pp. 1-25, vol. 8, No. 396, MDPI.

Muhammad et al. "Green Synthesis of Gold Nanoparticles and Their Characterizations Using Plant Extract of Papaver somniferum", Nano Science & Nano Technology: An Indian Journal, Sep. 7, 2017, pp. 1-8, vol. 11, No. 2., Trade Science Inc.

Al Yasiri, "Synthesis and Evaluation of Radioactive Gold Nanoparticles for Cancer Treatment and Imaging", published May 13, 2016.

* cited by examiner

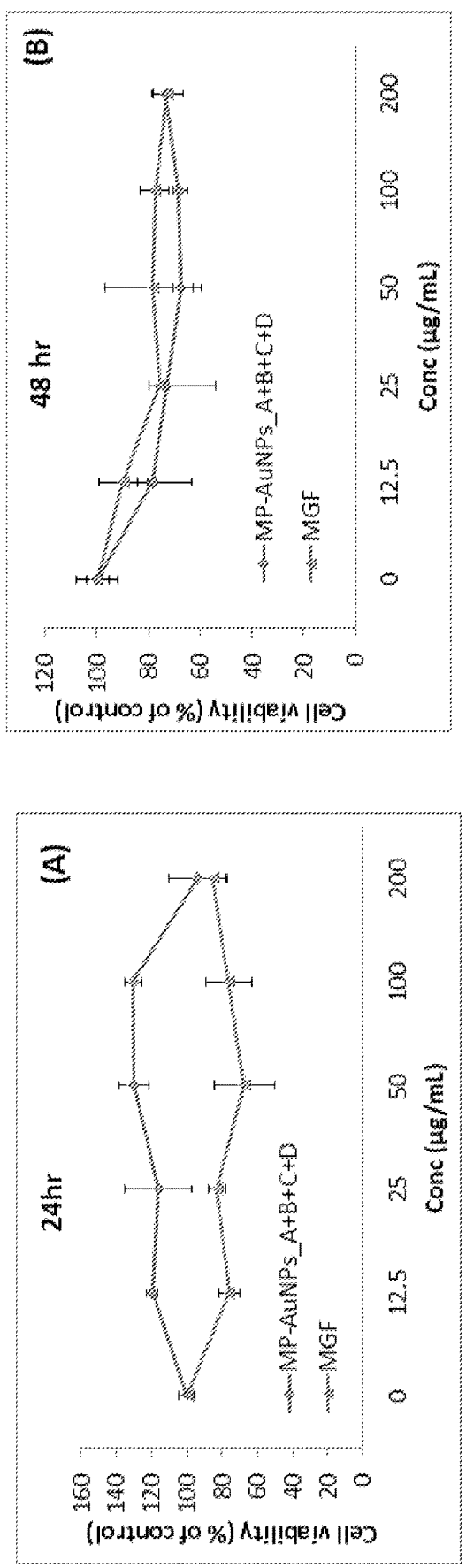
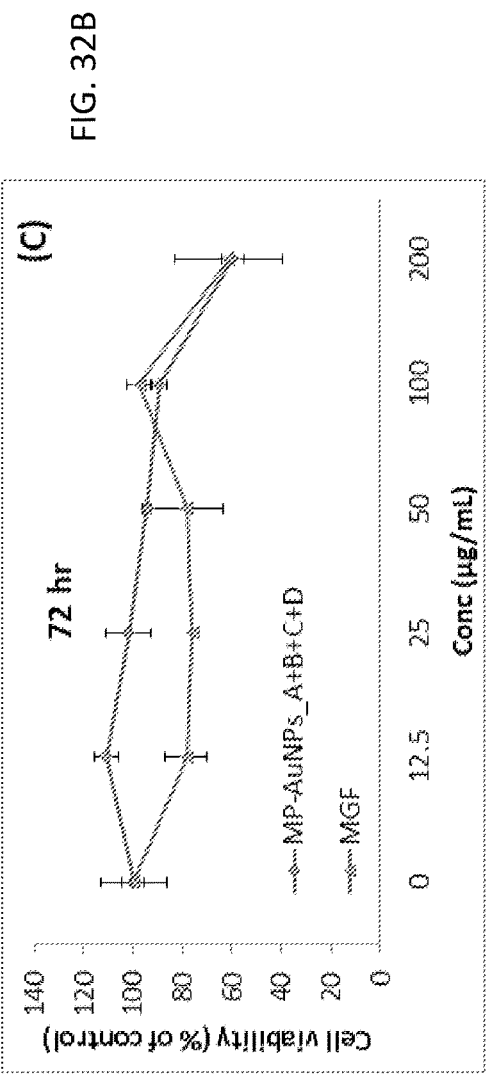
FIG. 32A
FIG. 32B
FIG. 32C

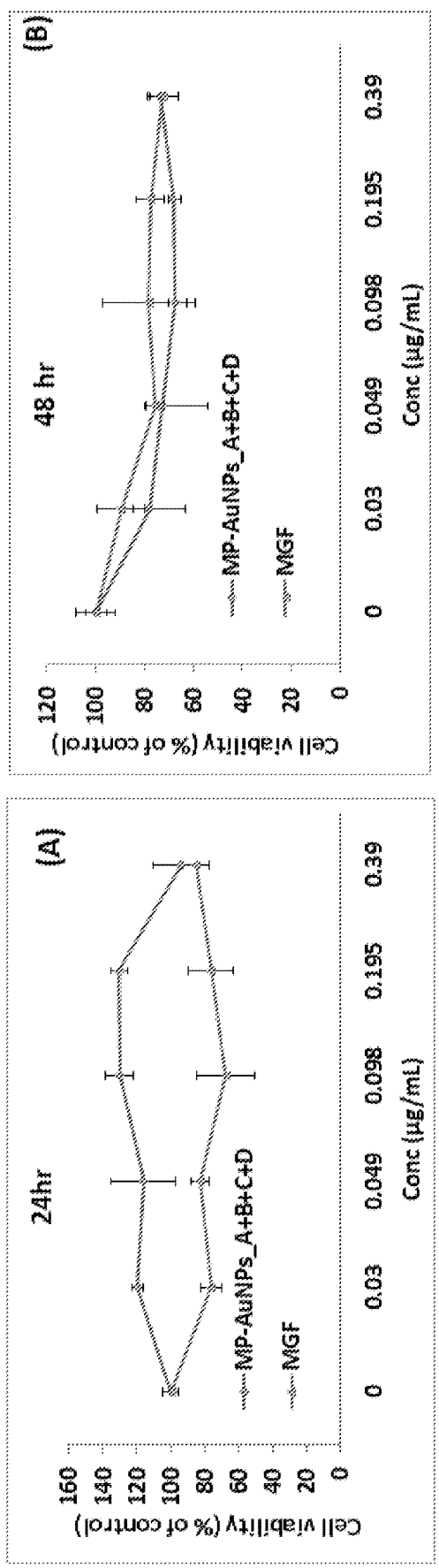
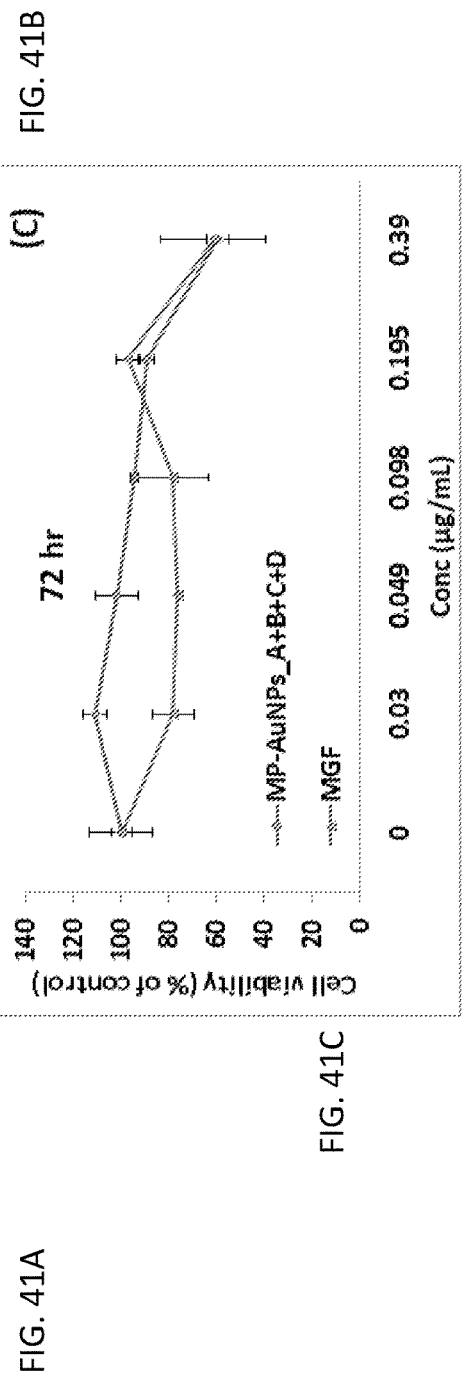
FIG. 41A
FIG. 41B
FIG. 41C

A) Untreated PC-3 cells

B) Mango peel-AuNPs treated PC-3 cells

C) Untreated MDA-MB-231 cells

D) Mango peel-AuNPs treated MDA-MB-231 cells

AYURVEDIC ENCAPSULATED GOLD NANOPARTICLES, FABRICATION METHODS AND CANCER THERAPEUTIC METHODS

PRIORITY CLAIM AND REFERENCE TO RELATED APPLICATION

The application claims priority under 35 U.S.C. § 119 and all applicable statutes and treaties from prior provisional application Ser. No. 62/459,388, which was filed on Feb. 15, 2017.

FIELD

Fields of the invention include gold nanoparticles, nanomedicine and cancer therapy. An example application of the invention is immunotherapy for the treatment of prostate cancer and other cancers.

BACKGROUND

Ayurvedic medicine is an ancient healing modality having roots of its origin in India about 5,000 years ago. This is the oldest medical system in the world, advocating holistic medicine principles aimed at achieving prevention and curative therapies to restore balance in the human body in order to prevent long-term illness and to promote natural wellness. In most countries, Ayurvedic medicine is still considered to be an "alternative" medical modality. However, in the United States, Japan, Germany, and many countries, Ayurveda is gaining prominence because of its inherent power of providing a healing mechanism addressing the entire human body to treat diseases by identifying primary causes of illness—all with minimal or no toxic side effects. Known Ayurvedic medicines are administered in combination with a plethora of herbs, metals and metal ions in the form of ash, referred to as 'Bhasma' in the Ayurvedic literature. Gold ash (Swarna Bhasma), mixed with cocktail of herbs, has been extensively used in the treatment of cancer, arthritis (both Osteo and rheumatoid), various infectious diseases and in clearing blocked arteries in cardiovascular therapy. Gold ash formulations are also used in treating various neurological disorders.

The undefined chemical formulations of gold ash make the preparations unpredictable. Irreproducible chemical species cause high unpredictability in administering well-defined active ingredients through scientifically acceptable measured doses. These challenges have often resulted in high toxicity of metallic species, as well as sub-optimal bioavailability of biologically active species. This results in significant challenges for wider acceptability of Ayurvedic medicines by regulatory agencies such as the US/European Food and Drug Administrations (FDAs).

Patients with localized prostate cancer are often successfully treated via surgery or radiotherapy, while those with metastatic conditions are treated through androgen deprivation therapy (ADT). See, A. J. Chang, K. A. Autio, M. Roach, 3rd and H. I. Scher, "High-risk prostate cancer-classification and therapy," Nat Rev Clin Oncol. 11:308-23 (2014). There is an emerging consensus that current therapies are less effective for patients with castration-resistant prostate cancer (CRPC), where the disease manifests from an asymptomatic or minimally symptomatic, non-metastatic disease to symptomatic or highly metastatic condition. (depending on the time of diagnosis with significant interpatient variation). The United States FDA has approved several chemotherapeutic agents including docetaxel, cabazitaxel, abiraterone, and enzalutamide for treating such patients. Drug resistance attributable to modulation of myeloid-derived suppressor cells (MDSCs) is seen in a significant proportion of patients. See, Y. Rong, C. H. Yuan, Z. Qu, H. Zhou, Q. Guan, N. Yang, et al., "Doxorubicin resistant cancer cells activate myeloid-derived suppressor cells by releasing PGE2," Sci Rep. 6:23824 (2016). MDSCs induce an immune suppressive microenvironment and promote M2-polarized tumor-associated macrophages (TAMs) that support angiogenesis and metastasis. Numerous studies have shown that tissue and serum exosomes from prostate cancer patients induced high levels of macrophage polarization into an alternatively activated M2 phenotype. See, P. C. Chen, H. C. Cheng, J. Wang, S. W. Wang, H. C. Tai, C. W. Lin, et al., "Prostate cancer-derived CCN3 induces M2 macrophage infiltration and contributes to angiogenesis in prostate cancer microenvironment" Oncotarget, 5:1595-608 (2014). Therefore, a cancer treatment emphasizing personalized therapy through precision medicine, with an immune checkpoint blockade that targets M2 macrophages, would be distinguished from a plethora of "common denominator" treatment approaches in current use. There is an urgent and unmet clinical need that might be met by combining different immunotherapeutic approaches, reaping synergistic therapeutic benefits for cancer patient populations. In developing novel therapies for treating drug resistant CRPC, effective targeting of TAMs assumes a central focus. Experimental results indicate that TAMs are major contributors to drug- and radio-protective effects, and that an elevated number of TAMs and their M2 profiles are correlated with failure of therapy and poor prognosis in prostate cancer patients. See, B. Ruffell and L. M. Coussens, "Macrophages and therapeutic resistance in cancer," Cancer Cell. 27:462-72 (2015).

Prostate and most solid tumors have elevated NF-κB signaling, upregulated by the release of cytokines by M2 macrophages in the tumor microenvironment. Compelling evidence shows that chemotherapeutic treatment of solid cancers in general, and prostate tumors in particular, activates NF-κB, a key transcription factor which plays a critical role in the development and progression of cancer and consequently aiding chemo and multi therapy drug resistance. Upregulated NF-κB activity can upregulate pro-survival pathways, including BCL-2. Mangiferin (MGF) has been shown in independent studies to inhibit both NF-κB and BCL-2 when administered orally. See, F. Gold-Smith, A. Fernandez and K. Bishop, "Mangiferin and Cancer: Mechanisms of Action," Nutrients. 8 (2016). The authors noted that other anti-cancer agents had been encapsulated to improve pharmacokinetic properties. The authors also discussed, on page 19, the need for a "smart vehicle" for mangiferin delivery to tumor cells, while noting that such a vehicle did not exist and that such a vehicle would have to be unique to mangiferin.

Recent studies have shown the relationship of the presence of NF-κB to the survival of cancer cells and the response of immune cells to cancer cells. B. Kuhnemuth, L. Muhlberg, M. Schipper, H. Griesmann, A. Neesse, N. Milosevic, et al., "CUX1 modulates polarization of tumor-associated macrophages by antagonizing NF-kappaB signaling," Oncogene. 34:177-87 (2015). Cancer stem cells also manifest activated NF-κB, thus contributing to the promotion of a pro-inflammatory environment leading to inhibition of apoptosis. Activated NF-κB polarizes macrophages towards the alternatively activated M2 phenotype responsible for catalyzing tumor growth and even bringing about resistance to drug treatment. The direct correlation of NF-κB in triggering M2 macrophages in prostate tumor angiogenesis, invasion, metastasis, immunosuppression, and chemotherapeutic treatment resistance singularly and collectively makes a compelling case for the design of NF-κB- and TAM-M2-macrophage-targeting drug.

Increasing evidence from clinical data has lead the present inventors to hypothesize that macrophages in human prostate cancer patients contribute both to the primary tumor growth and to the subsequent development of metastasis. In patients with Gleason Score (GS) 7-10 and pT3a stages, higher density of macrophages found in primary prostate tumor sites were characterized to be of the M2 macrophage phenotype. M2 macrophages within the tumor microenvironment promote angiogenesis, tumor growth, and metastasis ultimately leading to the transition into CRPCa and poor prognostic disease state. Several investigations have concluded that, to achieve effective immunomodulatory effects by immunotherapeutic agents, it is important to develop intratumoral delivery technologies of immunotherapeutic agents to reach the immune-suppressive effector cells, including M2 macrophages, which are localized within the tumor microenvironment. Indeed, there is preclinical and clinical evidence suggesting that therapeutic, systemic, anti-tumor immune response is improved when immunotherapeutic agents are delivered through intratumoral immunomodulation rather than systemically. See, K. Van der Jeught, L. Bialkowski, L. Daszkiewicz, K. Broos, C. Goyvaerts, D. Renmans, et al., "Targeting the tumor microenvironment to enhance antitumor immune responses" Oncotarget 6:1359-81 (2015). Classical methods such as catheterization for continuous delivery or slow-release of PEGylated drugs intratumorally are re-gaining favor as an approach. Nanomolecule immunotherapeutic platforms, which allow efficient penetration across the tumor vasculature due to their size, as well as active (receptor mediated) and passive (enhanced permeation and retention (EPR)) targeting, are being developed to achieve uptake and retention of optimal doses are being developed.

The present inventors and colleagues have previously developed stabilized gold nanoparticles encapsulated with proteins, peptides and small molecules. See, M. Khoobchandani, K. Katti, A. Maxwell, W. P. Fay and K. V. Katti, "Laminin Receptor-Avid Nanotherapeutic EGCg-AuNPs as a Potential Alternative Therapeutic Approach to Prevent Restenosis," Int J Mol Sci. 17, (2016); R. Shukla, N. Chanda, A. Zambre, A. Upendran, K. Katti, R. R. Kulkarni, et al., "Laminin receptor specific therapeutic gold nanoparticles (198AuNP-EGCg) show efficacy in treating prostate cancer," Proc Natl Acad Sci USA. 109:12426-3 (2012). Such nanoparticles were demonstrated to be retained in tumors through measurement of the gamma emission of Au-198 encapsulated nanoparticles, which allowed precise estimation of gold within tumor cells/tumor tissues down to sub nanomolar concentrations through scintigraphic counting techniques.

The present inventors have also previously demonstrated the effects of stabilized gold nanoparticles that were encapsulated with polyphenol—flavonoids. Katti et al US Patent Publication US 2012/0134918 discloses Gum Arabic coated $^{198}$Au nanoparticles, a method of making them, and their use as a therapeutic and imaging agent. Katti et al. U.S. Pat. No. 8,333,994 discloses formation of gold nanoparticles via reduction using black tea, turmeric, curcumin or cinnamon, and/or similar naturally occurring polyphenol- or flavonoid-rich plant material. Katti U.S. Pat. No. 9,358,310 discloses stabilized, biocompatible gold nanoparticles that are stabilized with material from epigallocatechin Gallate (EGCg). These patents demonstrate that polyphenol- or flavonoid-rich plant material can be used to reduce gold salts and produce stabilized gold nanoparticles.

Mangiferin (1,3,6,7-tetrahydroxyxanthone-C2-D glucoside) is a xanthonoid that is attached to a sugar. It is a polyphenol functionalized-D-glucoside-xanthone family of phytochemical found in abundance the Anacardiaceae and Gentianaceae family of plant species, especially in mangoes skin and honeybush tea. See, F. Gold-Smith, A. Fernandez and K. Bishop, "Mangiferin and Cancer: Mechanisms of Action," Nutrients. 8 (2016). Mango leaves have been ingested as a natural medicine for centuries in various cultures. Recent in vitro and in vivo broad spectrum anti-tumor investigations of mangiferin have been noted for its versatile anti-inflammatory, immunomodulatory, cell cycle arrest, anti-proliferative, anti-apoptotic, anti-oxidative, anti-genotoxic, and anti-viral characteristics. Gold-Smith et al., supra. A study has attributed mangiferin with a reduction in tumor volumes in comparable magnitude, and identified it as a possible D-glucoside-xanthone structural motif for cancer therapy. Gold-Smith et al., supra. Anti-angiogenesis, pro-apoptotic and cumulative antitumor properties have been theorized to result from the immunomodulatroy ability of this phytochemical to inhibit NFκB, and target TAM and downstream signaling pathways responsible for tumor progression and metastases. Gold-Smith et al., supra. Ingestion of mangiferin has been shown to produce mild to non-existent side effects. While a possible cancer therapeutic utility has been recognized for mangiferin, rapid metabolic degradation of this phytochemical in vivo has remained a significant barrier to achieving clinically relevant levels for effective cancer therapy.

SUMMARY OF THE INVENTION

An embodiment of the invention is a method of fabrication that includes mixing dried gooseberry product, mango peel product, or other product with the phytochemical existent therein, into a liquid medium to form a reducing agent solution. Gold salts are mixed into the reducing agent solution. Reaction of the gold salts proceeds, in the absence of any other reducing agent, to form a nanoparticle solution of stabilized, biocompatible, Ayurvedic encapsulated gold nanoparticles. The liquid medium consists of an alcoholic medium or a mixture of water and alcohol, or distilled (and/or de-ionized) water. The gold salts are non-radioactive gold salts. After reaction, preferred embodiments additionally mix in either mango peel or gooseberry phytochemicals, curcumin extract, and Gum Arabic.

Another preferred embodiment is an Ayurvedic medicine that consists of a non-radioactive gold nanoparticle, encapsulated with phytochemical existent in mango peal or gooseberry, in a capsule with curcumin extract and gum Arabic.

Preferred therapy methods include obtaining a solution of Ayurvedic encapsulated gold nanoparticles, and intraperitoneally injecting, intravenously injecting, or orally administering the solution into a subject having cancer.

BRIEF DESCRIPTION OF THE DRAWINGS

FIGS. 32A-32C are efficacy data of MP-AuNPs-A+B+C+D and free MGF as a control on normal endothelial cells (HAECs) cell viability; where: A=Gooseberry, B=Mango peel, C=curcumin, D=Gum Arabic;

FIGS. 41A-41C are efficacy data of MP-AuNPs-G+B+C+D and free MGF as a control on normal endothelial (HAECs) cell viability; where: A=Gooseberry, B=Mango peel, C=curcumin, D=Gum Arabic;

DETAILED DESCRIPTION OF THE PREFERRED EMBODIMENTS

Figure 1A:
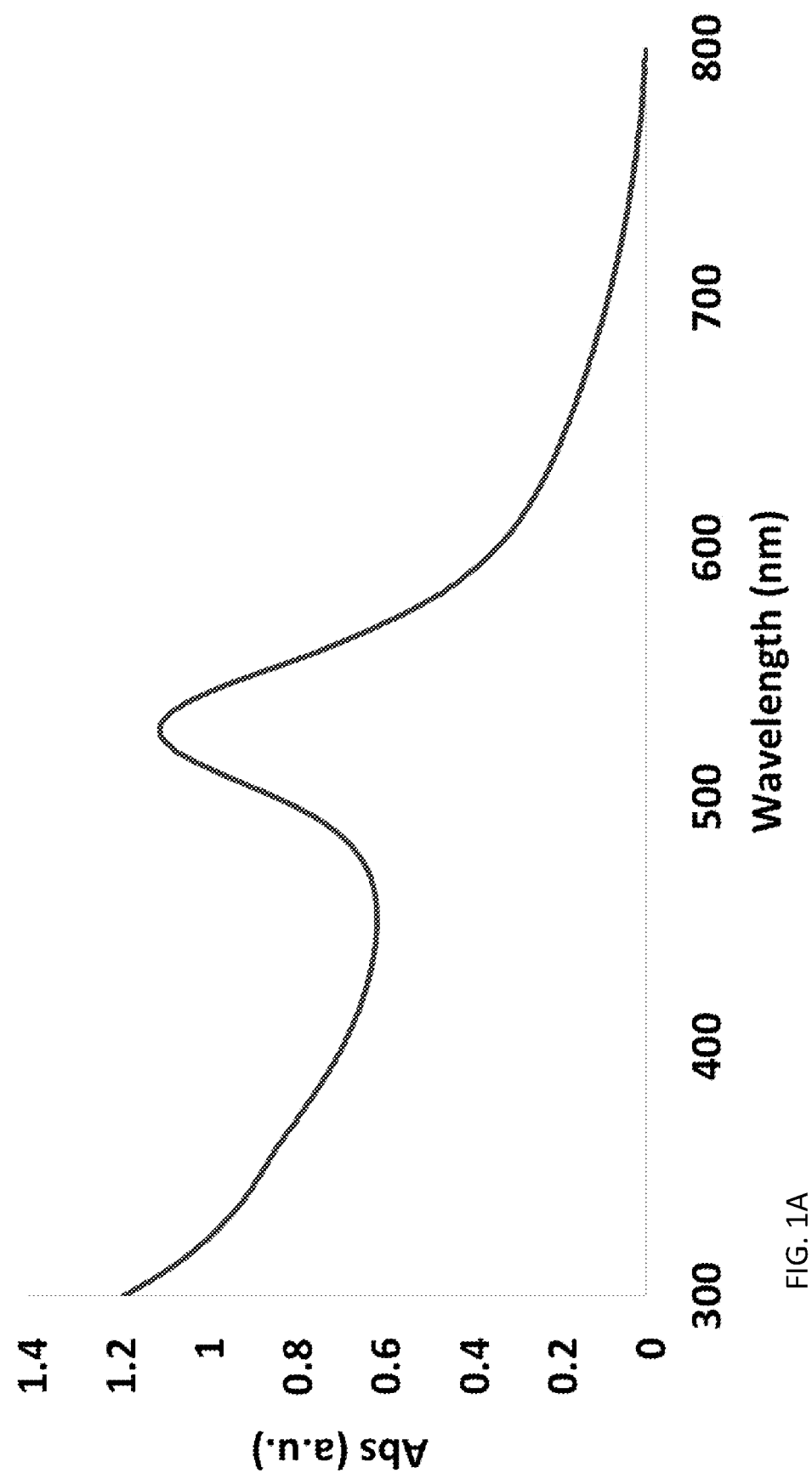
FIGS. 1A-1C represent data of UV-visible spectrophotometric analysis, a TEM (transmission electron microscopy) image, and a core size distribution of experimental gooseberry product gold nanoparticles, respectively

The present invention provides reproducible encapsulated gold nanoparticles through herbally-initiated, green nanotechnology-derived production methods, achieved via a method of fabrication that applies "Ayurvedic Principles" (no use of any toxic or manmade chemicals). Single encapsulated and complex encapsulated gold nanoparticles can be formed. Preferred single Ayurvedic encapsulated particles and a preferred treatment drug consist of gooseberry product encapsulated gold nanoparticles in a solution or dried drug material for delivery to a patient. Additional preferred single Ayurvedic encapsulated particles include mangiferin encapsulated particles. Preferred complex Ayurvedic encapsulated gold particles and a preferred treatment drug consist of gooseberry product, mango product, curcumin product, gum Arabic and encapsulated gold nanoparticles in a solution or dried drug material for delivery to a patient. The gooseberry or mango products are a cocktail of phytochemicals from gooseberry or mango peels. Acorollary would be a cocktail of phytochemicals that are existent in gooseberry or mango peels, and are derived from one or more other comparable plants that have some combination of a plurality of the existent phytochemical cocktails obtained from gooseberry or mango peels. Additional preferred single Ayurvedic enacapsulated particles and a preferred treatment drug consist of mango peel and gooseberry product encapsulated gold nanoparticles in a solution or dried drug material for delivery to a patient. Preferred complex Ayurvedic encapsulated gold nanoparticles and a preferred treatment drug consist of mango peel product, gooseberry product, curcumin product, gum Arabic and gold nanoparticles in a solution or dried drug material for delivery to a patient. The reaction to create the Ayurvedic encapsulated gold nanoparticles is conducted in the absence of any other reducing agent, and forms a nanoparticle solution of stabilized, biocompatible Ayurvedic encapsulated gold nanoparticles, either single or complex. The gold nanoparticles are not radioactive, and preferred methods for administration of both single and complex Ayurvedic encapsulated particles include oral administration, intravenous injection and/or intraperitoneal injection.

A preferred method for making gooseberry product encapsulated gold nanoparticles includes mixing of homemade dry gooseberry powder with gold salt in water. The cocktail of electron rich Phytochemicals from gooseberry reduces gold salt to produce gold nanoparticles in a 100% reproducible form. This process can be scaled for commercial production. The gooseberry product encapsulated gold nanoparticles in a solution for delivery to a patient are expected to have application for treating a myriad of human diseases and disorders, including diseases and disorders often addressed by traditional Ayurvedic medicine.

A preferred method for making complex Ayurvedic coated gold nanoparticles includes mixing of homemade dry gooseberry powder to gold salt in water followed by the addition of gum Arabic or a combination of mango peel phytochemicals, Curcumin extract, and gum Arabic. Mixing of these components is conducted. Dried drug material can be obtained by removing excess water, e.g., by lyophilizing.

Experiments have demonstrated that the present drug materials have efficacy for the treatment of human cancers. The effect of the present drug materials was tested on breast cancer cells, pancreatic cancer cells, prostate cancer cells (human and dog), and colon cancer cells.

The present invention provides a surprising result in view of prior work of the present inventors and colleagues using polyphenols such as epigallocatechin Gallate (EGCg) and flavonoid-rich plant materials, which have the propensity to reduce gold salt, and to produce the corresponding gold nanoparticles. Mangiferin, which has xanthanoid and glucose chemical functionalities, is expected to behave differently. The glucose end of mangiferin is expected to reduce gold salt, as is the xanthanoid. The combined reducing power of both xanthanoid and glucose units is strong, and such chemical reactions are expected to result in the complete conversion of gold salt into the corresponding gold metal. Contrary to this expectation, the present invention demonstrated in experiments that xanthanoid and glucose units in magiferin work in synergy to transform gold salt into the corresponding gold nanoparticles with subsequent stabilization of gold nanoparticles. The mangiferin in a solution acts as a reducing agent in the absence of any other reducing agent. No harsh chemicals are required. Gooseberry is a reservoir of a spectrum of phytochemicals, including ascorbic acid, alkaloids, benzenoids, flavonoids, terpenes, carbohydrates, gallic acid, emblicanin A, emblicanin B, chebulagic acid, corilagin, mucic acid, pedunculagin, quercetin, kaempferol and sterols. The combination of phytochemicals in gooseberry provide a cumulative high antioxidant capacity for use in treating a large number of diseases including cancer, as well as various inflammatory diseases and disorders. The presence of a large amount of Vitamin C in gooseberry is unique, and experimental evidence suggest that the effects of this strong anti-oxidant are not lost after boiling cocktails of phytochemical solutions, nor by storing the extracts for extended periods of time. This is in sharp contrast with the highly unstable antioxidant effects of Epigallo Catechin Gallate (EGCG) from tea, and phytochemicals from other plant sources.These substances decompose rapidly in solution when stored at room temperature. Therefore, EGCg is not a reliable source for scavenging hydroxyl and superoxide radicals to stimulate several antioxidant enzyme systems, including catalase, superoxide dismutase, and glutathione peroxidase.These systems serve important anti-tumor and antipyretic, analgesic, antitussive, antiatherogenic, adaptogenic, cardioprotective, gastroprotective, antianemia, antihypercholesterolemia, wound healing, antidiarrheal, antiatherosclerotic, hepatoprotective, nephroprotective, and neuroprotective needs. Additionally, the high anti-oxidant effects of phytochemicals such as gallic acid, ellagic acid, pyrogallol, some norsesquiterpenoids, corilagin, geraniin, elaeocarpusin, and prodelphinidins B1 and B2 from gooseberry provide antineoplastic effects. The anti-oxidant and cell signaling modulatory effects of gooseberry phytochemicals are significantly different compared to any other phytochemicals, and thus offer new medical uses, including radiomodulatory, chemomodulatory, and chemopreventive applications. Overall, the robust antioxidant capacity of a cocktail of phytochemicals from gooseberry and mango peel is completely unexpected to specialists/non-specialists in the field. The cocktail's free radical scavenging, antioxidant, anti-inflammatory, antimutagenic and immunomodulatory activities can be amplified by encapsulating those phytochemicals onto gold nanoparticles for the development of nano-Ayurvedic drugs in the treatment and prevention of cancer.

A preferred therapeutic method of the invention is intravenous injection of Ayurvedic encapsulated gold nanoparticles into a subject having cancer or an inflammatory disease. Therefore, this invention provides a new modality for prostate cancer treatment through an innovative nanotechnological-phytomedicine direct injection.

The present inventors have recognized that, when designing new treatment modalities for prostate cancer, the cross-talk between NF-κB transcription factor and the macrophages in the tumor microenvironment is of paramount importance, and have discovered that the Ayurvedic encapsulated gold nanoparticles are an effective modality for suppressing this cross-talk, especially with intraperitoneal injection, which also is a model for oral ingestion and intravenous injection. Experiments provide evidence of efficacy.

Example conjugated Ayurvedic encapsulated gold nanoparticles include immunomodulating αvβ3-integrin and laminin-receptor-targeting nanoparticles. The present Ayurvedic encapsulated gold nanoparticles provide a clinically significant pathway to amplify: (i) tumor cell-specific cytotoxicity; (ii) immunomodulatory suppression of NF-κB activation, and (iii) targeting tumor associated alternatively activated M2 macrophages.

Preferred embodiments of the invention will now be discussed with respect to experiments. Artisans will recognize broader aspects of the invention from the experiments.

Without being bound to the theory or the theory being necessary to practice the present invention, the inventors believe that mangiferin functionalized gold nanoparticles home in on tumor cells/tumor tissue through at least three different mechanisms. A first mechanism is attributed to the size and charge of these nanoparticles, which aid permeation and retention effects. A second mechanism is attributed to the high metabolism of sugars into tumor cells. Mangiferin includes a sugar structure. A third mechanism is attributed to the fact that the xanthanoid unit in mangiferin provides additional armamentarium for enhanced affinity of MGF-AuNPs toward tumor cells. The inventors believe that these three mechanisms work in tandem to provide unprecedented affinity for and retention of MGF-AuNPs into tumor cells, which has been demonstrated through experiments.

Figure 1B:
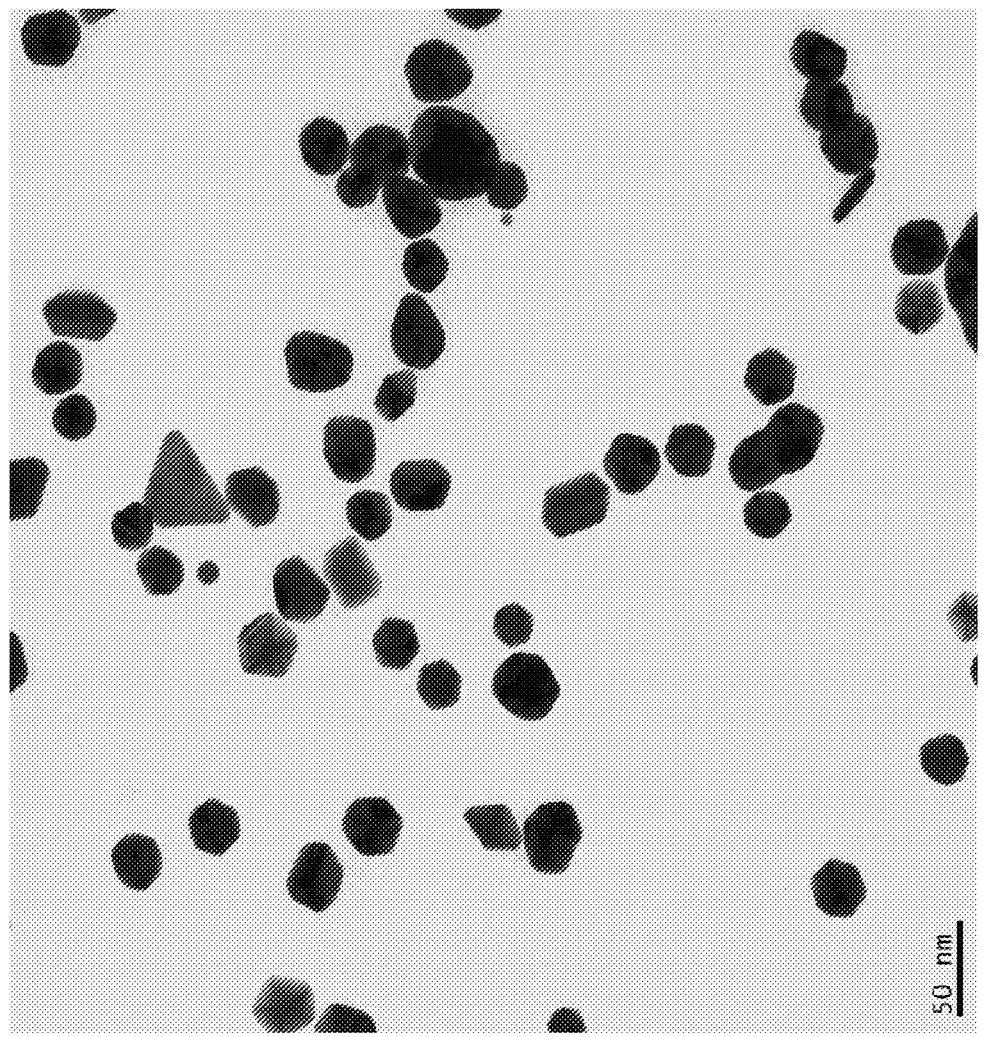
Figure 1C:
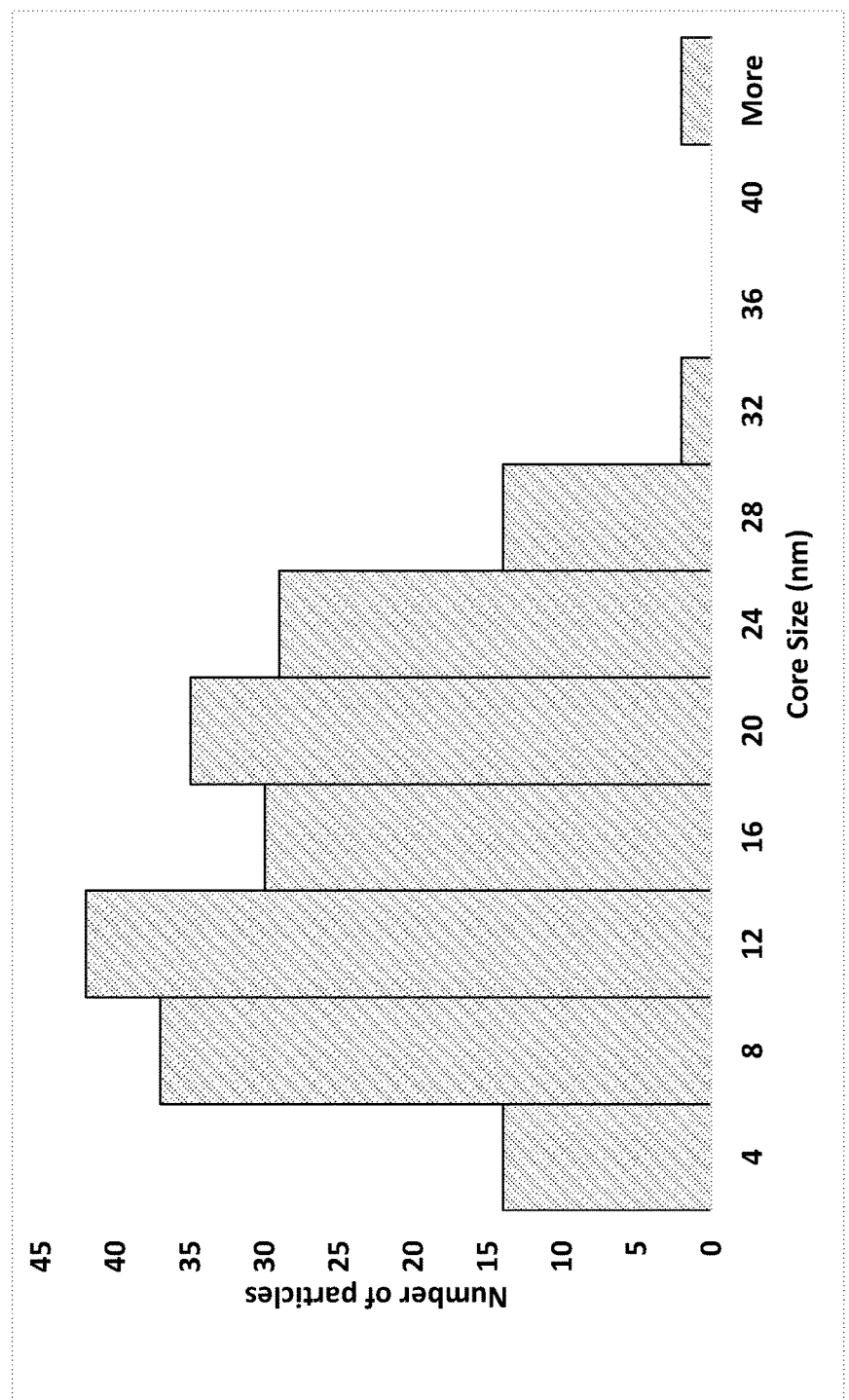

Example experimental gooseberry product encapsulated gold nanoparticles (GB-AuNP) were synthesized and characterized. The GB-AuNPs were characterized by combination of techniques including UV-Visible Spectrophotometry and TEM (Transmission electron microscopy). The UV-visible spectrophotometric analysis confirmed the surface plasmon resonance (SPR) of GB-AuNPs at 530±3 nm, which is shown in FIG. 1A, with FIGS. 1B1C showing a TEM image and a core size distribution histrogram respectively.

Figure 2A:
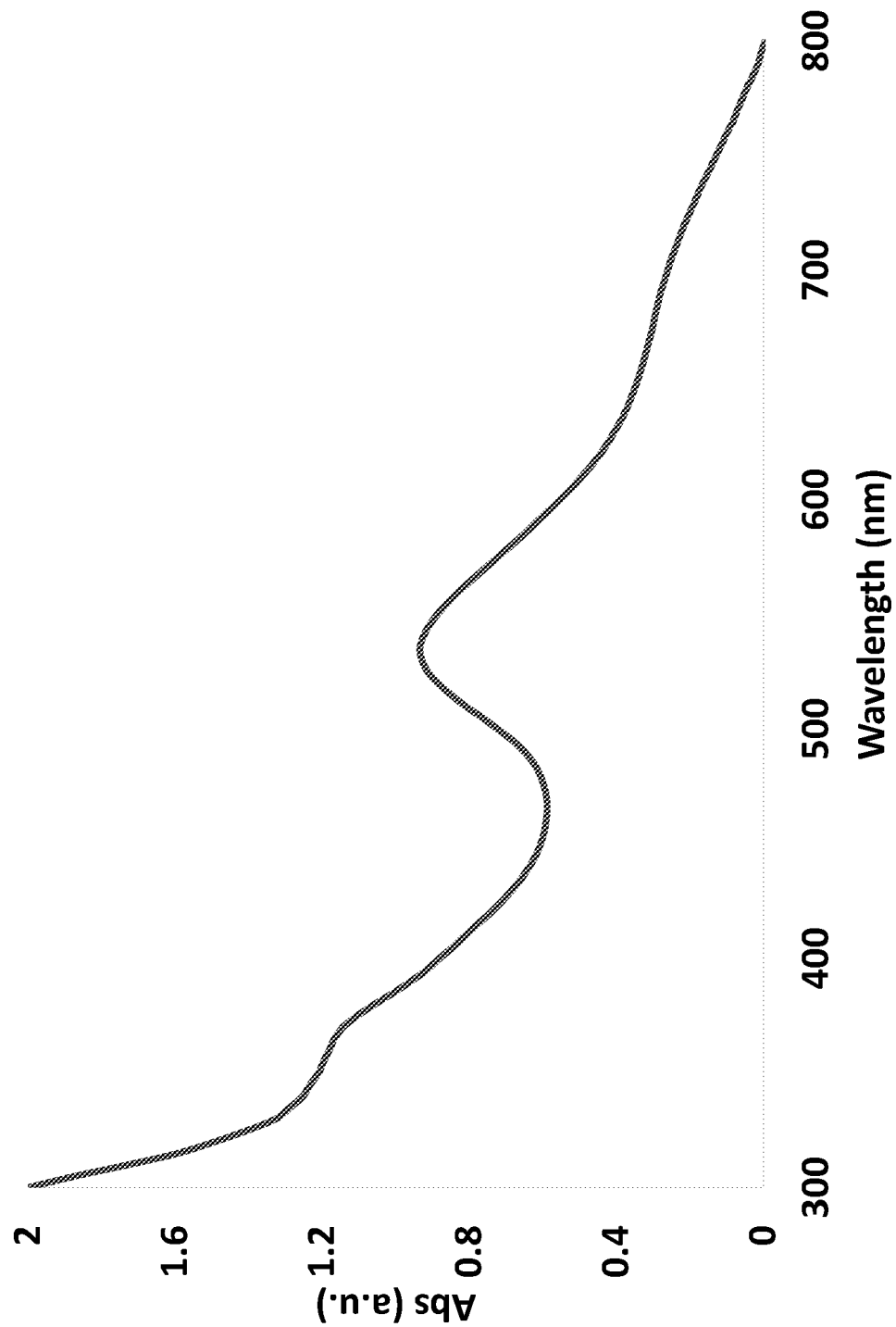
FIGS. 2A-2C represent data of UV-visible spectrophotometric analysis, a TEM image, and a core size distribution of experimental complex Ayurvedic encapsulated gold nanoparticles (gooseberry product/gum Arabic gold nanoparticles)GA-GB-AuNP) respectively.
Figure 2B:
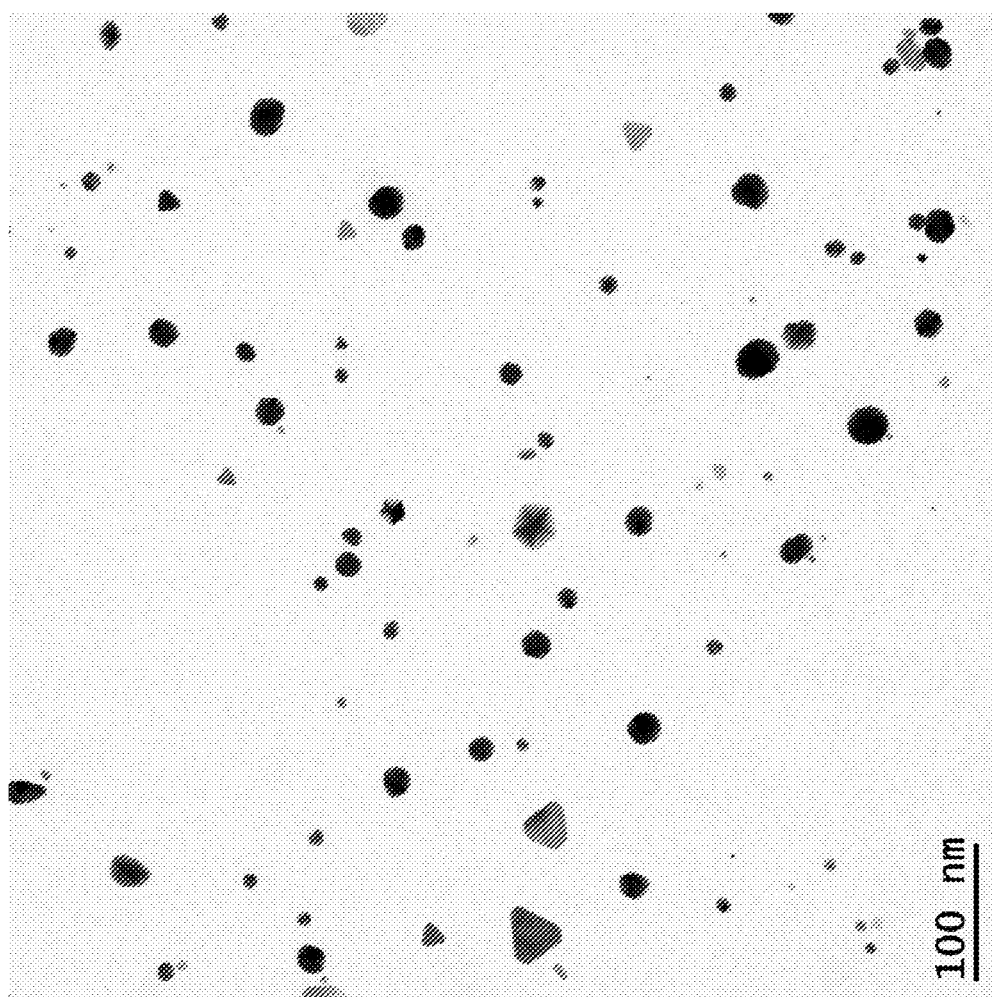
Figure 2C:
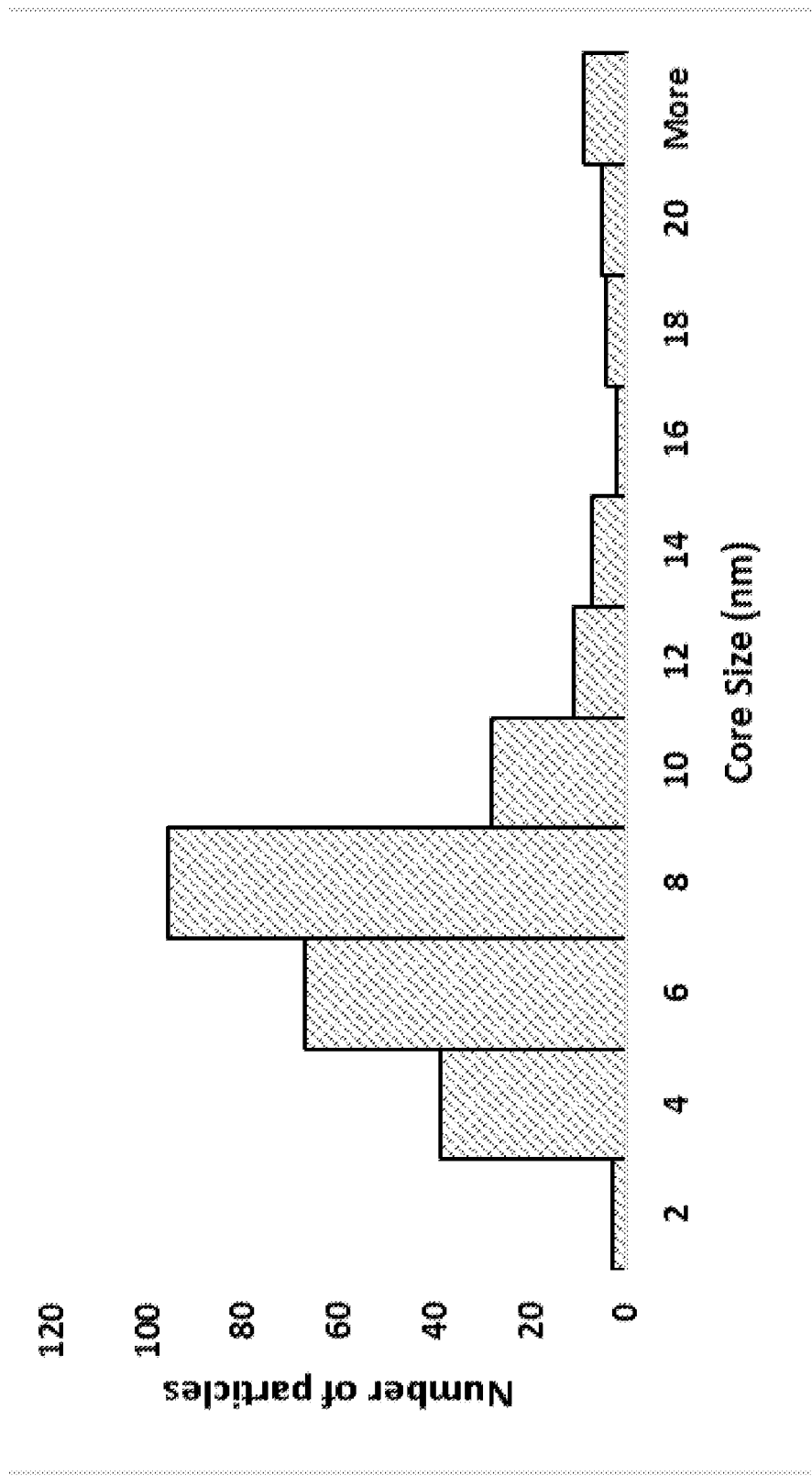

Example complex Ayurvedic encapsulated gold nanoparticles included gooseberry product/gum Arabic gold nanoparticles (GA-GB-AuNPs), which were characterized by multiple techniques including UV-Visible Spectrophotometry and TEM. The UV-visible spectrophotometric analysis confirmed the SPR of GA-GB-AuNPs at 530±3 nm, which is shown in FIG. 2A, with FIGS. 2B-2C showing a TEM image and a core size distribution histogram. The results obtained by dynamic light scattering instrument revealed that GA-GB-AuNPs showed hydrodynamic size of 137±5 nm (Table 1).

TABLE 1

| Physiochemical data parameters of (GB-AuNPs). | | | | | |
|---|---|---|---|---|---|
| Sample | UV visible spectrophotometry | DLS | Charge | TEM | Au conc by AAS |
| GB-AuNPs | 530 ± 3 nm | 65 ± 10 nm | −18.8 ± 3 mV | 25 ± 8 nm | 237 ppm |
| GA-GB-AuNPs | 530 ± 3 nm | 137 ± 5 nm | −18.8 ± 3 mV | 20 ± 10 nm | 237 ppm |

Figure 3:
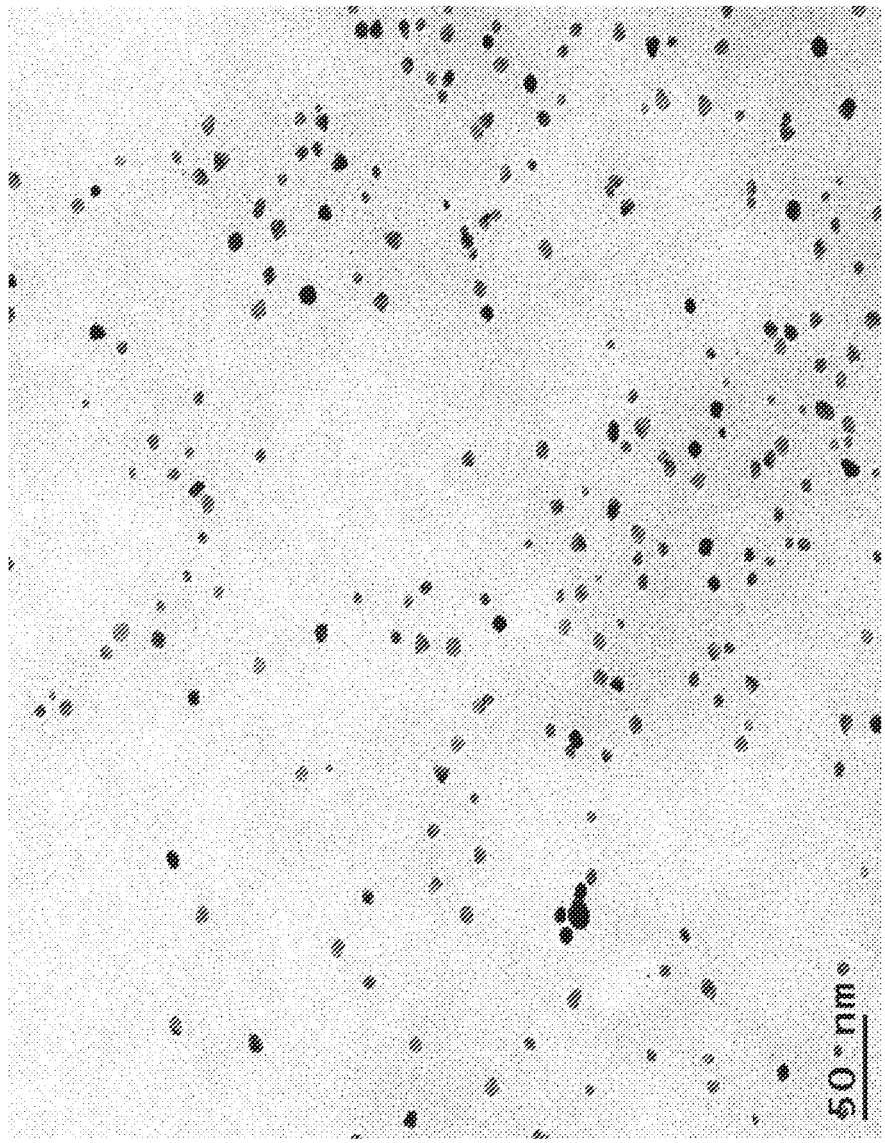
FIG. 3 is image data of core size distribution of experimental complex Ayurvedic encapsulated gold nanoparticles (gooseberry product/mango product/curcumin extract/gum Arabic gold nanoparticles) (GB-AuNPs-A+B+C+D); Where: A=Gooseberry, B=Mango peel, C=curcumin, D=Gum Arabic.

FIG. 3 shows the core size distribution of experimental complex Ayurvedic encapsulated gold nanoparticles (GB-AuNPs-A+B+C+D Nano-Ayurvedic drug). This preferred formulation added the following excipients into the GA-GB-AuNPs- (A) Gooseberry phytochemicals, (B) Mango peel phytochemicals, (C) Curcumin extract, (D) Gum arabic. The GB-AuNPs-A+B+C+D Nano-Ayurvedic drug was characterized by a TEM technique for qualitative analysis of GA-GB-AuNPs in drug formulation. The core size of GA-GB-AuNPs, obtained from data gathered by TEM, indicates that the nanoparticles are spherical, mono-dispersed and homogenous, with a core size of 26±5 nm, as shown from the FIG. 3.

Figure 4:
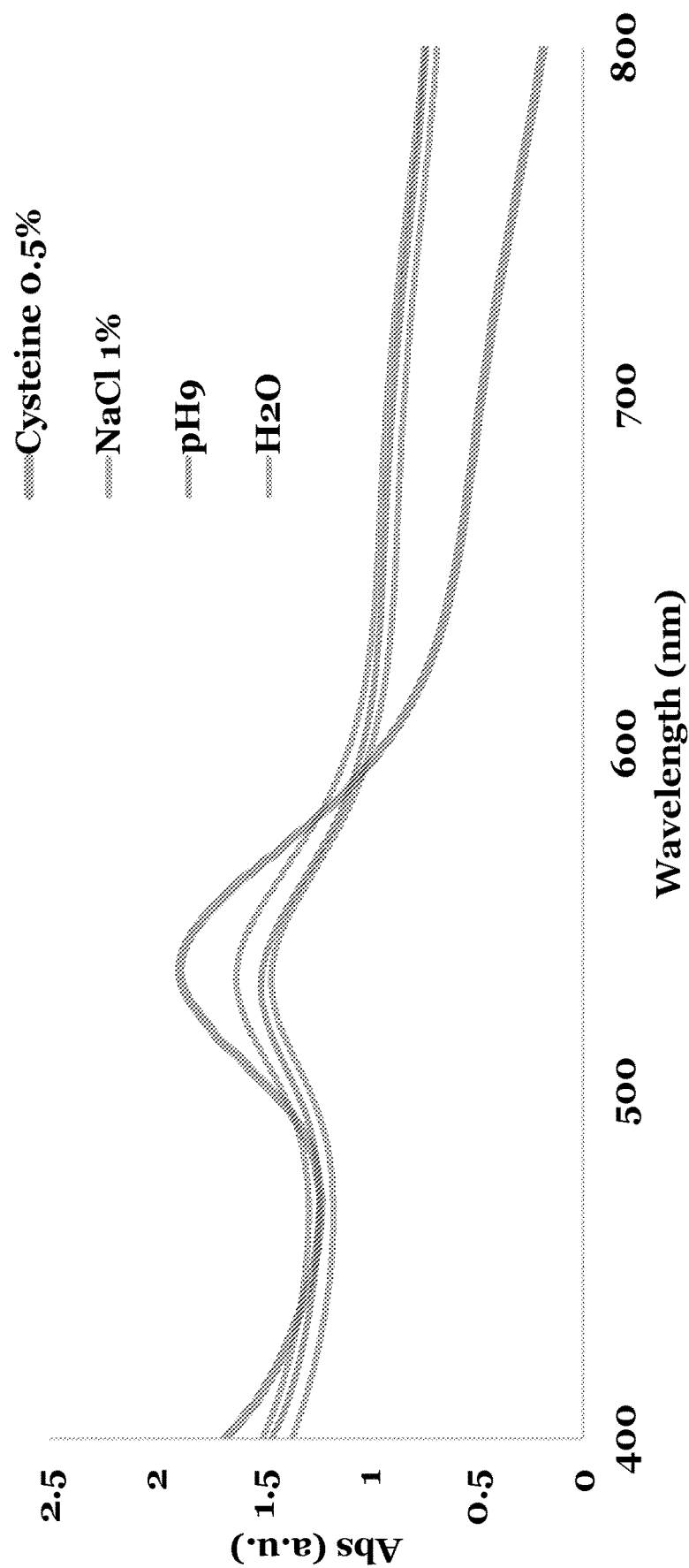
FIG. 4 is UV-Vis spectra data showing the in vitro stability of GA-GB-AuNPs in aqueous solutions after 24 hours of incubation
Figure 5:
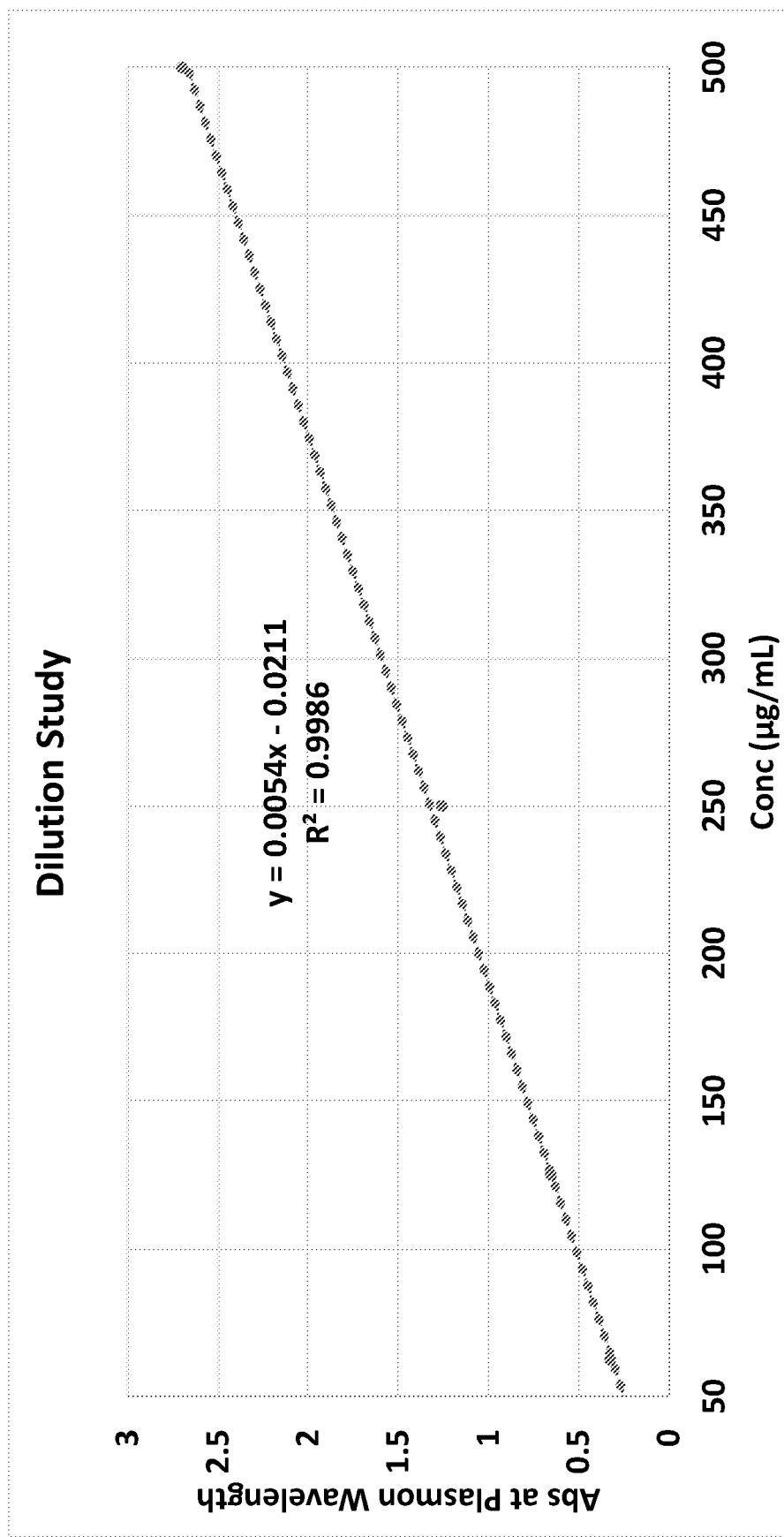
FIG. 5 is UV-Vis spectra data showing the in vitro stability of GA-GB-AuNPs at various dilutions
Figure 6C:
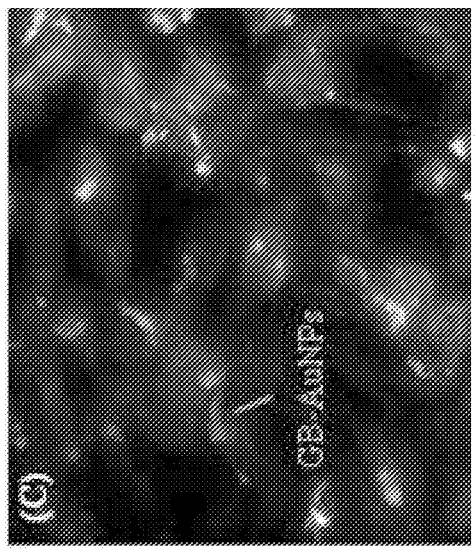
FIGS. 6A-6D are dark field cytoviva microscopic images from an in vitro (endocytosis) analysis of GB-AuNPs where: A=Gooseberry, B=Mango peel, C=curcumin, D=Gum Arabic.
Figure 6B:
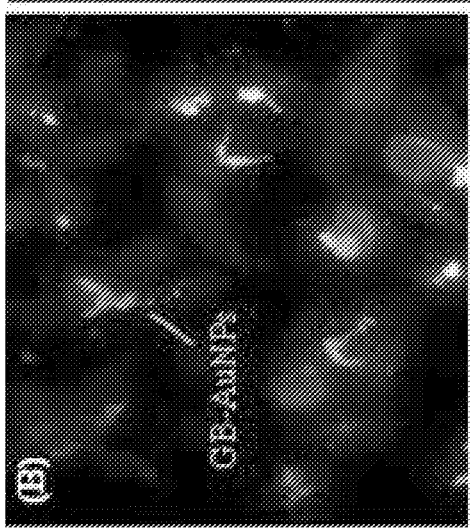
Figure 6A:
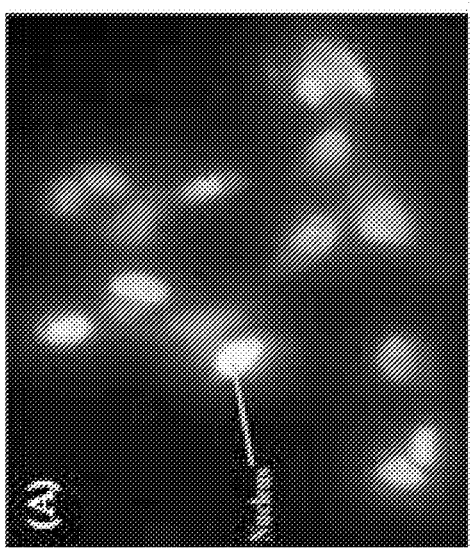
Figure 6D:

The in vitro stability of GA-GB-AuNPs was confirmed by mixing 1 ml of gold nanoparticles to 0.5 ml of aqueous solutions of 1% NaCl, 0.5% cysteine, 0.2 M histidine, pH7, and pH9 separately. The stability of the conjugates was measured by monitoring the UV absorbance over a period of 1 h, 4 h, 24 h, 48 h and 1 week. A negligible change in UV-vis plasmon band confirmed the retention of nanoparticulate composition in all mixtures, as shown in FIG. 4. The stability of GA-GB-AuNPs at different dilutions was also measured by UV-visible spectrophotometry, as shown in FIG. 5. This latter stability property is very important for biomedical applications, which require variation in dilutions/concentrations. The FIG. 5 data show that the absorbance intensity is proportional linearly with GA-GB-AuNPs concentration, with $R^2$=0.99.

Experiments studied in vitro cellular internalization (endocytosis) analysis by dark field microscopy. In one experiment, GB-AuNPs were analyzed by a dark field cytoviva microscopic technique. Ultra clean and sterile cover slips were kept in 6 well plates. The PC-3 and PANC-1 ($5 \times 10^5$ cells) were seeded into the 6 well plates in RPMI and DMEM media separately, and incubated for 24 hr in a $CO_2$ incubator at 37° C. GB-AuNPs in solution (100 µL/mL) were added to cells followed by 4 hours and 24 hours of incubation at 37° C. Images were captured via Dage Imaging Software. Dark field microscopic images unequivocally delineate that GB-AuNPs internalize effectively within PC-3 and PANC-1 cells within 4 and 24 hours of incubation time, as shown in FIGS. 6A-6D.

Figure 7:
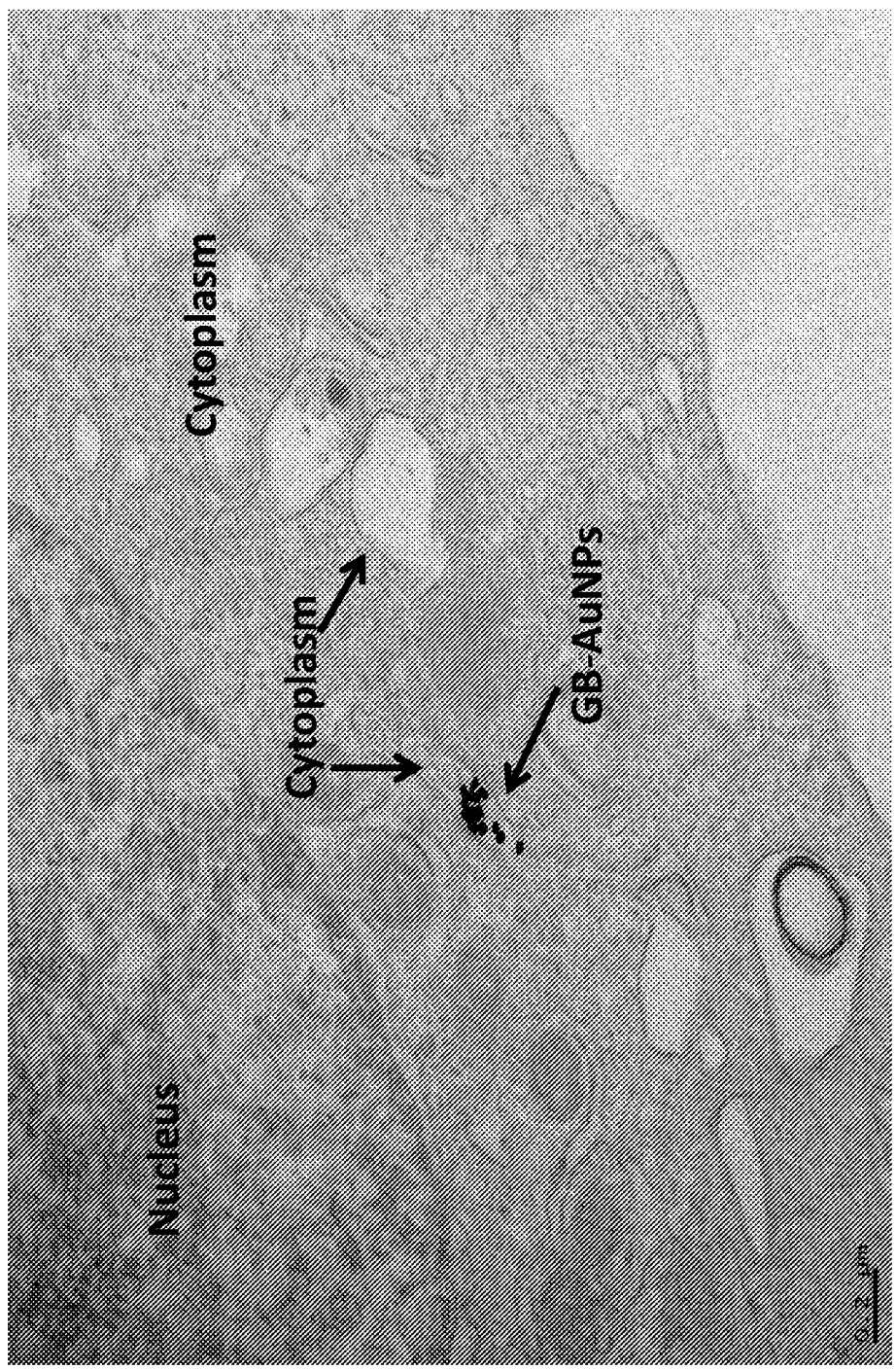
FIG. 7 is a TEM image from cellular internalization analysis of GB-AuNPs
Figure 8B:
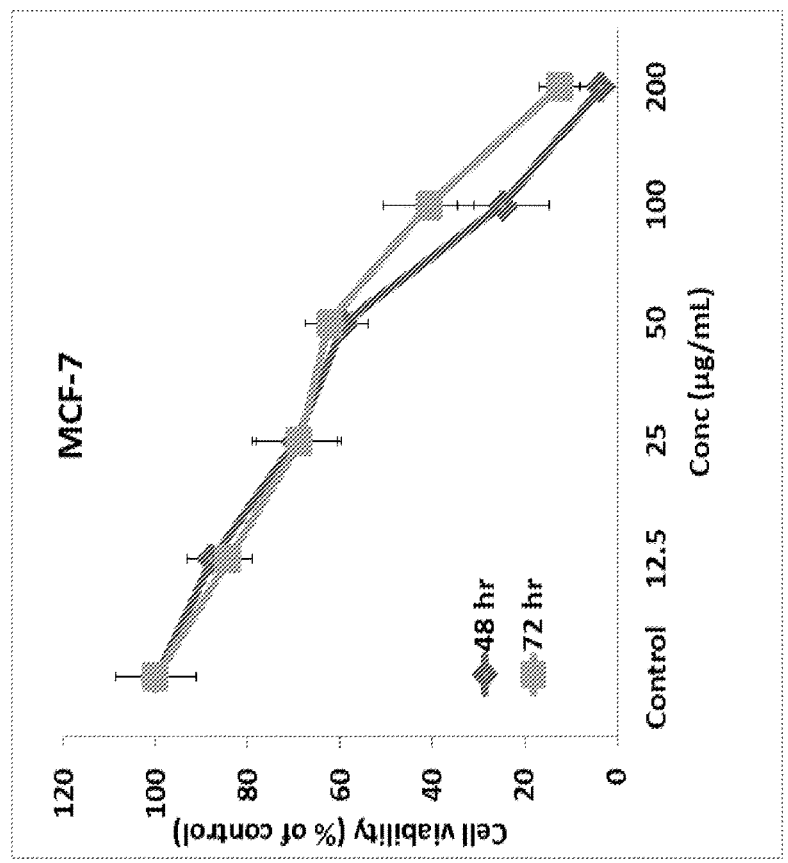
FIGS. 8A-8B are efficacy data of GB-AuNPs-A+B+C+D on breast cancer cells (MDA-MB-231 and MCF-7; where: A=Gooseberry, B=Mango peel, C=curcumin, D=Gum Arabic.
Figure 8A:
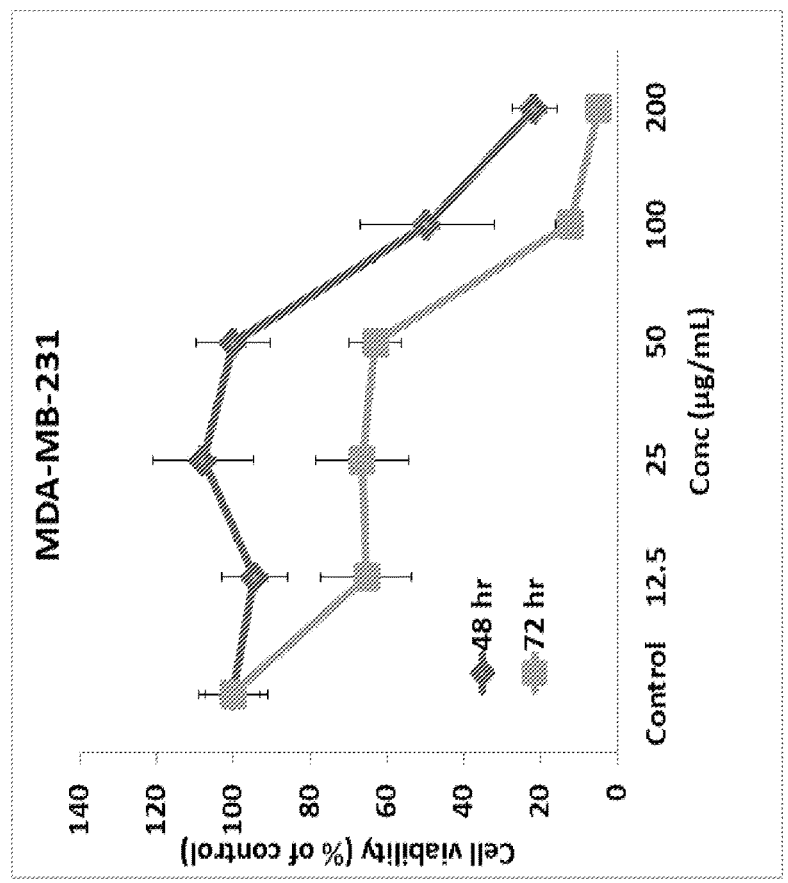
Figure 9B:
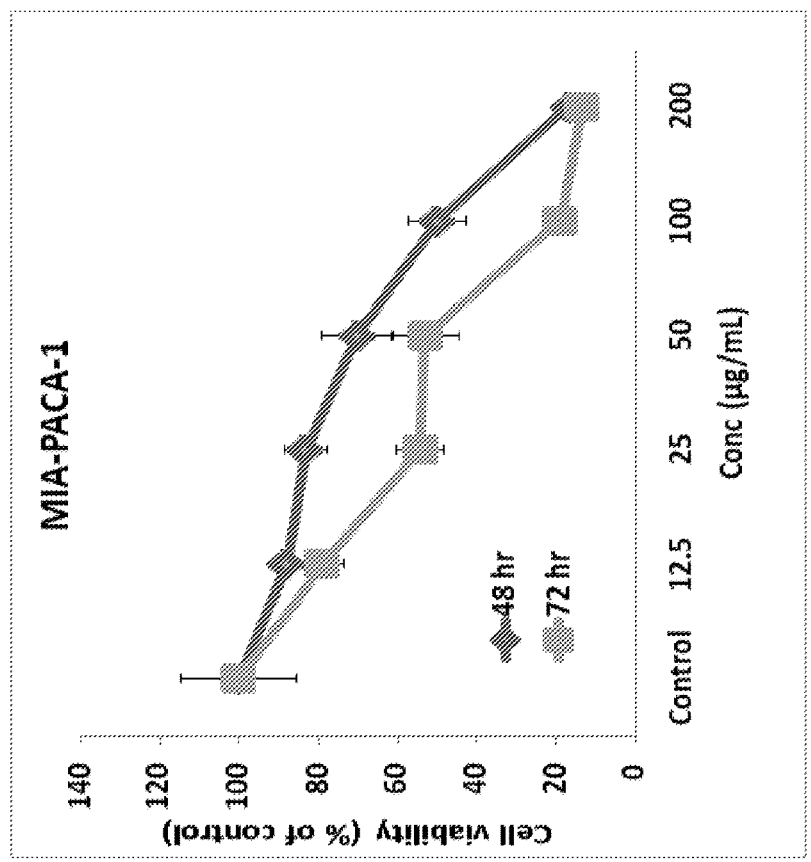
FIGS. 9A-9B are efficacy data of GB-AuNPs-A+B+C+D on pancreatic cancer cells (PANC-1 and MIA-PACA-1; where: A=Gooseberry, B=Mango peel, C=curcumin, D=Gum Arabic.
Figure 9A:
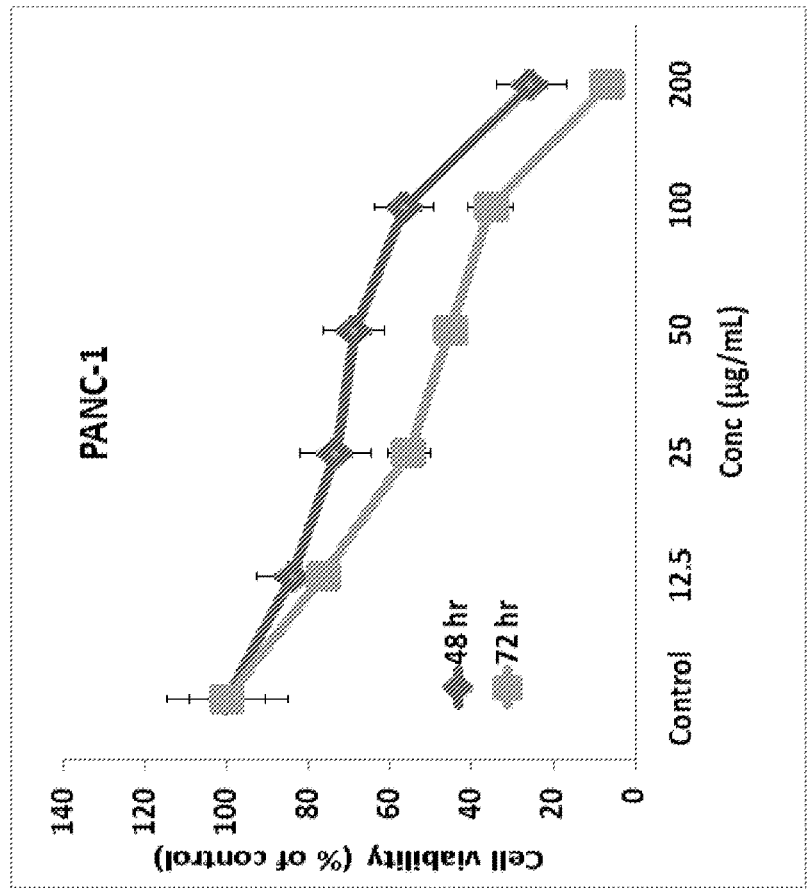
Figure 10B:
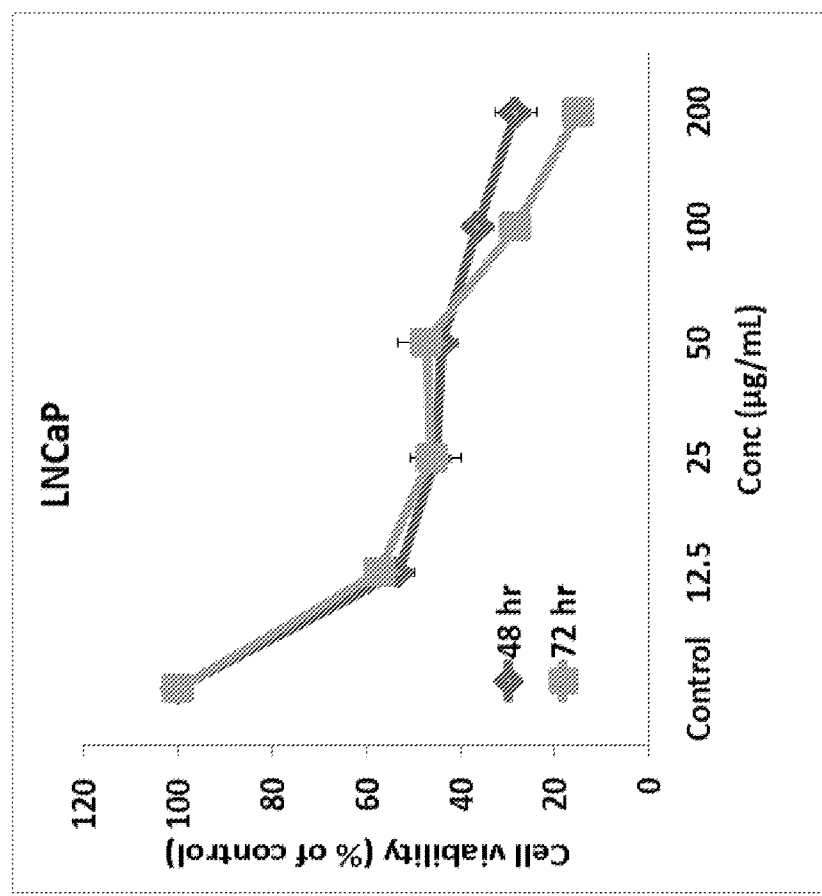
FIGS. 10A-10B are efficacy data of GB-AuNPs-A+B+C+D human prostate cancer cells (PC-3 and LNCaP) cells; where: A=Gooseberry, B=Mango peel, C=curcumin, D=Gum Arabic.
Figure 10A:
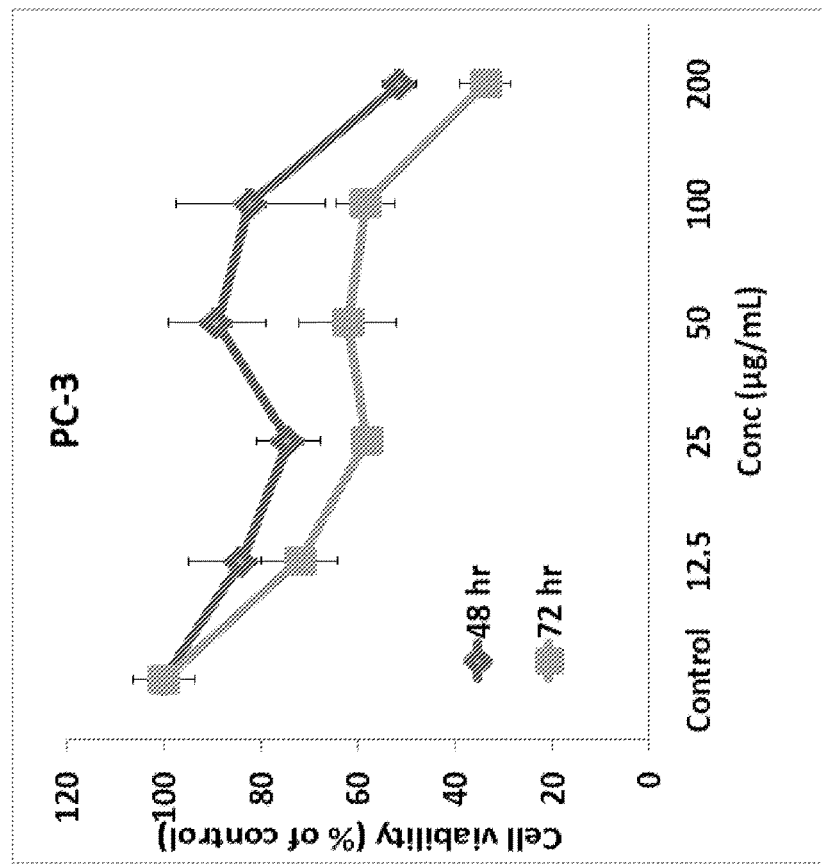
Figure 11:
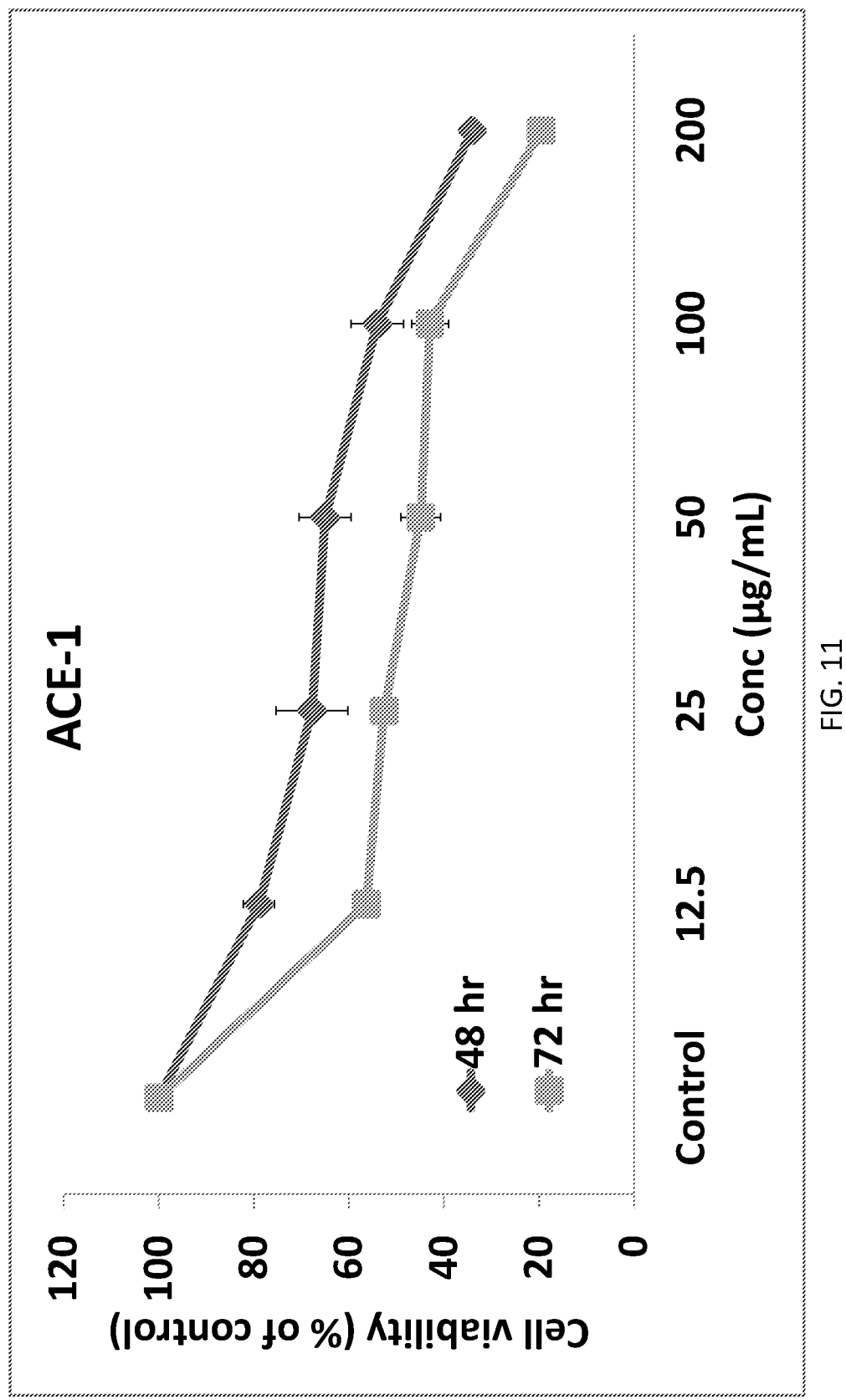
FIG. 11 is efficacy data of GB-AuNPs-A+B+C+D on dog prostate cancer (ACE-1) cells; where: A=Gooseberry, B=Mango peel, C=curcumin, D=Gum Arabic.
Figure 12:
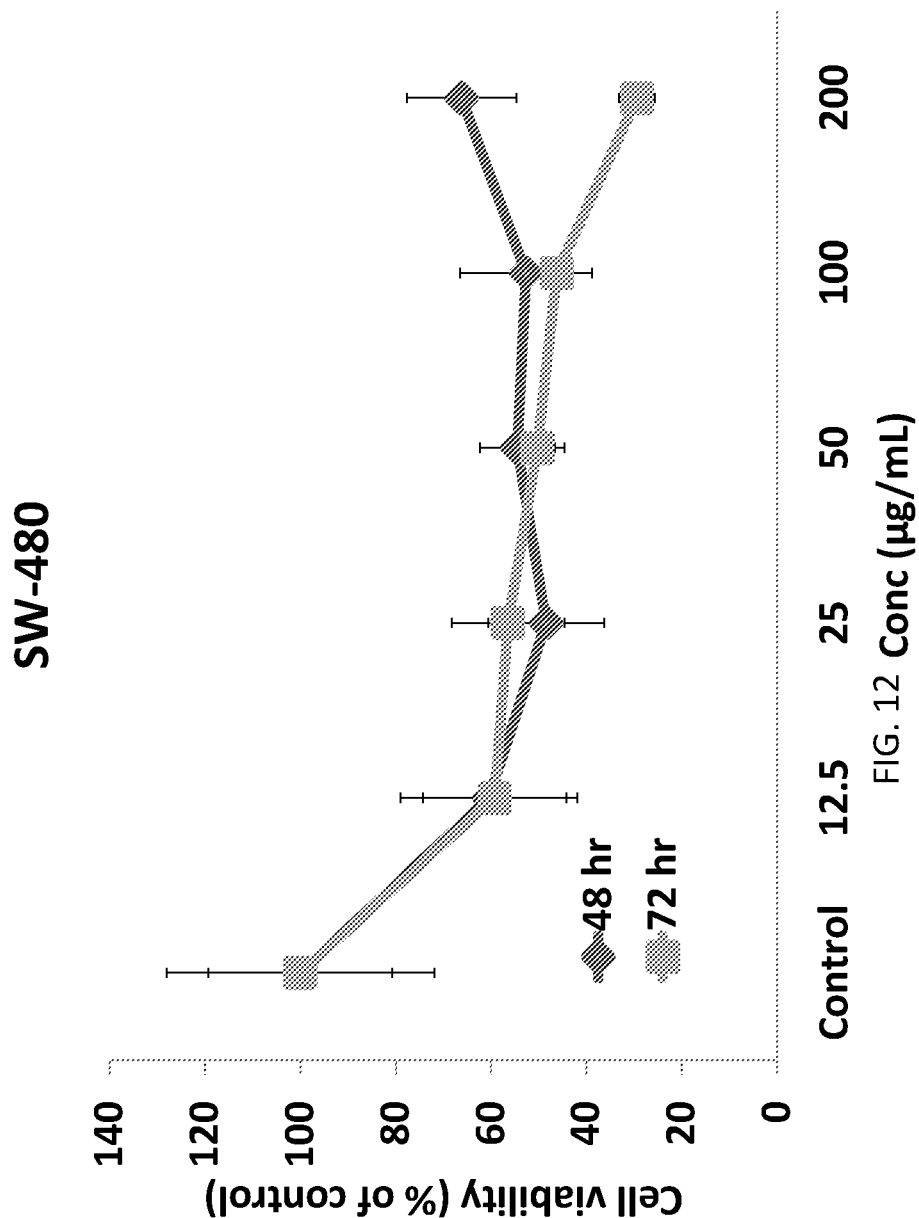
FIG. 12 is efficacy data of GB-AuNPs-A+B+C+D on human colon cancer cells (SW-480) cells; where: A=Gooseberry, B=Mango peel, C=curcumin, D=Gum Arabic.
Figures 13A, 13B:
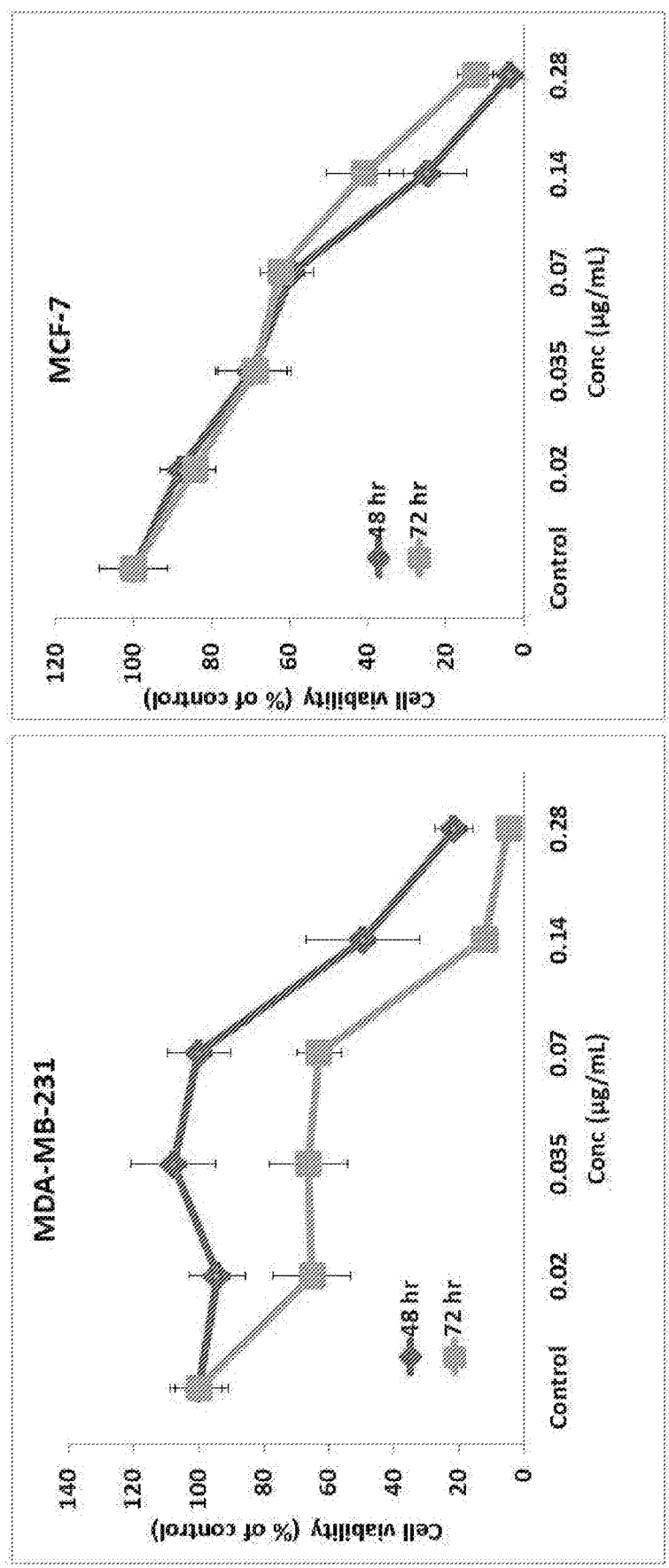
FIGS. 13A-13B are efficacy data of GB-AuNPs-A+B+C+D on breast cancer cells (MDA-MB-231 and MCF-7); where: A=Gooseberry, B=Mango peel, C=curcumin, D=Gum Arabic.
Figure 14B:
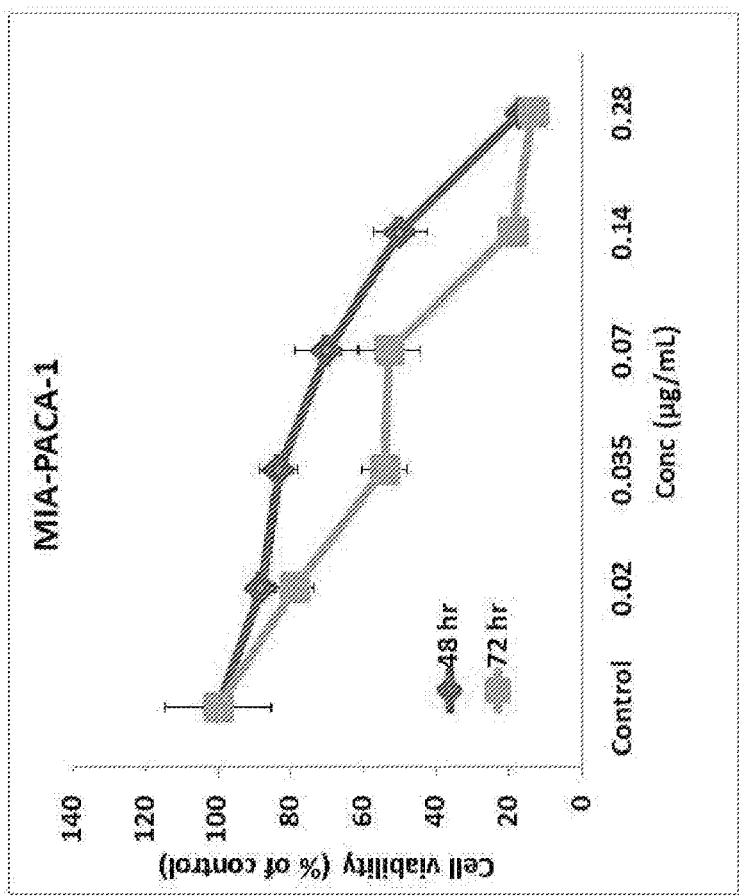
FIGS. 14A-14B are efficacy data of GB-AuNPs-A+B+C+D on pancreatic cancer cells (MIA-PACA-1 and PANC-1); where: A=Gooseberry, B=Mango peel, C=curcumin, D=Gum Arabic.
Figure 14A:
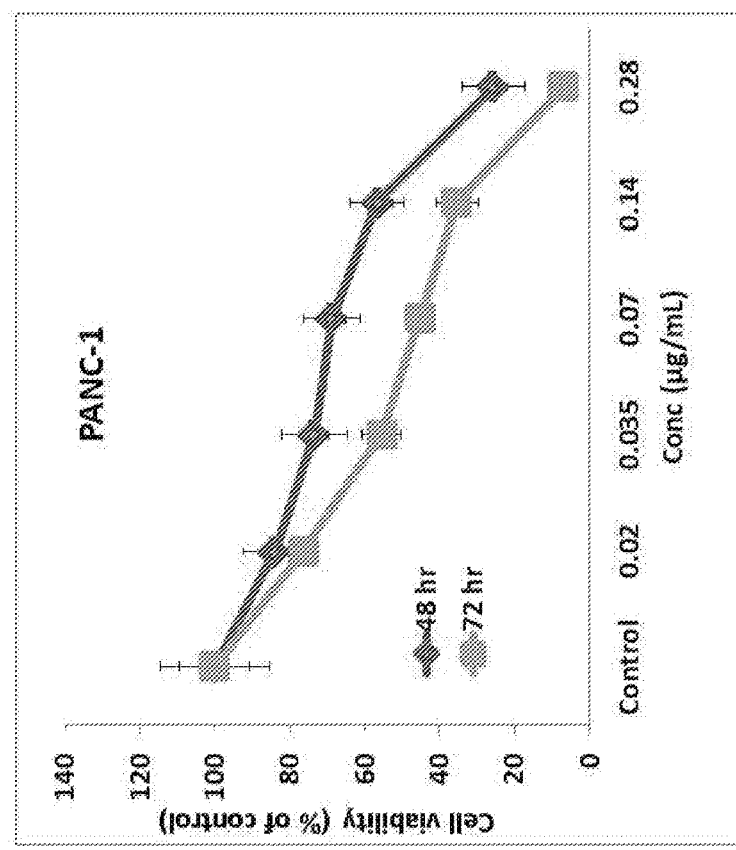
Figure 15B:
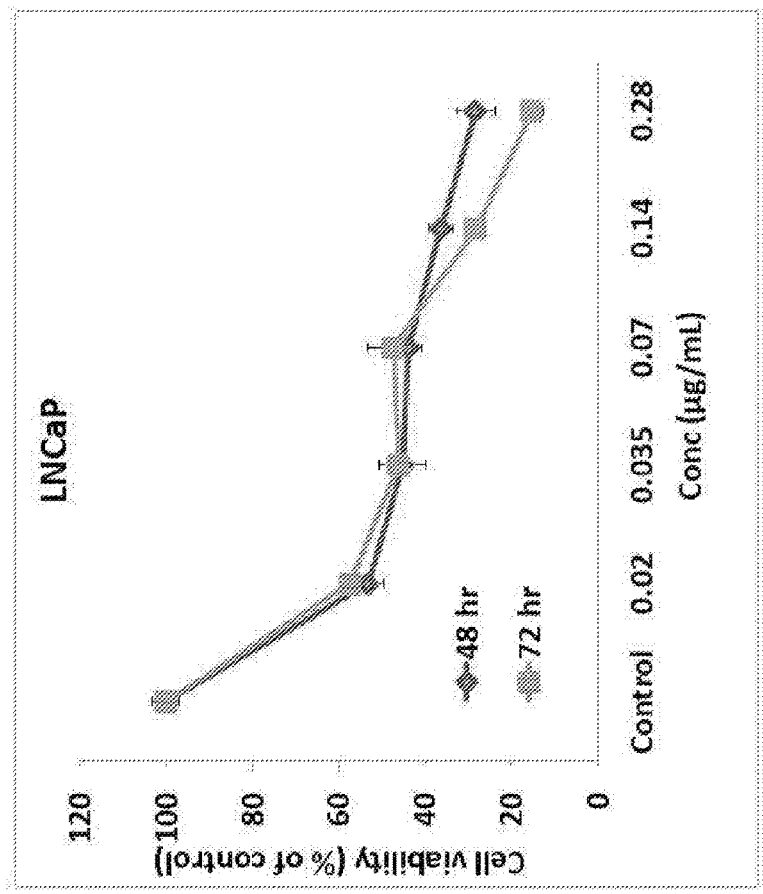
FIGS. 15A-15B are efficacy data of GB-AuNPs-A+B+C+D on human prostate cancer cells (PC-3 and LNCaP) cells; where: A=Gooseberry, B=Mango peel, C=curcumin, D=Gum Arabic.
Figure 15A:
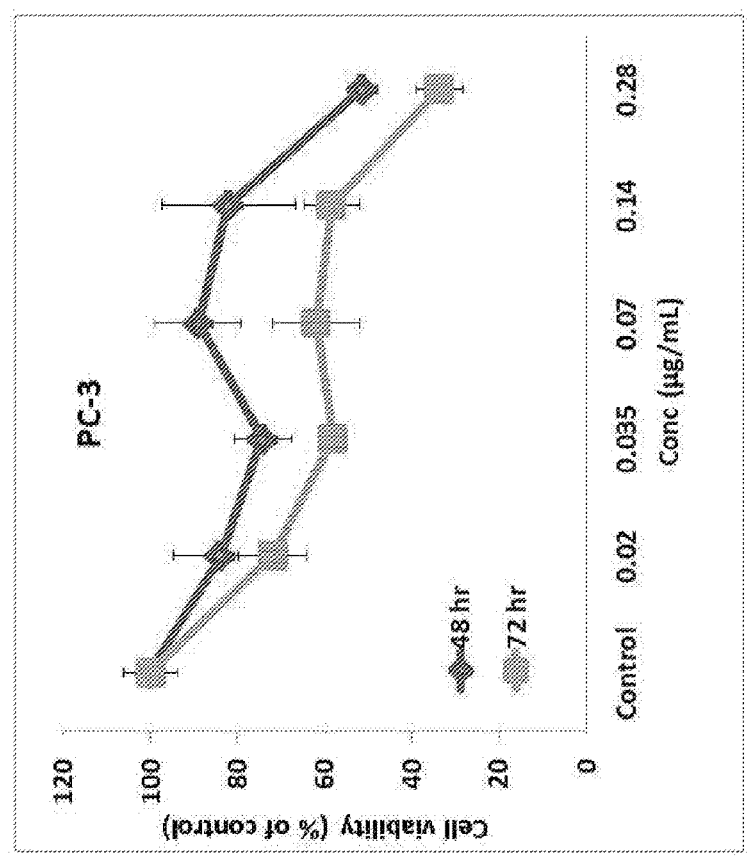
Figure 16:
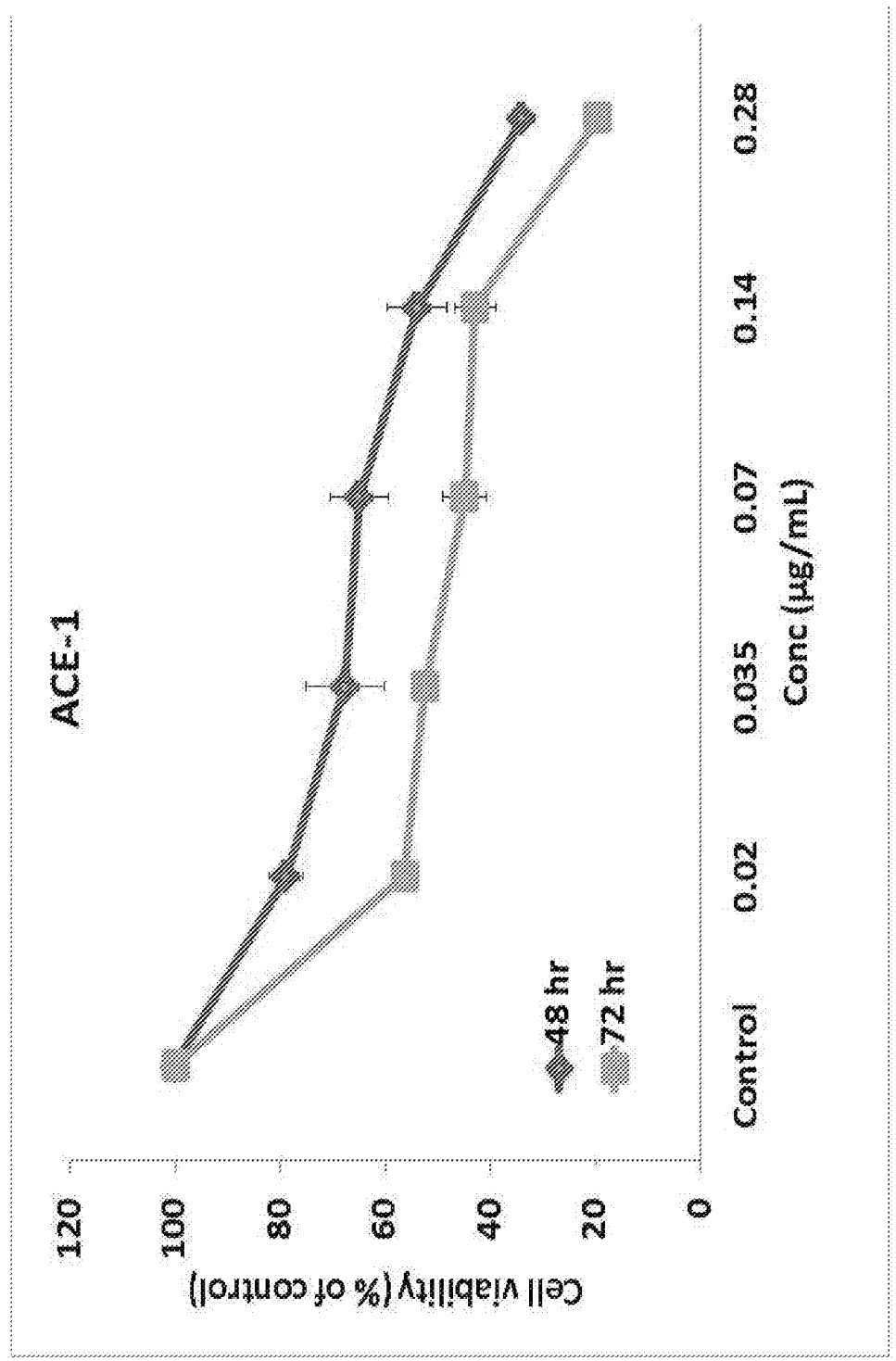
FIG. 16 is efficacy data of GB-AuNPs-A+B+C+D on dog prostate cancer (ACE-1) cells viability; where: A=Gooseberry, B=Mango peel, C=curcumin, D=Gum Arabic.
Figure 17:
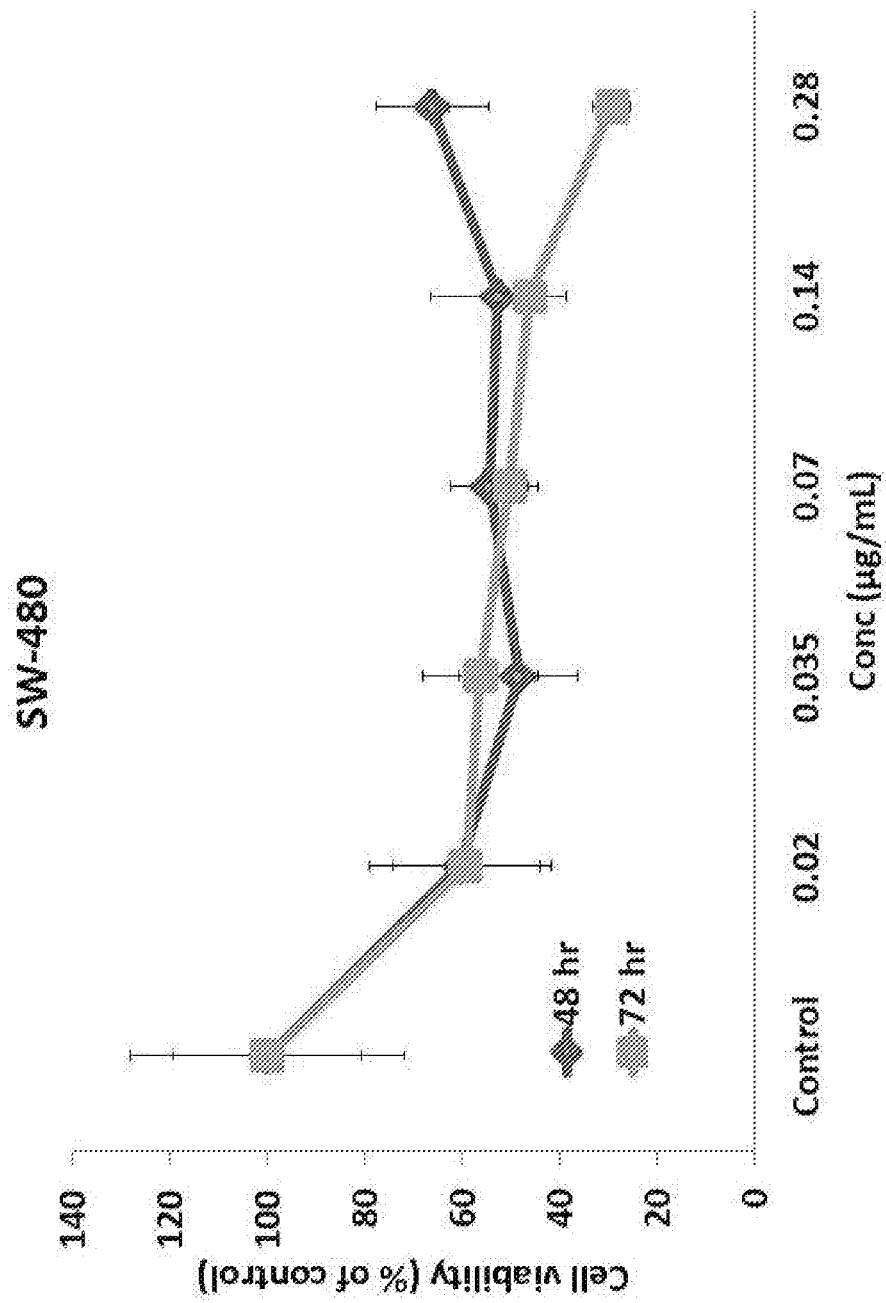
FIG. 17 is efficacy data of GB-AuNPs-A+B+C+D on human colon cancer cells (SW-480) cells; where: A=Gooseberry, B=Mango peel, C=curcumin, D=Gum Arabic.

The PC-3 cells ($5 \times 10^5$ cells) were seeded into 6 well plates in RPMI media and allowed to adhere for 24 hours in a CO2 incubator at 37° C. The media was replaced with GB-AuNPs in solution (100 µL/mL) containing medium and incubated for 2 hours at 37° C. The cellular samples were examined for endocytosis of GB-AuNPs on a JEOL 1400 TEM microscope. TEM images unambiguously indicated that these nanoparticles are internalized into vacuoles and lysosomes of the PC-3 cell line within 24 hours, as shown in the image of FIG. 7.

To test in vitro antitumor efficacy of GB-AuNPs-A+B+C+D Nano-Ayurvedic drug, the stock solution was prepared by mixing 4 mg of dry powder drug material in 1 mL of DI water. The mixture was stirred for 18-20 hours at room temperature to obtain the desired phytochemicals in DI water. The solution was then centrifuged at 8000 rpm for 5 min at 30° C. to obtain the drug solution, and a pellet. The drug solution contains combinations of ascorbic acid, alkaloids, benzenoids, flavonoids, terpenes, carbohydrates, gallic acid, emblicanin A, emblicanin B, chebulagic acid, corilagin, mucic acid, pedunculagin, quercetin, kaempferol and sterols. To estimate the amount of released phytochemicals in the drug mixture, the pellet was further dried using a lyophilizer and the dry weight was measured to be 2 mg. The weight of released phytochemicals is 2 mg. The drug mixture includes varying mixtures of phytochemicals in gooseberry: ascorbic acid, alkaloids, benzenoids, flavonoids, terpenes, carbohydrates, gallic acid, emblicanin A and B, chebulagic acid, corilagin, mucic acid, pedunculagin, quercetin, kaempferol and sterols.

To verify the amount of phytochemicals in the drug solution, the water extract was dried using rotary evaporation. The weight of phytochemicals was measured to be 2 mg, indicating that 4 mg of drug mixture provided 2 mg of phytochemicals.

Serial dilutions were prepared in RPMI/DMEM media to treat respective cells. The cell viability profile of a GB-AuNPs-A+B+C+D Nano-Ayurvedic drug was evaluated with respect to prostate cancer cells (PC-3, LNCap, ACE-1), breast cancer cells (MDA-MB-231 and MCF-7), pancreatic cancer cells (PANC-1 and MIA-PACA-1), and colon cancer cells (SW-480) by MTT assay. The cell viability profiles demonstrated that GB-AuNPs-A+B+C+D Nano-Ayurvedic drug exhibited dose dependent efficacy in cell death of cancer cells. This is shown in in FIGS. 8A-17, which demonstrate a decrease in cancer cell viability with increasing concentration of the GB-AuNPs-A+B+C+D Nano-Ayurvedic drug over periods of 48 and 72 hours. Every concentration reduced cell viability compared to a control and strong reductions were demonstrated between 50-100 µg/mL, and a 90 to nearly 100% fatality of cells was achieved with concentrations of 100-200 µg/mL.

The serial dilution doses were designed based on the amount of gold present in the GB-AuNPs-A+B+C+D. The amount of gold was analyzed by an AAS (Atomic absorption spectrophotometry) technique. The cell viability profiles demonstrated that a GB-AuNPs-A+B+C+D Nano-Ayurvedic drug exhibited dose dependent efficacy in cell death of cancer cells. These particles are formed from a combination of both encapsulation and attachment. Every ingredient need not directly attach or interact with the gold nano-metal surface. The attachment/encapsulation will happen in at least two different ways. Initially, MP or GB will attach with the gold nanoparticles surface. Then when A, B, C and D are mixed they can interact with GB (or MP), which are already bound to the gold surface, through hydrogen bonding or through direct interactions with the gold metal surface.

Materials and Additional Experimental Details.

All chemicals used in the synthesis of gold nanoparticles and cell culture, e.g. Sodium tetrachloroaurate(III) dihydrate, RPMI (Roswell Park Memorial Institute medium, commonly referred to as RPMI medium, is a form of medium used in cell culture and tissue culture) and MEM (Minimum Essential Medium (MEM), one of the most widely used of all synthetic cell culture media), Trypan blue, and MTT [3-(4,5-dimethyl thiazol-2-yl)-2,5-diphenyl tetrazolium], DAPI (4',6-diamidino-2-phenylindole) dyes were obtained from Sigma (St. Louis, Mo., USA). Fetal calf serum and TrypIE were obtained from Life Invitrogen, USA. Human prostate cancer cells (PC-3 and LNCaP), dog prostate cancer (ACE-1), breast cancer cells (MCF-7 and MDA-MB-231), pancreatic cancer cells (PANC-1 and MIA-PACA-1), and colon cancer cells (SW-480) were obtained from Cytology Core facilities of the University of Missouri, Columbia. Double distilled water was used throughout the experiments. Homemade gooseberry dry powder was used in all of the formulations. The gooseberry powder was prepared from fresh gooseberries, which were washed with cold and hot water. The berries were cut into small pieces after separating the berry content from the seeds. The cut slices were dried under shade until the pieces transformed into crisp solids. The dried gooseberry pieces were powdered using industry grade polarizers. Quality control showed a particle size: 100-150 microns. The product was free of endotoxins with a total plate count less than 1000 per gram; yeast and mould—less than 10 per gram; *E Coli* content: Absent.

TEM images were obtained on a JEOL 1400 TEM (JEOL, LTE, Tokyo, Japan). The absorption measurements were done using a Varian Cary 50 UV-Vis spectrophotometer. The hydrodynamic diameter and zeta potential were obtained using Zetasizer Nano S90 (Malvern Instruments Ltd. USA). The concentration of gold metal was calculated by Atomic absorption spectrometry.

The GB-AuNP and GB-GA-AuNP were formed by the following procedure. To a 20 ml vial, 6 ml of doubly deionized (DI) water was added, followed by the addition of homemade gooseberry dry powder (GB powder) (10 mg) with and without gum arabic (12 mg), and stirred at room temperature for 1 hr. With 6 ml DI water, a range of 8-15 mg for the GB and the gum Arabic is suitable. One hundred microliter of $NaAuCl_4$ solution (0.1 M) was added in the reaction mixture and stirred for another 3 hours at room temperature. The color changed to ruby-red within 5 minutes, confirming the formation of nanoparticles. The solution was centrifuged at 3000 rpm for 3 min to get a clear AuNPs solution by removing unreacted materials. As a variation, one could use double the volume, for example of 200 microliters of 0.1 m of NaAuCl$_4$ solution (0.1 M). When the volume of NaAuCl$_4$ is doubled, the amount of GB would increase proportionately. The volumes can also be varied with expected proportional effects within or outside of the example ranges.

The GB-AuNPs-A+B+C+D Nano-Ayurvedic drug was formulated using the same procedure as used to form GB-AuNPs. For drug formulation, the following excipients were added into the 20 mL of GB-AuNPs; (A) Gooseberry phytochemicals (2 gm), (B) Mango peel phytochemicals (4 gm), (C) Curcumin extract (1 gm), and (D) gum arabic (0.5 gm). With 20 mL of GB-AuNPs, suitable amounts are: for the gooseberry phytochemicals (2-2.5 gm), (B) Mango peel phytochemicals (4-5 gm), (C) Curcumin extract (1-1.5 gm), and (D) gum arabic (0.5-1.0 gm). All the excipients were added into the GB-AuNPs and mixed for 30-45 minutes at room temperature. The mixture was lyophilized to remove the excess water and to obtain dry drug material, the yield was 6 gm. The sample was stored in tight container at 4-8° C., and used for further antitumor cell biology studies. The mixture was lyophilized to remove the excess water and to obtain dry drug material. The yield was 6.5-7.5 gm. The sample was stored in tight container at 4° C., and used for further antitumor cell biology studies.

Research has shown that gooseberry is a reservoir of several strong antioxidant phytochemicals which include p-coumaric acid, isorhammetin glycoside, kaempferol, and quercetin. Therefore, the combined anti-oxidant effects of a cocktail of these phytochemicals would be responsible for the transformation of gold salt into gold nanoparticles. Ayurvedic medicine formulations are based on cocktail effects of phytochemicals. We have optimized the weight of gooseberry powder required for specific weight of gold salt to achieve complete transformation of gold salt into gold nanoparticles. For gold weight in the range 4-8 mg, 6-10 mg of gooseberry powder is optimum to perform complete reactions in 6-10 ml distilled water at 25-28° C.

The stability studies of GB-AuNPs were conducted by mixing gold nanoparticles with various biological solutions, such as aqueous solutions of 1% NaCl, 0.5% cysteine, 0.2 M histidine and pH7 separately. The stability of the conjugates was measured by monitoring the SPR at different time points for a week. A negligible change in SPR band confirmed the retention of nanoparticulate composition in all mixtures. The GB-AuNPs were also tested for their stability at different concentrations in water, and stability was measured by UV-visible spectrophotometry.

The endocytosis mode was investigated by incubating simple and complex Ayurvedic AuNPs with prostate and pancreatic cancer cell lines. The optimum dose and incubation time was determined with different dilutions for different time points. The concentrations are indicated in the figures. The samples were prepared using the following techniques.

The dark field data was obtained as follows. After incubation, cells were washed 10 times with 1×PBS, and fixed with 4% paraformaldehyde (PFA). Cells were further washed 2 times with 1×PBS and slides were prepared by using DAPI nuclear dye and observed with Cytoviva dark field microscope coupled with dual mode fluorescence. Cell morphology was initially observed, followed by the uptake of nanoparticles. Images were captured via Dage Imaging Software.

The TEM images were obtained as follows. After incubation, cells were washed 10 times with PBS, centrifuged into pellets, and fixed with 2% glutaraldehyde, 2% paraformaldehyde in a sodium cacodylate buffer (0.1 M). The cells were further fixed with 1% buffered osmium tetraoxide in a 2-Mercaptoethanol buffer, and then dehydrated in graded acetone series and embedded in Epon-Spurr epoxy resin. Sections were cut at 85 nm using a diamond knife (Diatome, Hatfield Pa.). The sections were stained with Sato's triple lead stain and 5% aqueous uranyl acetate for organelle visualization. The prepared samples were examined on JEOL 1400 TEM microscope (JEOL, Peabody, Mass.) operated at 80 kV at the University of Missouri's Electron Microscopy Core Facility.

Cell viability assays for the effect of a GB-AuNPs-A+B+C+D Nano-Ayurvedic drug on prostate cancer cells (PC-3 and LNCaP), dog prostate cancer (ACE-1), breast cancer cells (MCF-7 and MDA-MB-231), pancreatic cancer cells (PANC-1 and MIA-PACA-1), and colon cancer cells (SW-480) cell viability was determined using MTT assay (Sigma Aldrich). The intensity of developed color was measured by a micro plate reader (Molecular device, USA) operating at 570 nm wavelength. Percent cell viability was calculated by using the following formula: $(T/C) \times 100$, where C=Absorbance of control, and T=Absorbance of treatment. The IC-50 values were calculated using Origin software.

Figure 18:
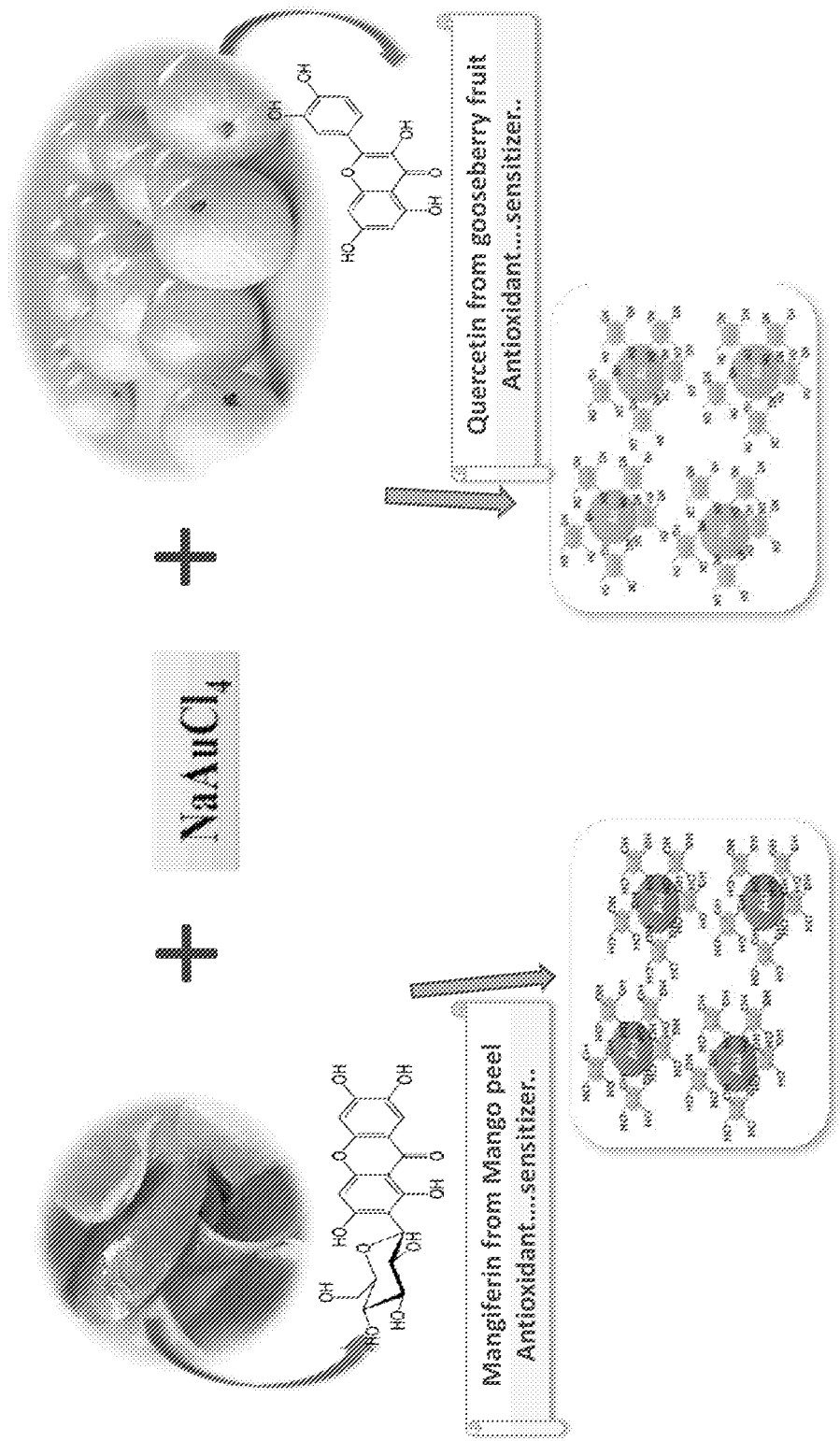
FIG. 18 illustrates a method for synthesis of mangiferin from mango peal phytochemical conjugated gold nanoparticles (MP-AuNPs)
Figure 19:
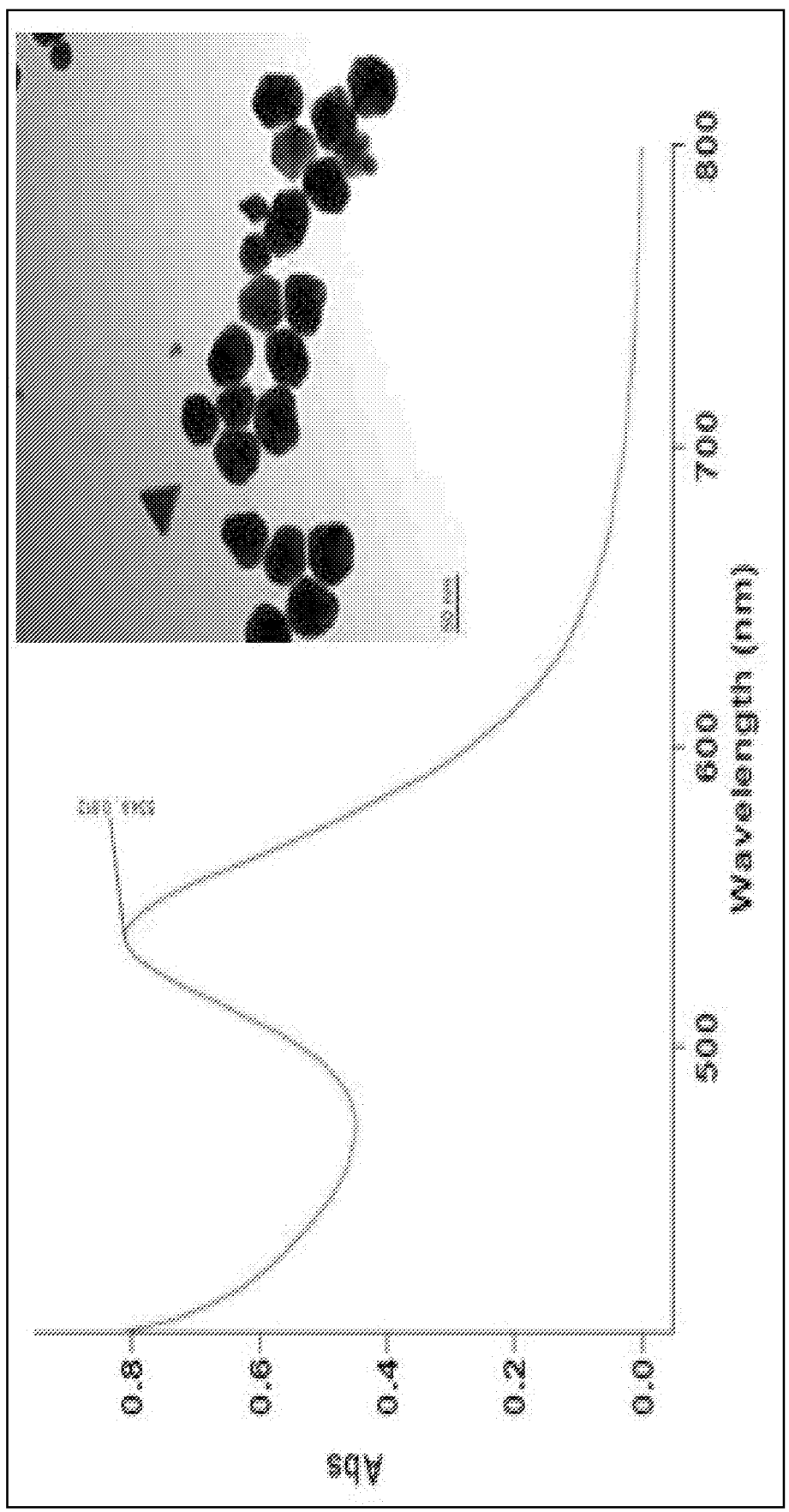
FIG. 19 is UV-Vis spectra data of MP-AuNPs.
Figure 20A:
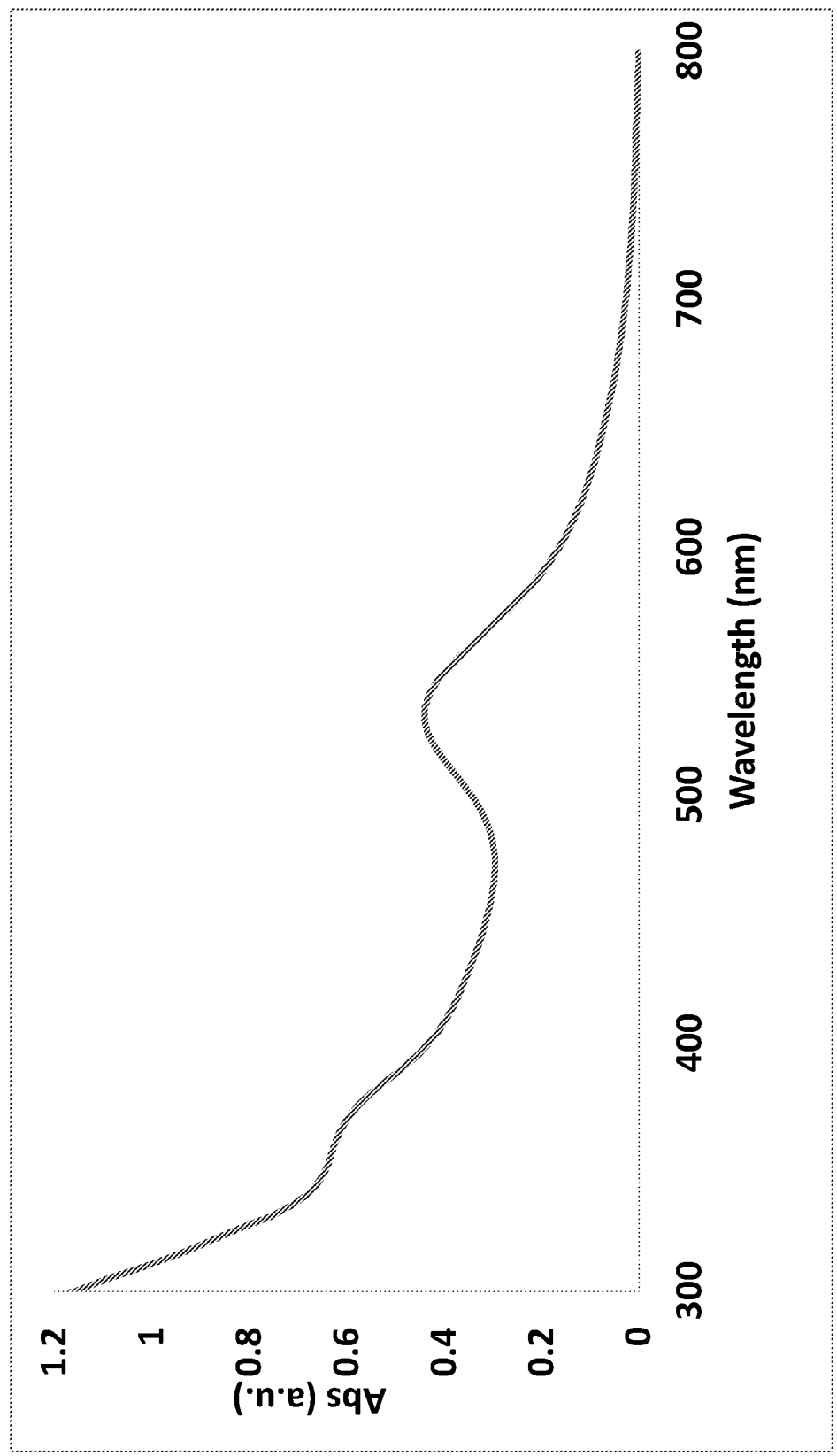
FIGS. 20A-20B are UV-Visible spectrum data of MP-AuNPs 2× and a core size distribution shown by TEM image.
Figure 20B:

Mango peel phytochemcial conjugated gold nanoparticles (MP-AuNPs) were synthesized using the optimum reduction capabilities of the strong electron rich-antioxidant phytochemicals in mango peel. The procedure is shown in FIG. 18. The production of MP-AuNPs was confirmed by the observation of color change of solutions from pale yellow to red reaction mixtures. The phytochemicals present in mango peel are powerful electron injectors. These phytochemicals also create coating on a gold nanoparticle surface, and therefore the phytochemicals play a significant role in the production and stabilization of gold nanoparticles. The AuNPs were characterized by combination of techniques including UV-Visible Spectrophotometry, DLS, and TEM. The UV-visible spectrophotometric analysis confirmed the SPR of MP-AuNPs was at 535±2 nm, which is shown in FIG. 19. This concluded the successful synthesis of MP-AuNPs. The core size of MP-AuNPs, obtained by TEM, indicated that the nanoparticles are spherical, mono-dispersed, and homogenous with the core size of 35±5 nm. The results obtained by dynamic light scattering instrument revealed that MP-AuNPs showed hydrodynamic size of 65±5 nm and a zeta potential (ζ) of −20±2 mV. The negative zeta potential provides the necessary repulsive forces required for the nanoparticles to remain stable in solution. MP-AuNPs are stable in solution for over 3 years. Phytochemical constitution in mango peel includes glucose, xanthones, mangiferin, quercetin, kaepferol, catechins, rhamnetin and a host of phytonutrients. Mangiferin, a C-glucosylxanthone (1,3,6,7-tetrahydroxyxanthone-C2-beta-D-glucoside), is a glucose functionalized xanthonoid found in abundance in mango fruit peel.

Figures 21A, 21B, 21C:
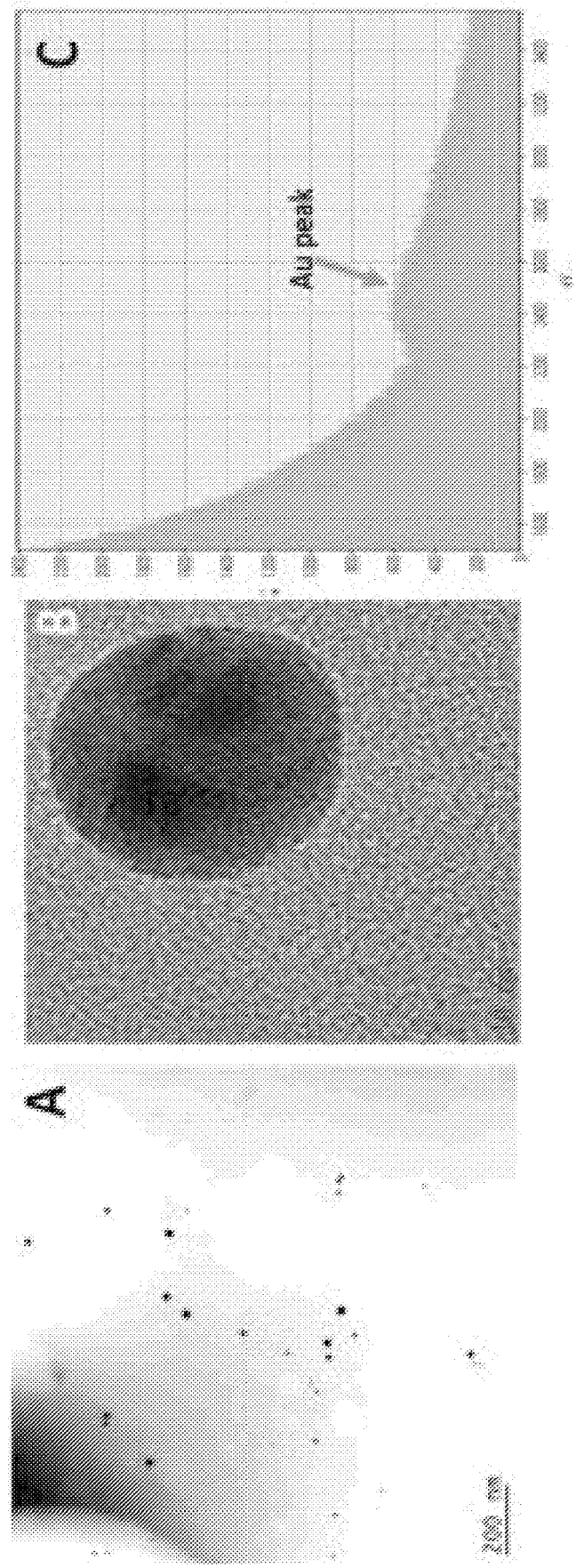
FIGS. 21A-21C are data including a TEM core size distribution image of MP-AuNPs A+B+C+D, a TEM image showing the lattice structure of MP-AuNPs, and a graph demonstrating presence of MP-AuNPs A+B+C+D by EELS (Electron Energy Loss Spectroscopy); this confirms the presence of gold metal in the overall drug formulation prepared from mixing; where: A=Gooseberry, B=Mango peel, C=curcumin, D=Gum Arabic.

FIGS. 21A-21C show data to characterize a MP-AuNPs-A+B+C+D Nano-Ayurvedic drug. The core size of MP-AuNPs, obtained by TEM, STEM and EELS (Electron Energy Loss Spectroscopy), indicates that the nanoparticles are spherical, mono-dispersed, and homogenous with a core size of 35±5 nm. For drug formulation, the following excipients were added into the MP-AuNPs 1×; (A) Gooseberry phytochemicals, (B) mango peel phytochemicals, (C) Curcumin extract, and (D) gum arabic.

Figures 22A, 22B:
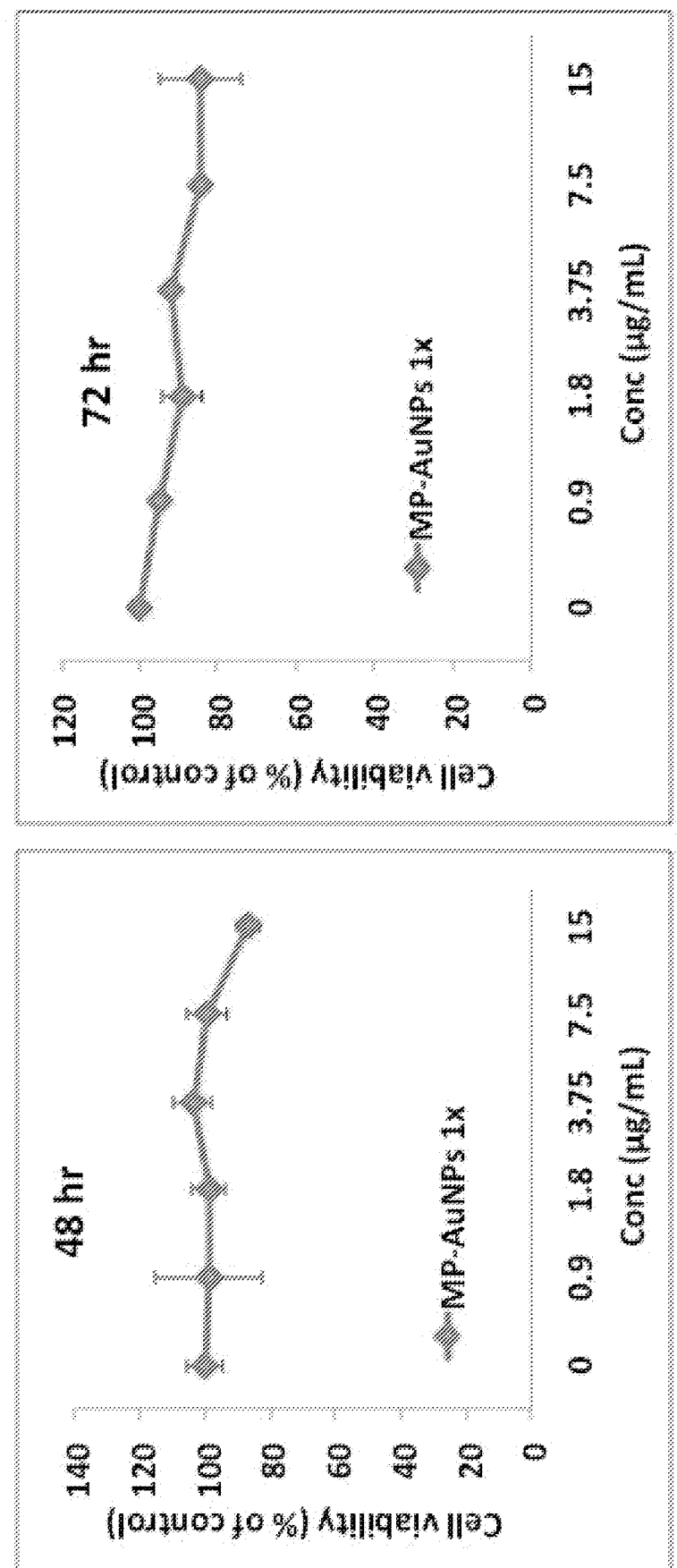
FIGS. 22A-22B are efficacy data of MP-AuNPs 1× on prostate cancer (PC-3) cell viability.
Figures 23A, 23B:
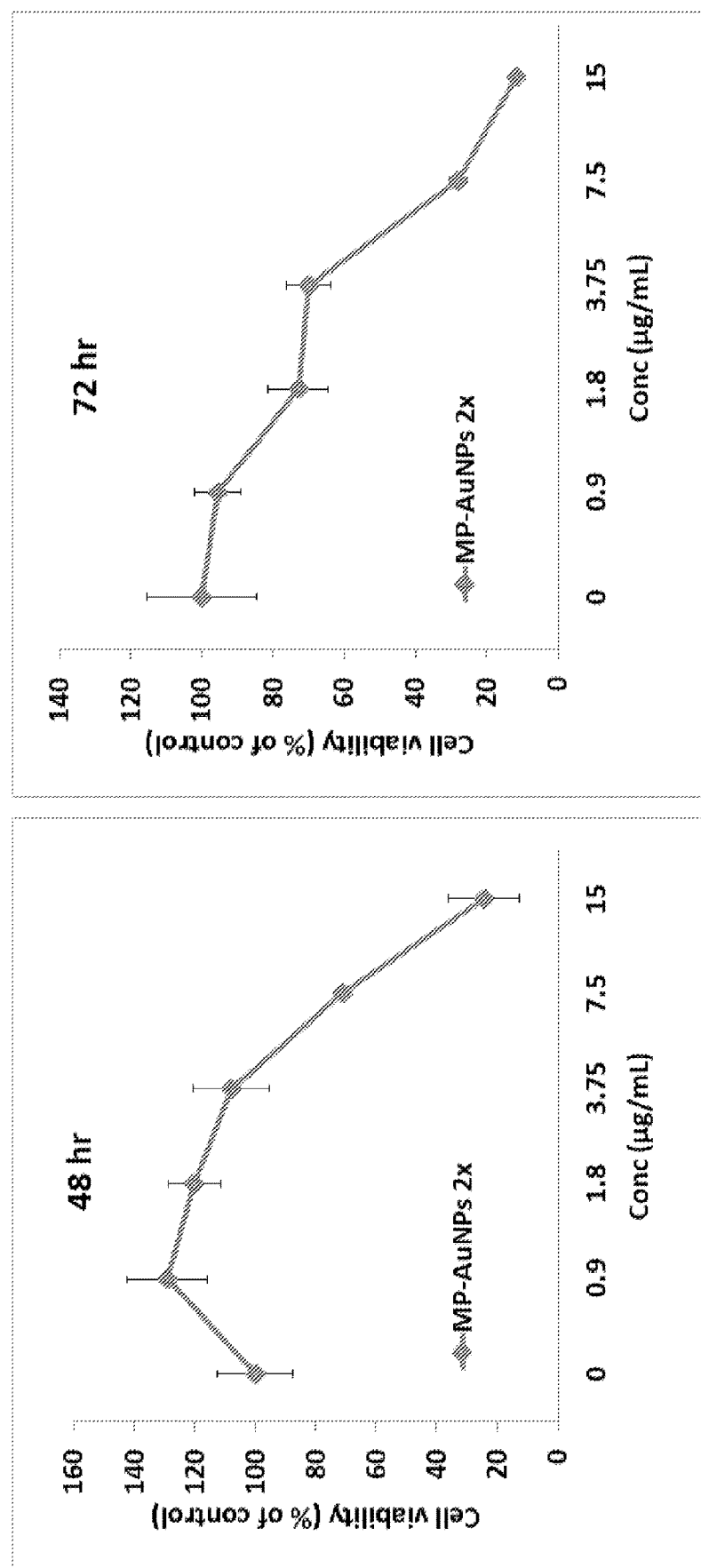
FIGS. 23A-23B are efficacy data of MP-AuNPs 2× on PC-3 cell viability.
Figures 24A, 24B:
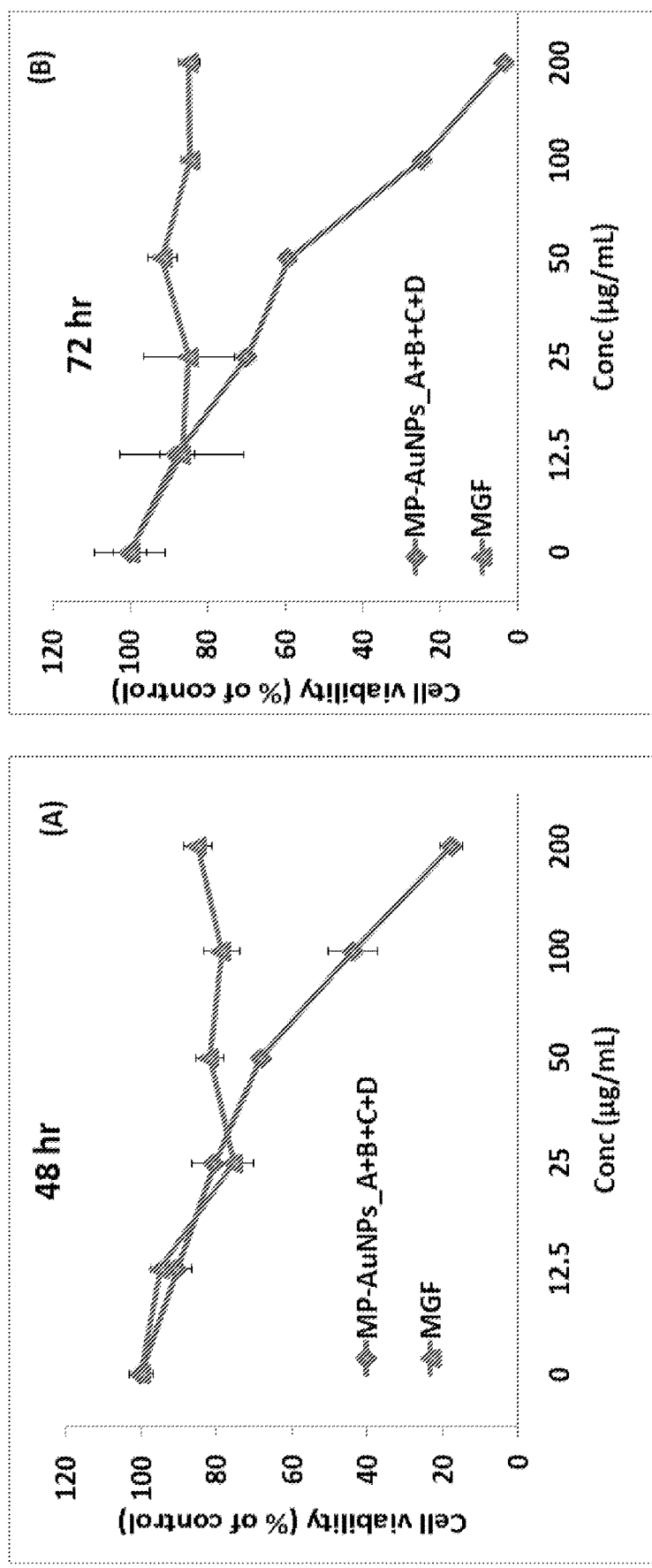
FIGS. 24A-24B are efficacy data of MP-AuNPs-A+B+C+D and free mangiferin (MGF) as a control on prostate cancer (PC-3) cells viability; where: A=Gooseberry, B=Mango peel, C=curcumin, D=Gum Arabic.
Figures 25A, 25B:
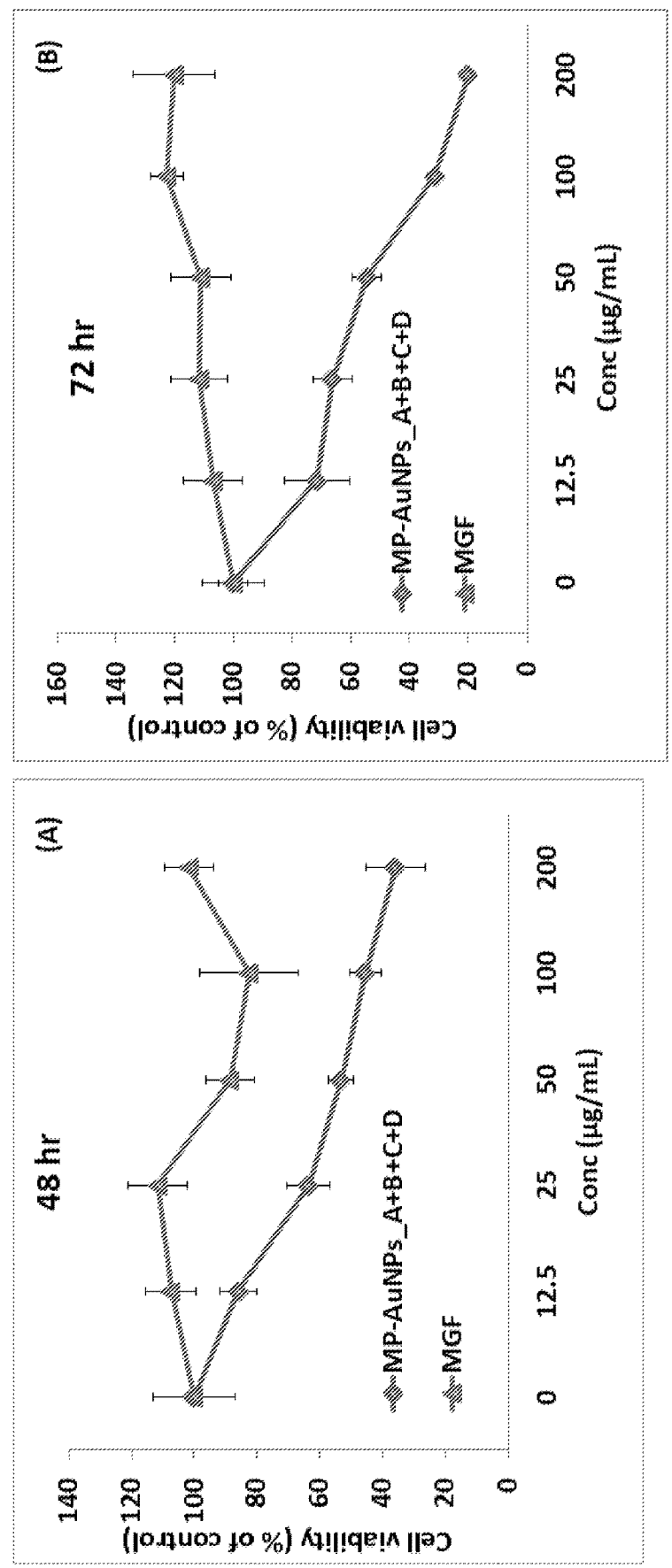
FIGS. 25A-25B are efficacy data of MP-AuNPs-A+B+C+D and free MGF as a control on prostate cancer (LNCaP) cell viability; where: A=Gooseberry, B=Mango peel, C=curcumin, D=Gum Arabic.
Figure 26B:
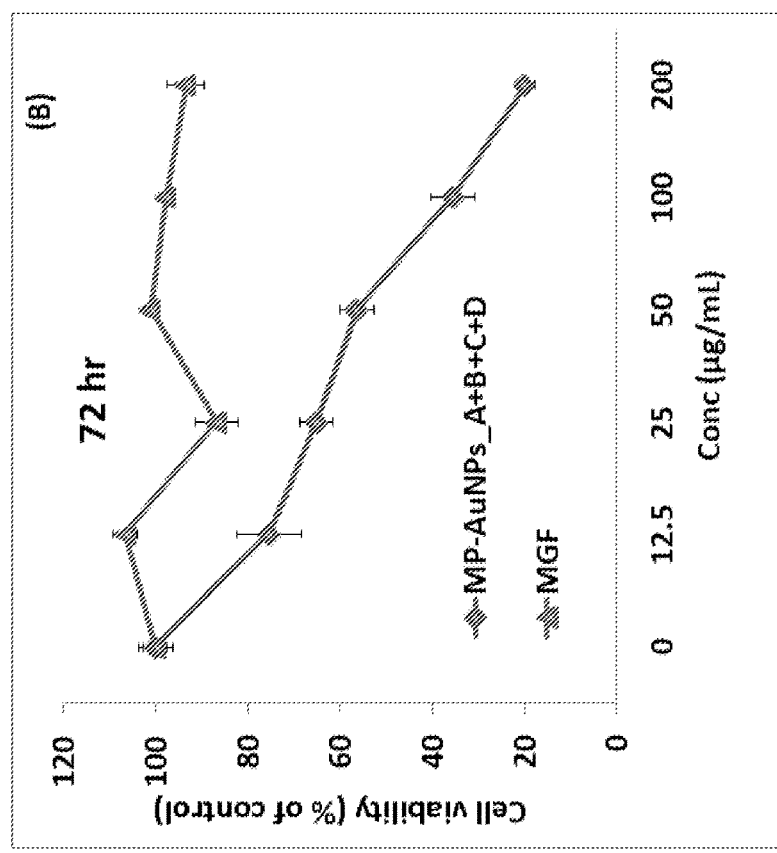
FIGS. 26A-26B are efficacy data of MP-AuNPs-A+B+C+D and free MGF as a control on dog prostate cancer (ACE-1) cell viability; where: A=Gooseberry, B=Mango peel, C=curcumin, D=Gum Arabic.
Figure 26A:
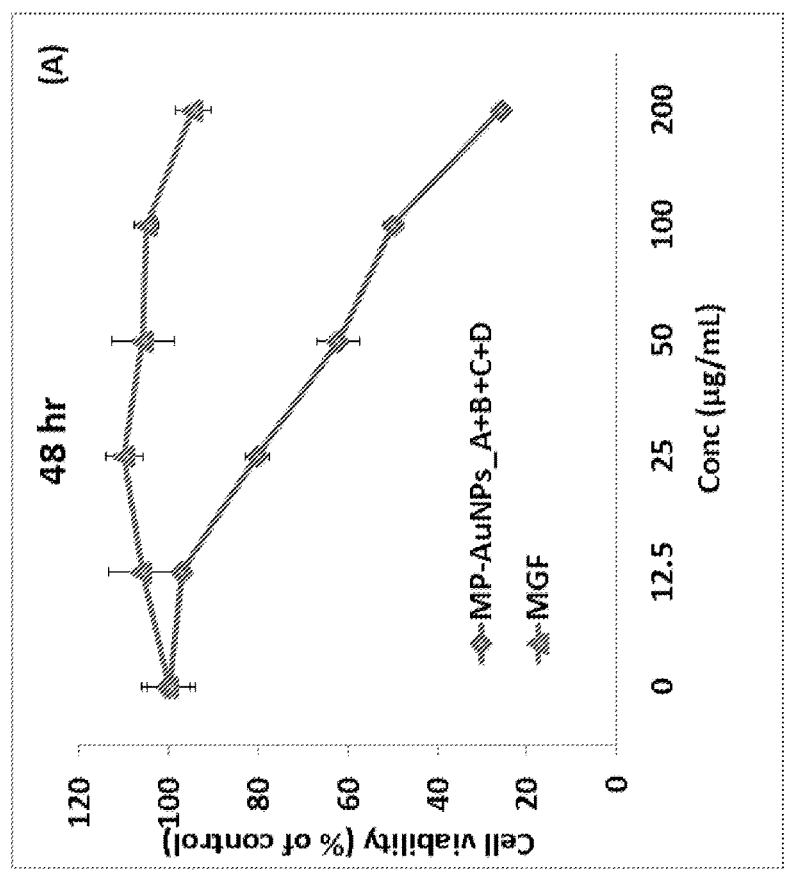
Figures 27A, 27B:
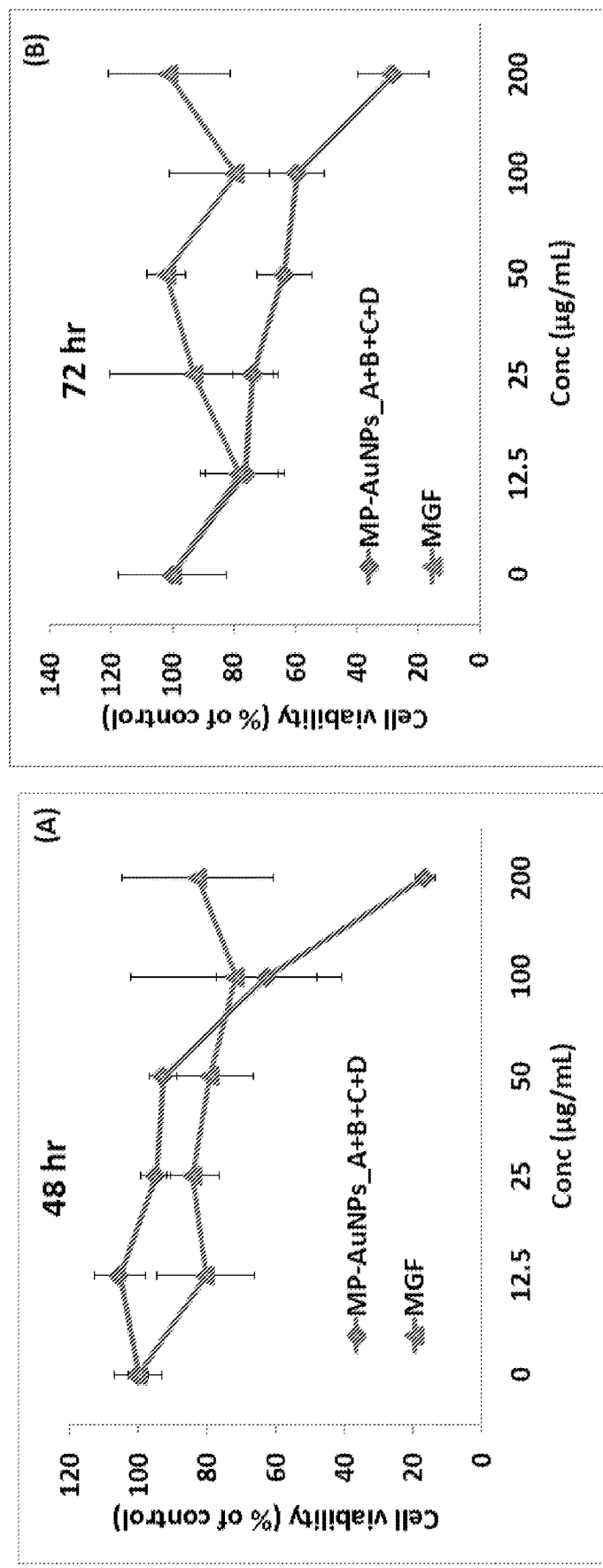
FIGS. 27A-27B are efficacy data of MP-AuNPs-A+B+C+D and free MGF as a control on breast cancer (MCF-7) cell viability; where: A=Gooseberry, B=Mango peel, C=curcumin, D=Gum Arabic.
Figures 28A, 28B:
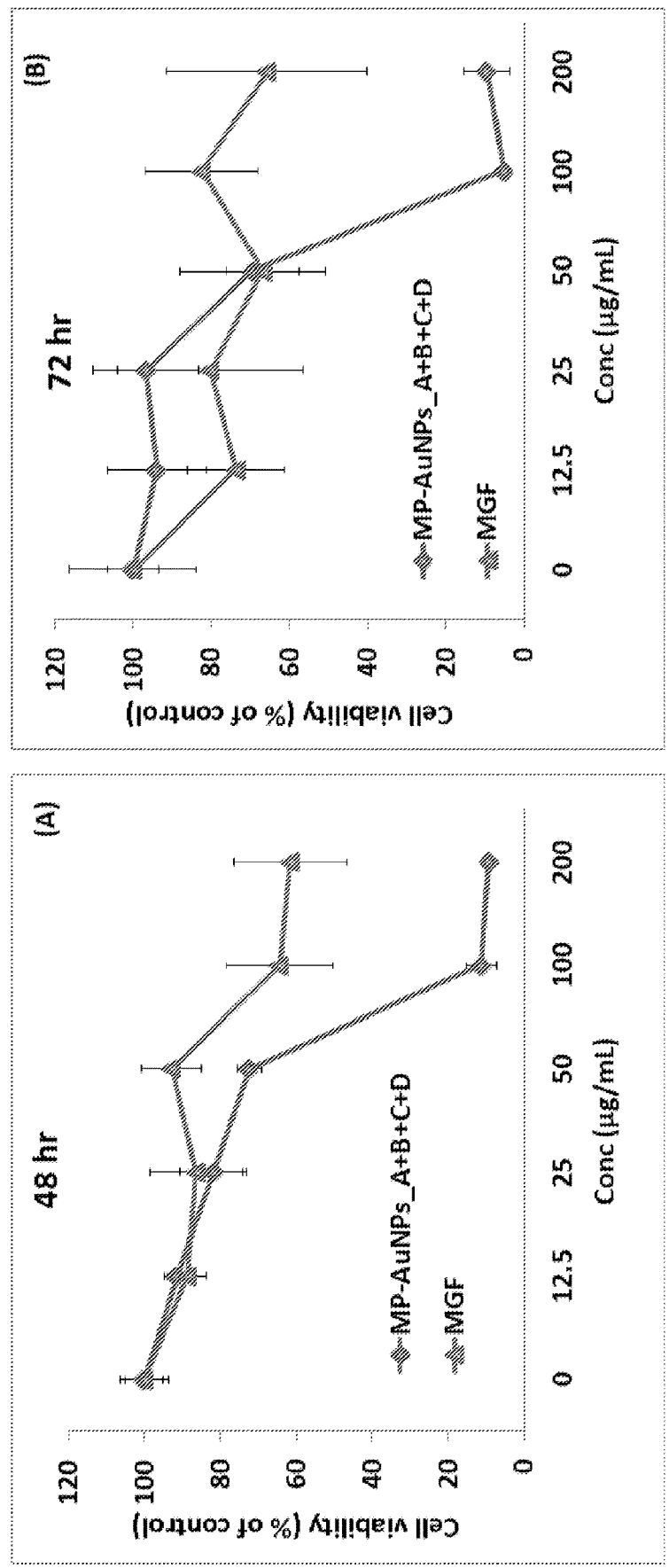
FIGS. 28A-28B are efficacy data of MP-AuNPs-A+B+C+D and free MGF as a control on breast cancer (MDA-MB-231) cell viability; where: A=Gooseberry, B=Mango peel, C=curcumin, D=Gum Arabic.
Figures 29A, 29B:
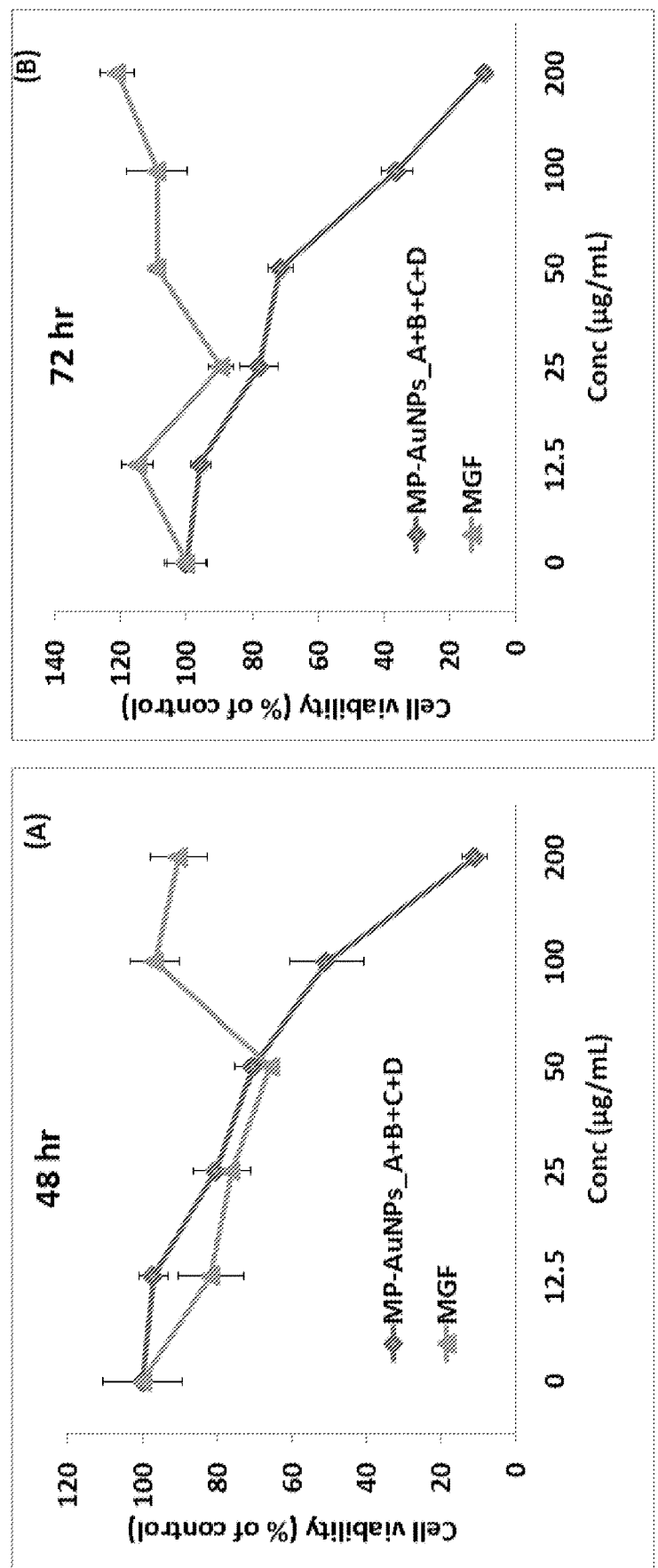
FIGS. 29A-29B are efficacy data of MP-AuNPs-A+B+C+D and free MGF as a control on pancreatic cancer (PANC-1) cell viability; where: A=Gooseberry, B=Mango peel, C=curcumin, D=Gum Arabic.
Figures 30A, 30B:
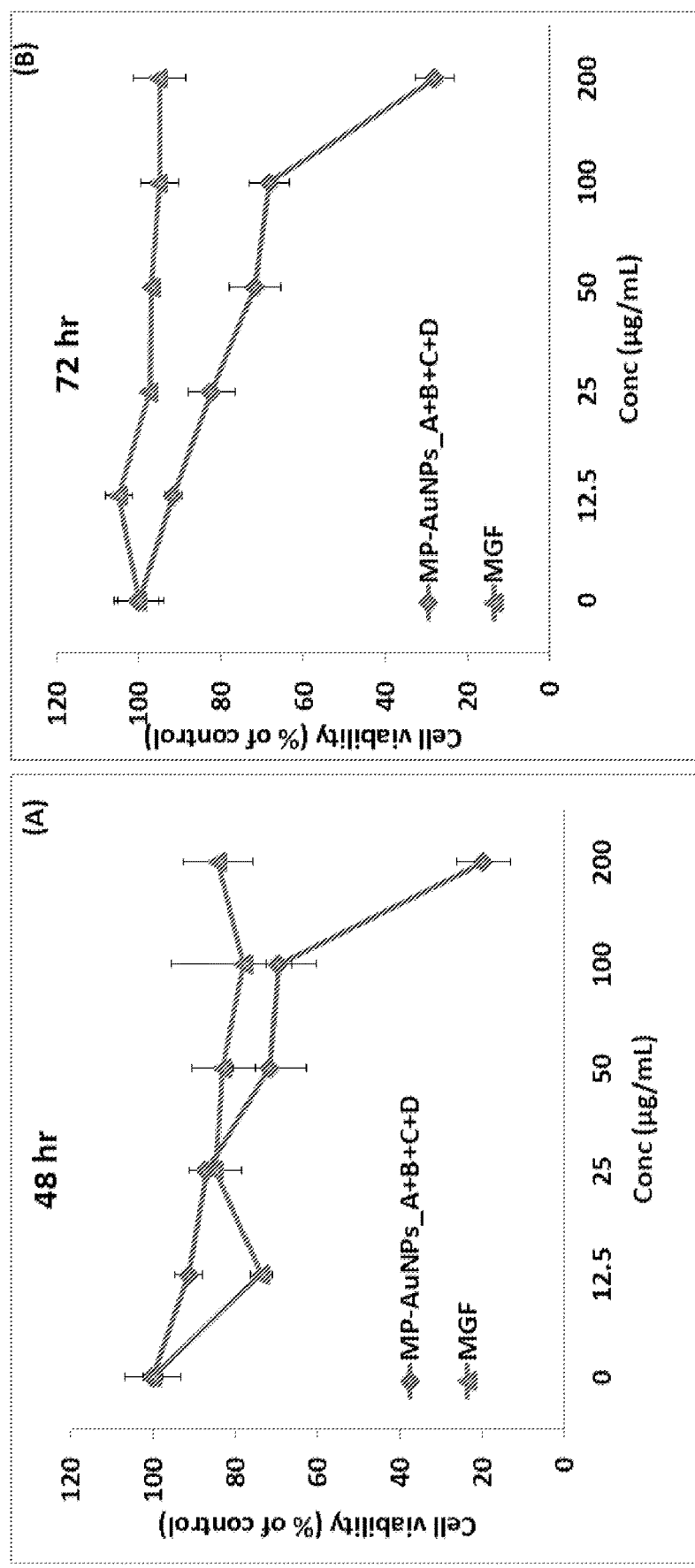
FIGS. 30A-30B are efficacy data of MP-AuNPs-A+B+C+D and free MGF as a control on pancreatic cancer (MIA-PACA-1) cell viability; where: A=Gooseberry, B=Mango peel, C=curcumin, D=Gum Arabic.
Figure 31B:
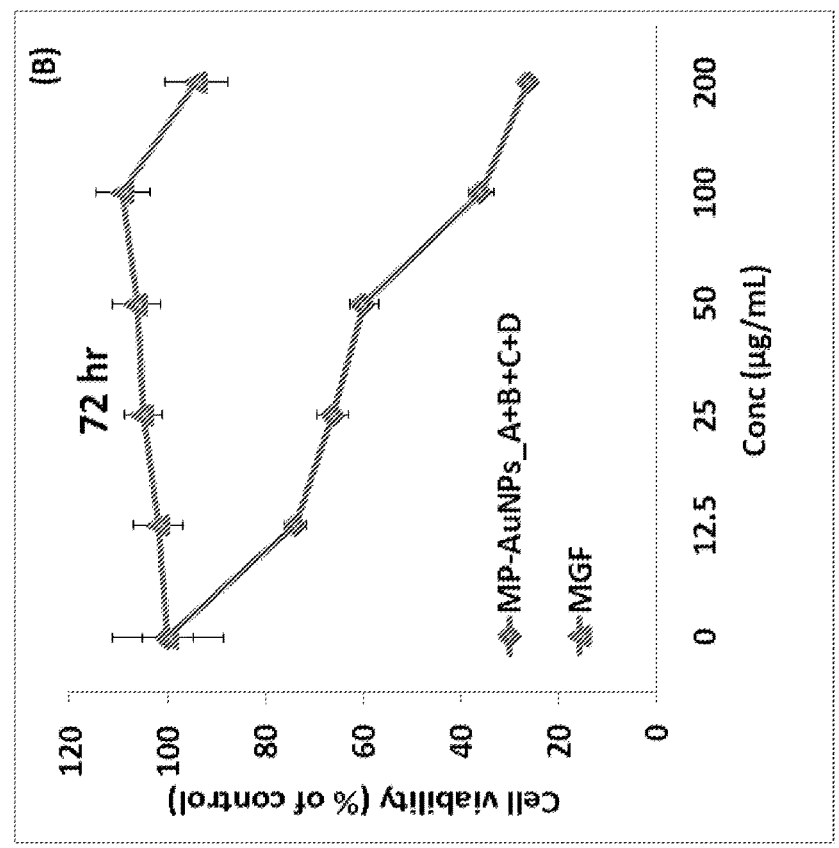
FIGS. 31A-31B are efficacy data of MP-AuNPs-A+B+C+D and free MGF as a control on colon cancer (SW-480) cell viability; where: A=Gooseberry, B=Mango peel, C=curcumin, D=Gum Arabic.
Figure 31A:
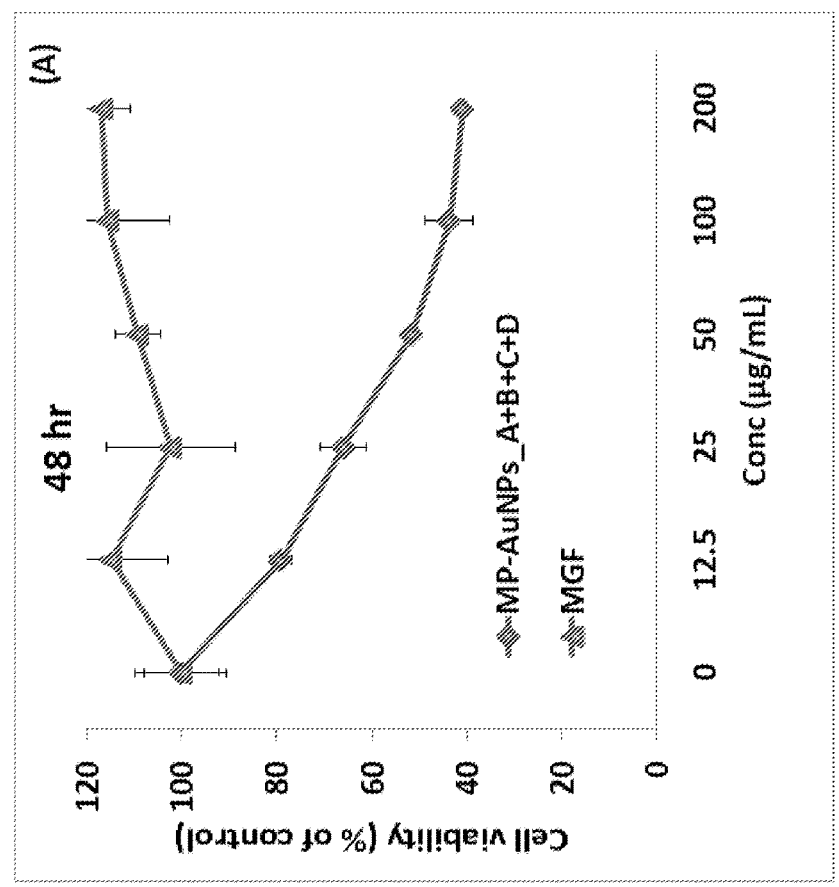
Figures 33A, 33B:
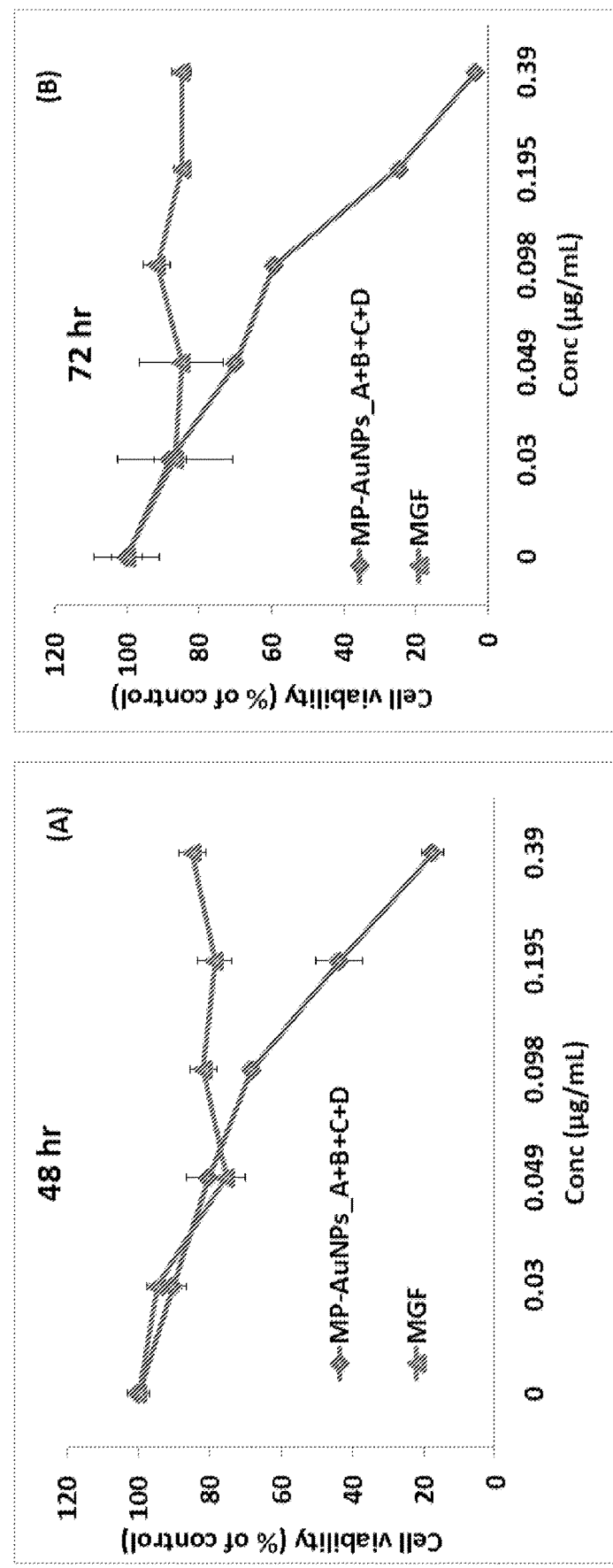
FIGS. 33A-33B are efficacy data of MP-AuNPs-A+B+C+D and free MGF as a control on prostate cancer (PC-3) cell viability; where: A=Gooseberry, B=Mango peel, C=curcumin, D=Gum Arabic.
Figure 34B:
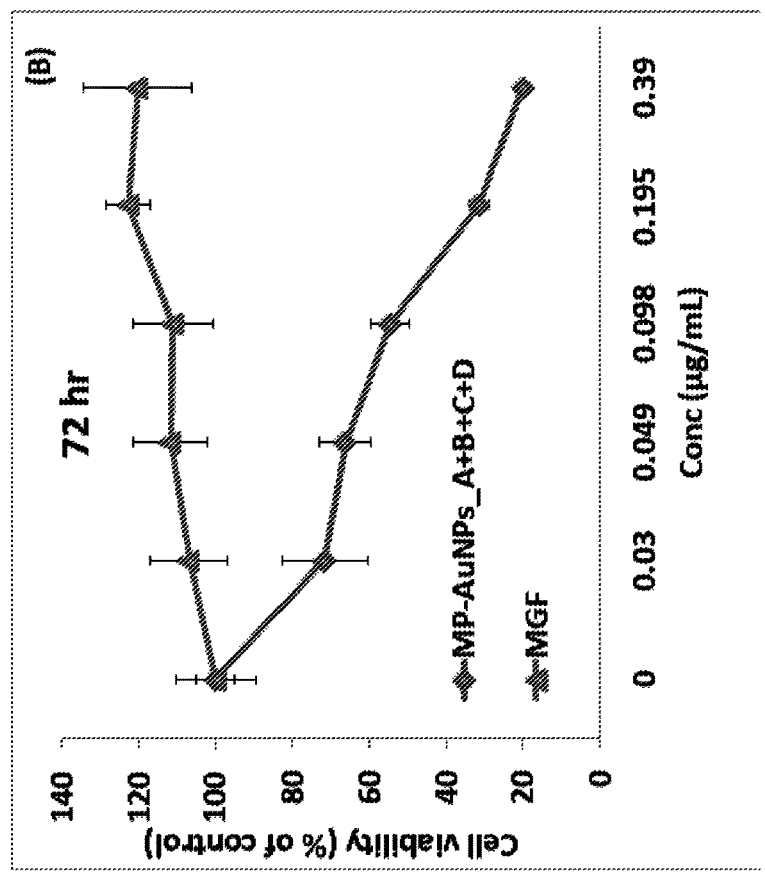
FIGS. 34A-34B are efficacy data of MP-AuNPs-G+B+C+D and free MGF as a control on prostate cancer (LNCaP) cell viability; where: A=Gooseberry, B=Mango peel, C=curcumin, D=Gum Arabic.
Figure 34A:
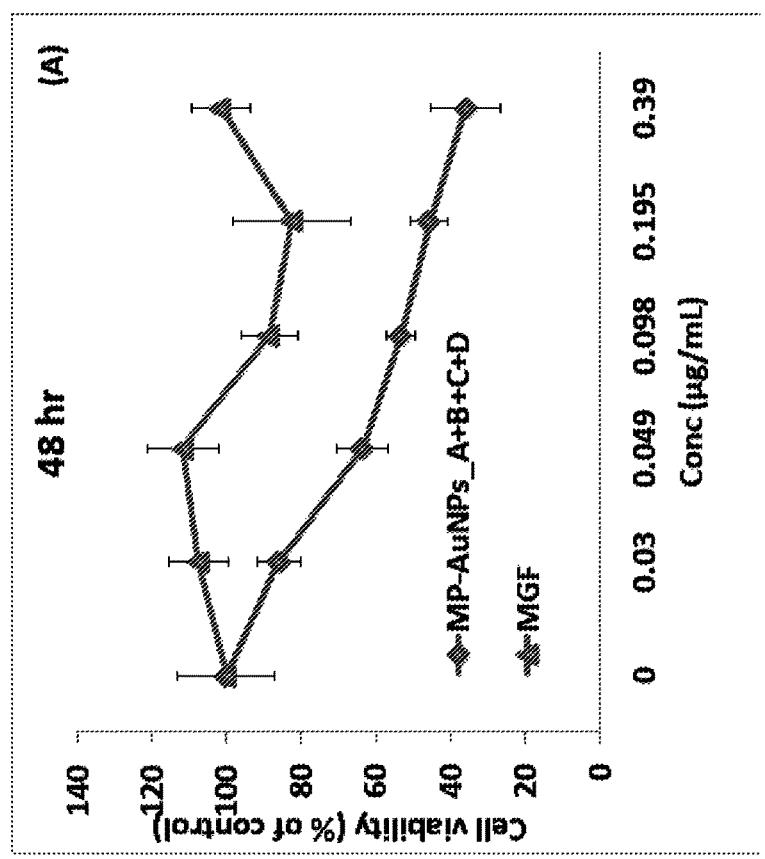
Figures 35A, 35B:
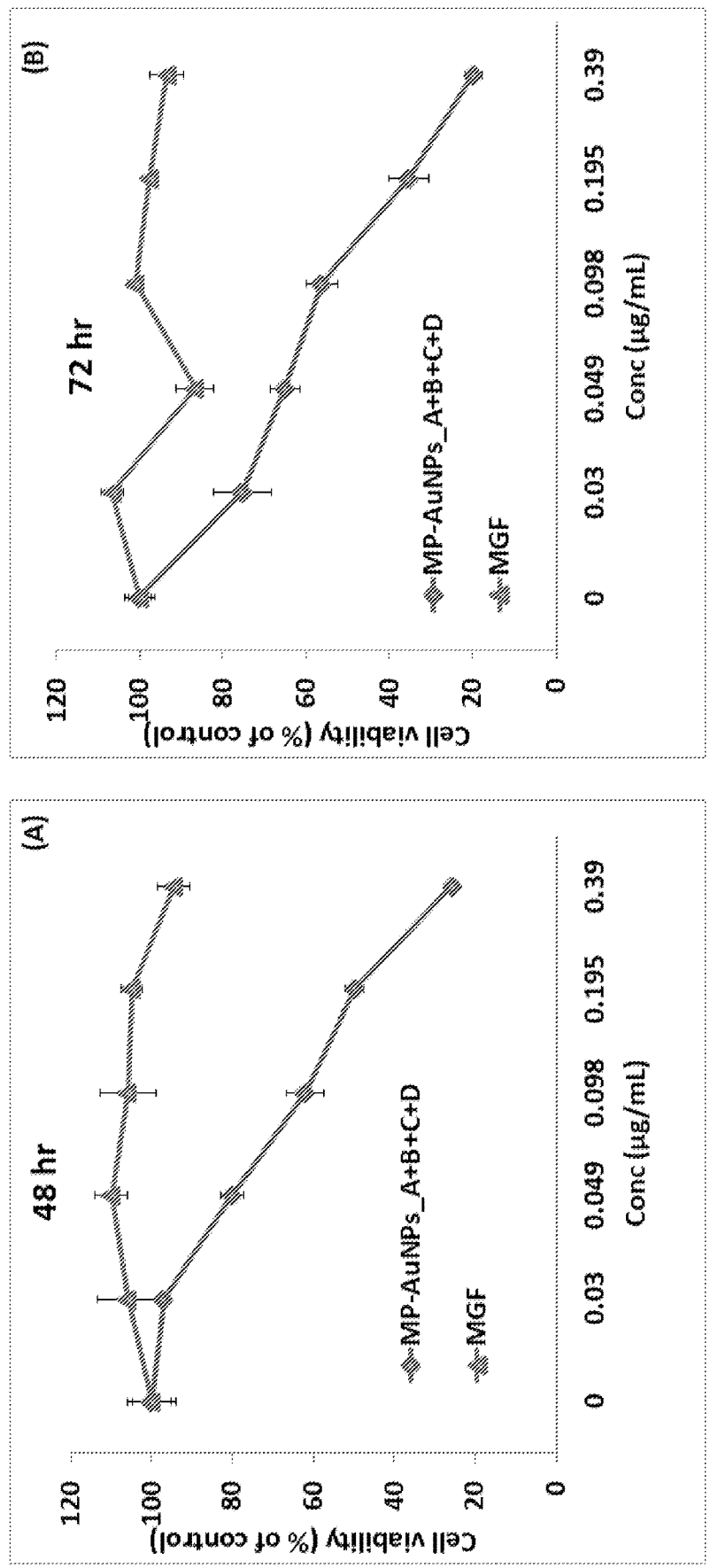
FIGS. 35A-35B are efficacy data of MP-AuNPs-G+B+C+D and free MGF as a control on dog prostate cancer (ACE-1) cell viability; where: A=Gooseberry, B=Mango peel, C=curcumin, D=Gum Arabic.
Figure 36B:
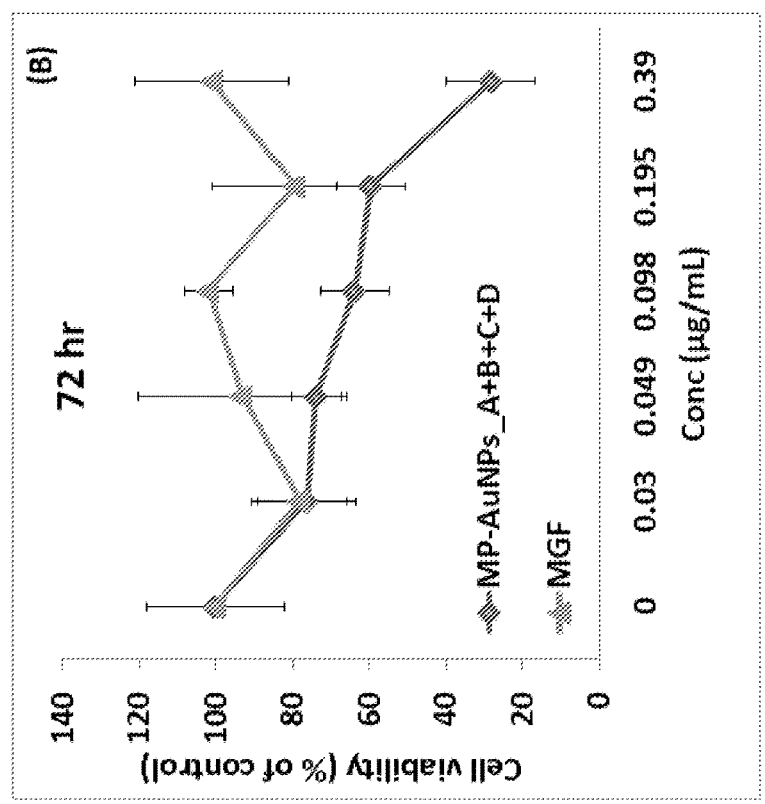
FIGS. 36A-36B are efficacy data of MP-AuNPs-G+B+C+D and free MGF as a control on breast cancer (MCF-7) cell viability; where: A=Gooseberry, B=Mango peel, C=curcumin, D=Gum Arabic.
Figure 36A:
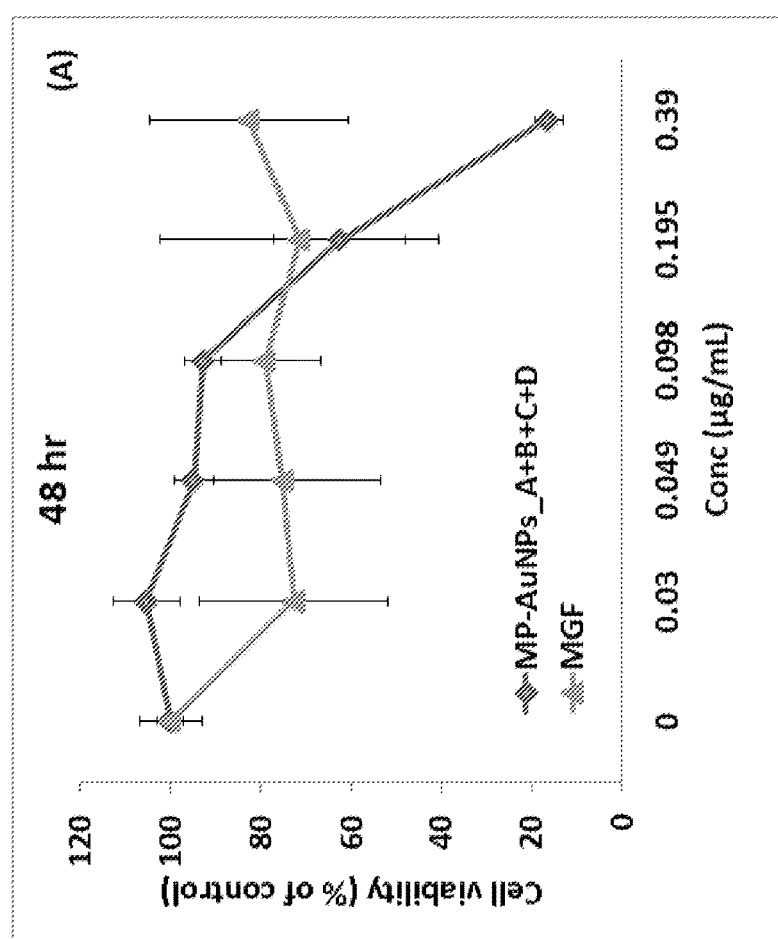
Figures 37A, 37B:
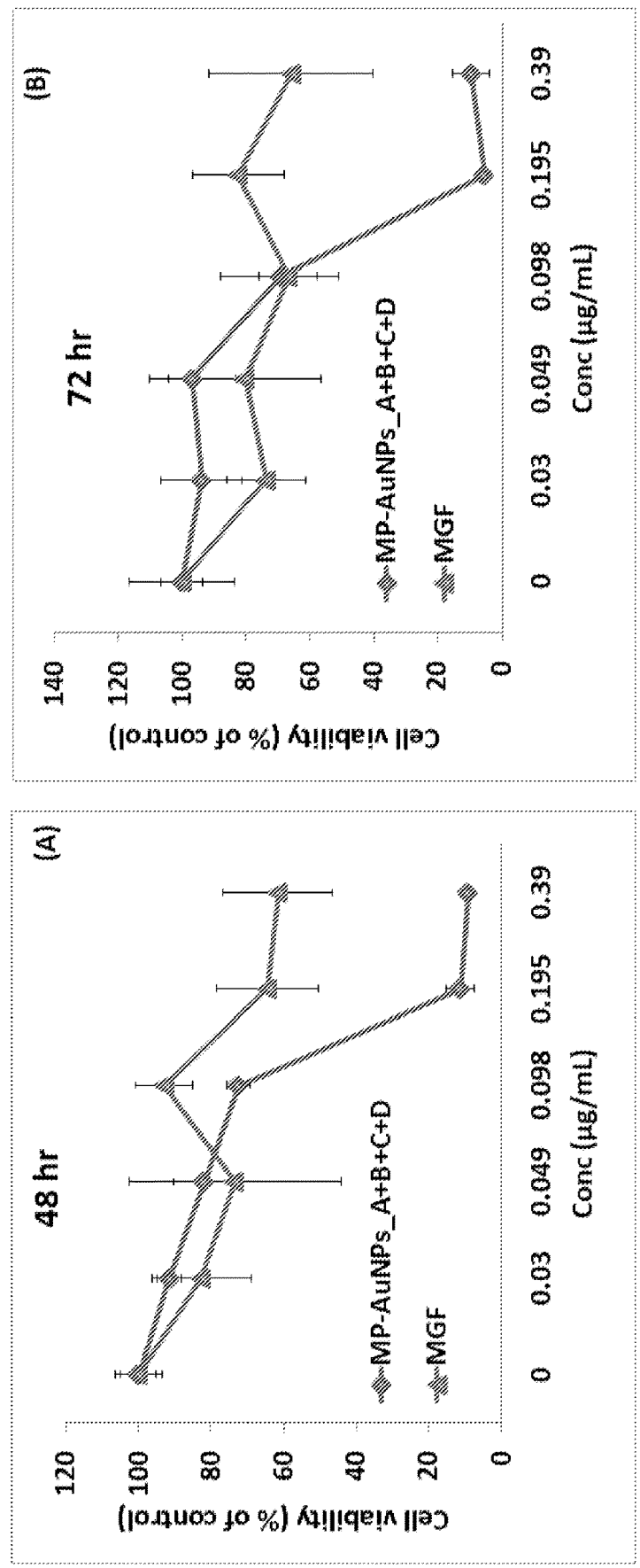
FIGS. 37A-37B are efficacy data of MP-AuNPs-A+B+C+D and free MGF as a control on breast cancer (MDA- MB-231) cell viability; where: A=Gooseberry, B=Mango peel, C=curcumin, D=Gum Arabic.
Figures 38A, 38B:
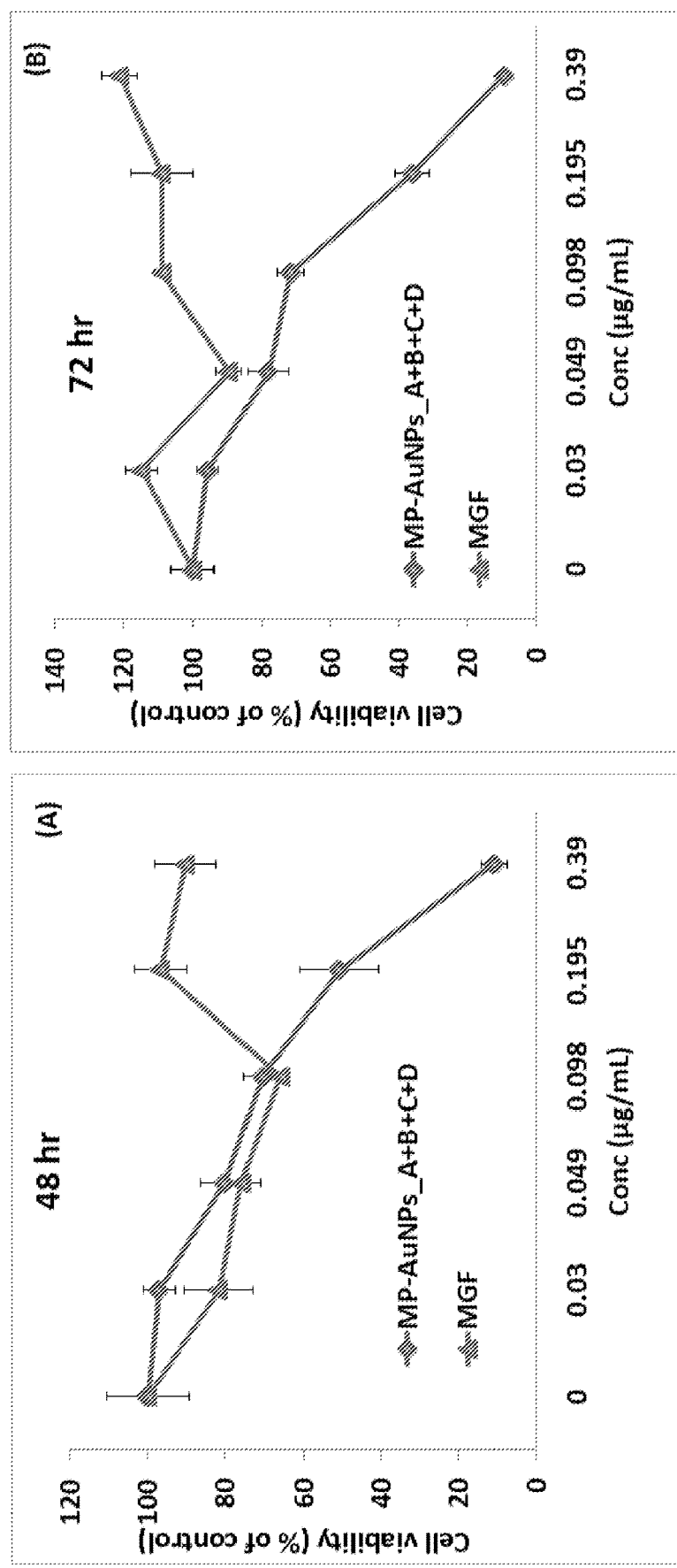
FIGS. 38A-38B are efficacy data of MP-AuNPs-G+B+C+D and free MGF as a control on pancreatic cancer (PANC-1) cell viability; where: A=Gooseberry, B=Mango peel, C=curcumin, D=Gum Arabic.
Figures 39A, 39B:
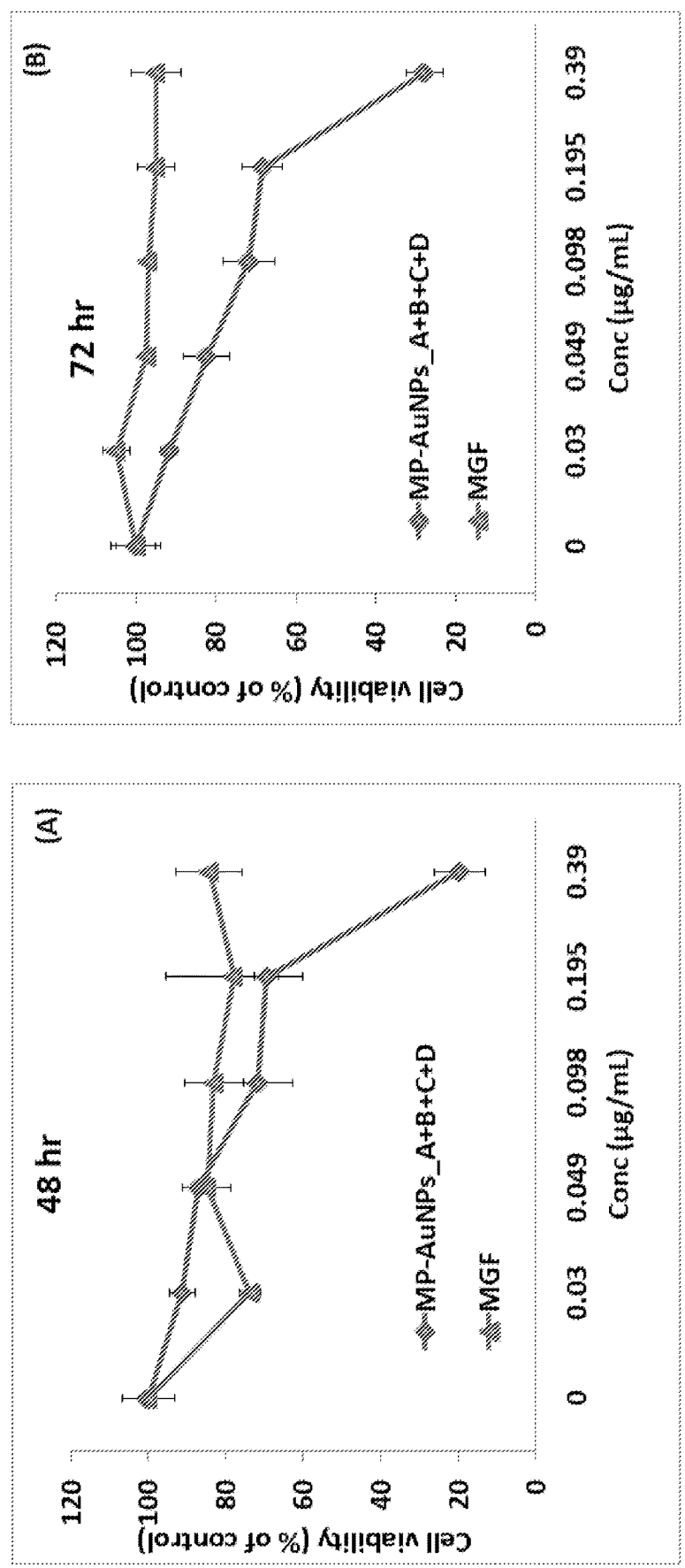
FIGS. 39A-39B are efficacy data of MP-AuNPs-G+B+C+D and free MGF as a control on pancreatic cancer (MIA-PACA-1) cell viability; where: A=Gooseberry, B=Mango peel, C=curcumin, D=Gum Arabic.
Figure 40A:
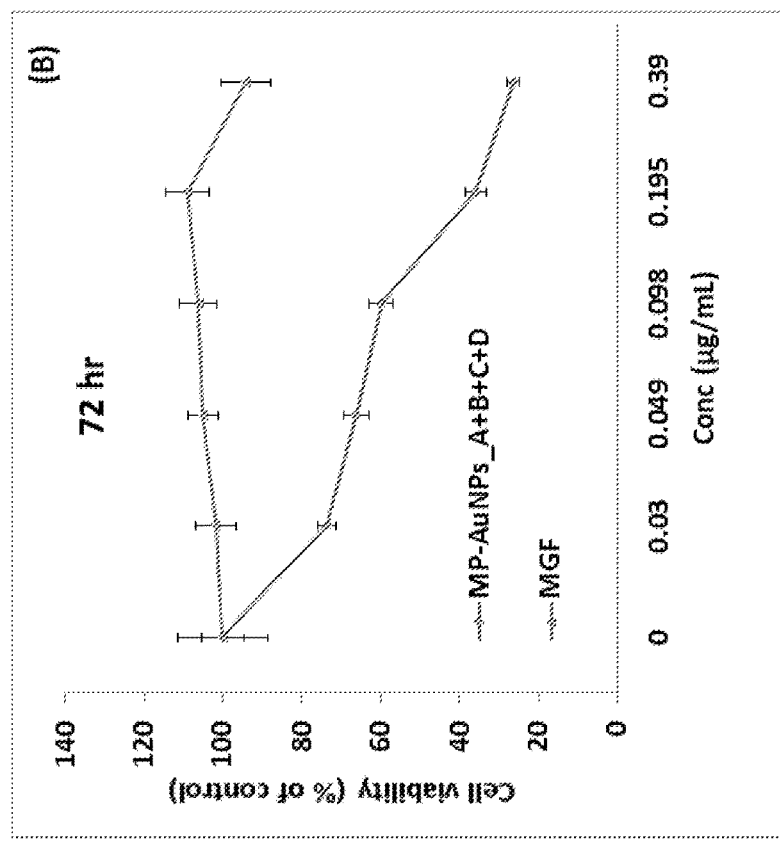
FIGS. 40A-40B are efficacy data of MP-AuNPs-G+B+C+D and free MGF as a control on colon cancer (SW-480) cell viability; where: A=Gooseberry, B=Mango peel, C=curcumin, D=Gum Arabic.
Figure 40B:
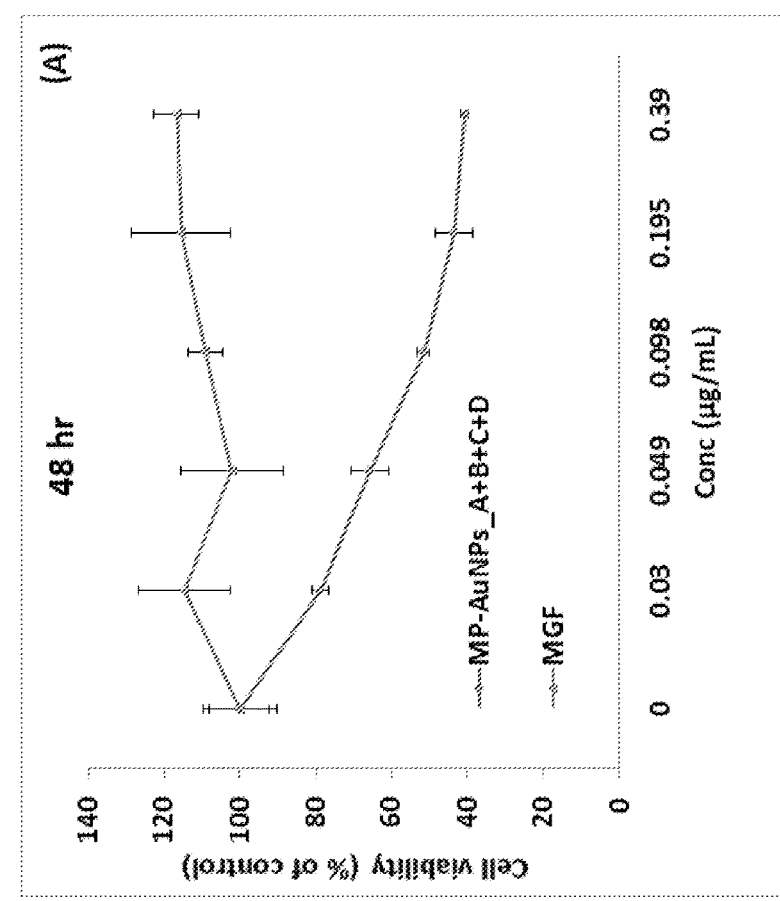
Figure 42A:
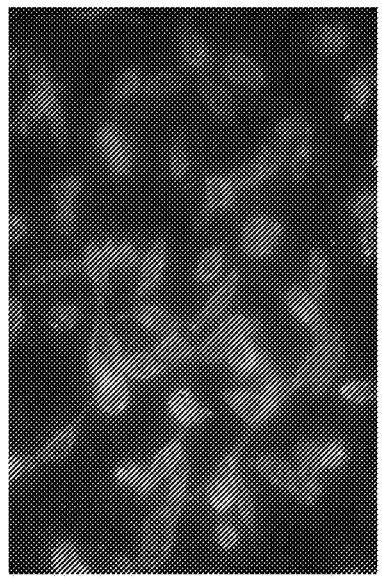
FIGS. 42A-42B are respectively images of untreated PC-3 cells and PC-3 cells treated with MP-AuNPs.
Figure 42B:
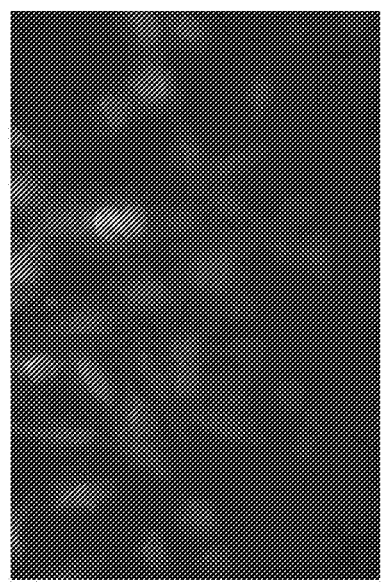
Figure 42C:
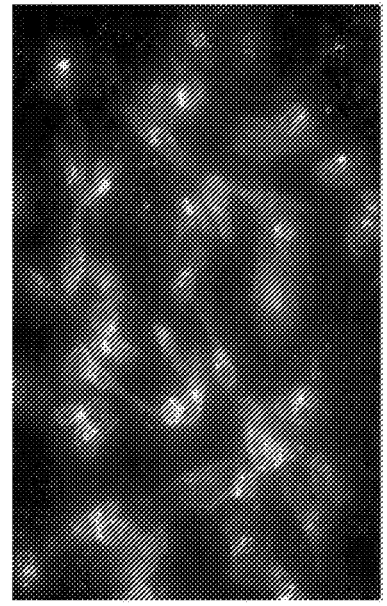
FIGS. 42C and 42D are respectively images of untreated MDA-MB-231 cells and MDA-MB-231 cells treated with MP-AuNPs.
Figure 42D:
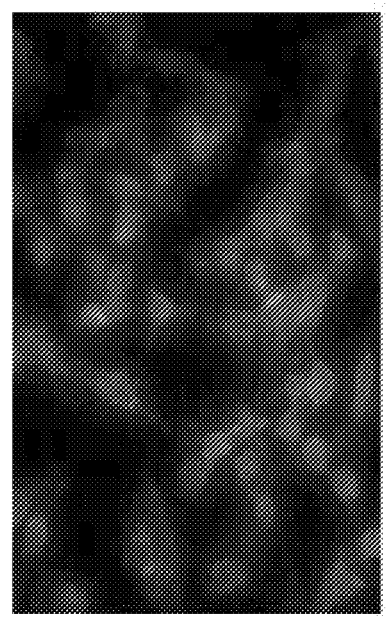

The cell viability profile of MP-AuNPs 1× and 2× was evaluated against prostate cancer (PC-3) and pancreatic cells (PANC-1) by MTT assay. The individual cells were treated with various dilutions of MP-AuNPs and free phytochemicals of mango peel (MP extract). Measurements of cell viability are presented in FIGS. 22A-23B. Cell viability profiles demonstrated that MP-AuNPs exhibited dose dependent efficacy in cell death of PC-3 cells. Among MP-AuNPs 1× and 2×.(single and double concentration of MP), 2× power used during the synthesis of MP-AuNP showed more effect on inhibition of prostate cancer cell viability, which is apparent by comparing the FIGS. 22A and 22B data to the data in FIGS. 23A and 23B. A MP-AuNPs-A+B+C+D Nano-Ayurvedic drug was tested with various cancer cells. To test in vitro antitumor efficacy of a MP-AuNPs-A+B+C+D Nano-Ayurvedic drug, a stock solution was prepared by mixing 4 mg of dry powder of drug material in 1 mL of DI water. The stock solution is a solution obtained by mixing 4 mg of dry powder of MP-AuNPs-A+B+C+D drug material in 1 mL of DI water. Drug material refers to mixtures of MP AuNP with A+B+C+D. The mixture was stirred overnight for 18 hours at room temperature to obtain the desired phytochemicals in DI water. The solution was centrifuged at 8000 rpm for 5 min at 30° C. to obtain the drug solution, and a pellet. To estimate the amount of released phytochemicals in the drug mixture, the pellet was further dried using a lyophilizer and the dry weight was measured to be 2 mg. The mass of released phytochemicals was 2 mg. The initial total amount of the drug used in the formulation was 4 mg. When this solution (with total 4 mg) was centrifuged, it produced a pellet weighing 2 mg. The supernatant liquid that remained behind should contain the reminder 2 mg. That is exactly what was obtained upon evaporation of water from the supernatant, and the dry weight of the mass left behind was found to be 2 mg. This demonstrates no drug was lost. The experiment as indicated confirms that 4 mg of drug mixture provides 2 mg.

To verify the amount of phytochemicals in the drug water extract, the water extract was dried using rotary evaporation. The weight of phytochemicals was measured to be 2 mg. This indicated that 4 mg of drug mixture provides 2 mg of phytochemicals.

Serial dilutions were prepared in RPMI/DMEM media to treat respective cells. The cell viability profile of MP-AuNPs-A+B+C+D Nano-Ayurvedic drug was evaluated against prostate cancer cells (PC-3, LNCap, ACE-1), breast cancer cells (MDA-MB-231 and MCF-7), pancreatic cancer cells (PANC-1 and MIA-PACA-1), colon cancer cells (SW-480) and normal endothelial cells (HAECs) by MTT assay (FIGS. 24-32). The cell viability profiles demonstrated that a MP-AuNPs-G+B+C+D Nano-Ayurvedic drug exhibited dose dependent efficacy in cell death of cancer cells. The results corroborated that a MP-AuNPs-A+B+C+D Nano-Ayurvedic drug showed minimal or no toxicity against a normal cell line (FIG. 32).

The cell viability profile of a MP-AuNPs-A+B+C+D Nano-Ayurvedic drug was evaluated against prostate cancer cells (PC-3, LNCap, ACE-1), breast cancer cells (MDA-MB-231 and MCF-7), pancreatic cancer cells (PANC-1 and MIA-PACA-1), colon cancer cell line (SW480) and normal endothelial cell line (HAECs) by MTT assay (FIGS. 33A-41B). The serial dilution doses were designed based on the amount of gold present in the MP-AuNPs-A+B+C+D. The amount of gold was analyzed by an AAS technique.

The cell viability profiles demonstrated that a MP-AuNPs-A+B+C+D Nano-Ayurvedic drug exhibited dose dependent efficacy in cell death of cancer cells.

PC-3 and MDA-MB-231 cells were incubated with MP-AuNPs. Dark field imaging was conducted and the results revealed that MP-AuNPs internalized into PC-3 and MDA-MB-231 cells within 4 hours of incubation time (FIGS. 42A-42D).

The data about simple (MP-AuNP) and complex (MP-AuNP-A+B+C+D) nanoparticles indicate much higher efficacy than free MGF. In addition the tests show that, for various cancer types including prostate, pancreatic, breast, lung, and colon, as well as in normal cells, the concentration ranges for gold content range from 0.03 micro gram/ml to 0.40 micro gram/ml. This translates to concentration range for the overall drug to 12.5 to 200 micro gram/ml.

For the preparation of simple and complex MP nanoparticles, mango (Mangifera indica) purchased from a local grocery shop were used in all the experiments. Mango peel was removed from mango and washed with doubly ionized water to remove any contaminants or dust particles and incubated at 50° C. (40-60° C.) for 4 hours and then ground to obtain dry powder. Powder was stored at room temperature and used for subsequent gold nanoparticle synthesis.

To synthesize MP-AuNP, dry mango peel powder of weight 30 mg was added to 6 ml of DI water in a 20 ml vial and stirred for 10 min at Room Temperature to create a homogenous suspension. Then, 100 µl of 0.1 M $NaAuCl_4$ solution was added, and the color of the solution turned ruby-red within 2 min, indicating the formation of gold nanoparticles. Generally, for 25-30 mg, peel powder 6-10 ml of DI water and stirring for 10-20 minutes, and 80-100 µl of 0.1 M $NaAuCl_4$ was used. The solution was filtered to remove the remaining insoluble mango peel powder. More generally, the nanoparticles can be stored at 5 to −20° C., which is a recommended for storage after production and prior to therapeutic use.

2× concentration MP-AuNPs were prepared by using twice the mass of mango peel powder (60 mg) dissolved into 6 mL of DI water. The reaction mixture was stirred on a magnetic stirrer at room temperature for 18 hours. 0.1 M NaAuCl4 (100 µL) was added to the reaction mixture. The mixture color changed from yellow to ruby red, indicating the formation of MP-AuNPs 2×.

The production of a MP-AuNPs-A+B+C+D Nano-Ayurvedic drug formulation was conducted as follows. MP-AuNPs 2× was prepared as discussed in the previous paragraph. For drug formulation, the following excipients were added into the 20 mL of MP-AuNPs 2×— (A) Gooseberry phytochemicals (2 gm), (B) Mango peel phytochemicals (4 gm), (C) Curcumin extract (1 gm), and (D) gum arabic (0.5 gm). All the excipients were added into the MP-AuNPs and mixed for 30 min at room temperature. The mixture was lyophilized to remove the excess water and to obtain a dry drug material. The yield was 6 gm. The sample was stored in an air-tight container at 4° C. More generally, suitable ranges for 20 mL of MP-AuNPs 2× include Gooseberry phytochemicals (2-2.5 gm), (B) Mango peel phytochemicals (4-5 gm), (C) Curcumin extract (1-1.5 gm), (D) gum arabic (0.5-1.0 gm). In the experiments, all the excipients were added into the MP-AuNPs and mixed for 30-45 min at room temperature. The mixture was lyophilized to remove the excess water and to obtain dry drug material, the yield was 6 gm. The sample was stored in tight container at 4-8° C., and used for further antitumor cell biology studies.

Figure 43:
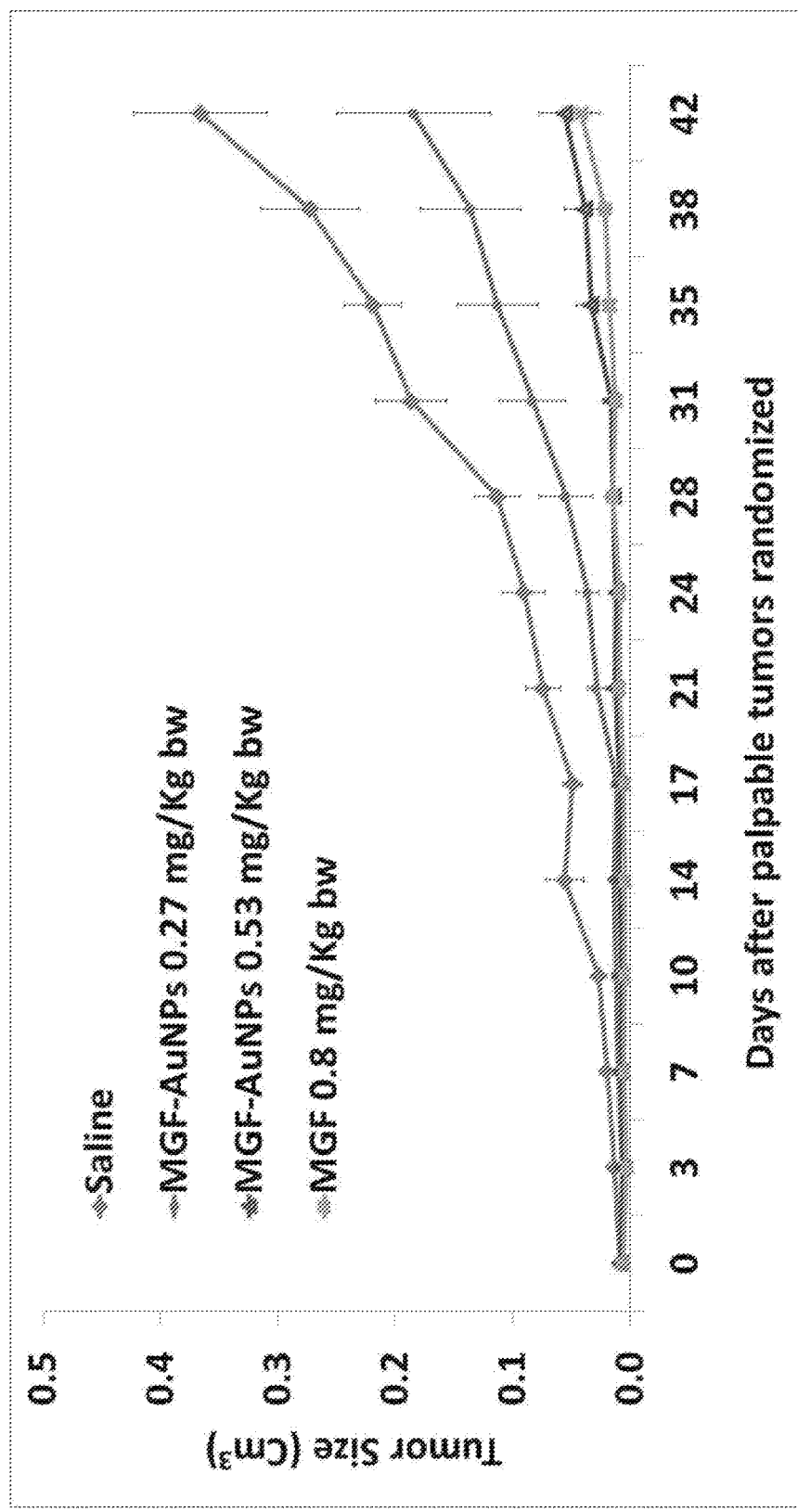
FIG. 43 illustrates the therapeutic effects of MGF (mangiferin) AuNPs when injected intraperitoneally in human prostrate tumor-bearing mice.

FIG. 43 is data showing therapeutic effects of MGF-AuNPs to control or reduce tumor size in human prostate tumor bearing SCID mice. Animals were randomized and treated intraperitoneally on day 0. Treatment was given intraperitoneally twice per week; n=5; mean±STE. Statistical comparison was made between different groups. For p=0.07 saline treated vs MGF-AuNPs 0.27 mg/kg bw, results were statistically not significant; For p=0.021 saline treated vs MGF-AuNPs 0.53 mg/kg bw, results were very statistically significant; For p=0.0009 saline treated vs MGF 0.8 mg/kg bw, results were extremely statistically significant.

Specific embodiments include drug preparations optimized for the production of capsules for human consumption. A preferred overall procedure for drug formulation MP-AuNPs-A+B+C+D is stated below. MP-AuNPs 2× was prepared as discussed in paragraph 102. For drug formulation, the following excipients were added into the 10 mL of MP-AuNPs 2×; (A) Gooseberry phytochemicals (5 gm), (B) Mango peel phytochemicals (10 gm), (C) Curcumin extract (1 gm), and (D) gum arabic (2.5 gm). All of the excipients were added into the MP-AuNPs 2× and mixed for 30 min at room temperature. The mixture was dried at 40° C. to remove excess water and to obtain dry drug material. The yield was 17 gm. The sample was stored in an air-tight container at 4° C. More generally, suitable ranges for mixture with 10 mL of MP-AuNPs 2× include (A) Gooseberry phytochemicals (5-6 gm), (B) Mango peel phytochemicals (10-12 gm), (C) Curcumin extract (1-1.5 gm), and (D) gum arabic (2.5-3.0 gm). In the experiments, excipients were added into the MP-AuNPs-2× and mixed for 30-45 min at room temperature. The mixture was dried at 40° C. to remove excess water and to obtain dry drug material, and the yield was 16-17 gm. The sample was stored in an air-tight container at 4-8° C., and used for further antitumor in vivo animal studies.

Figure 44:
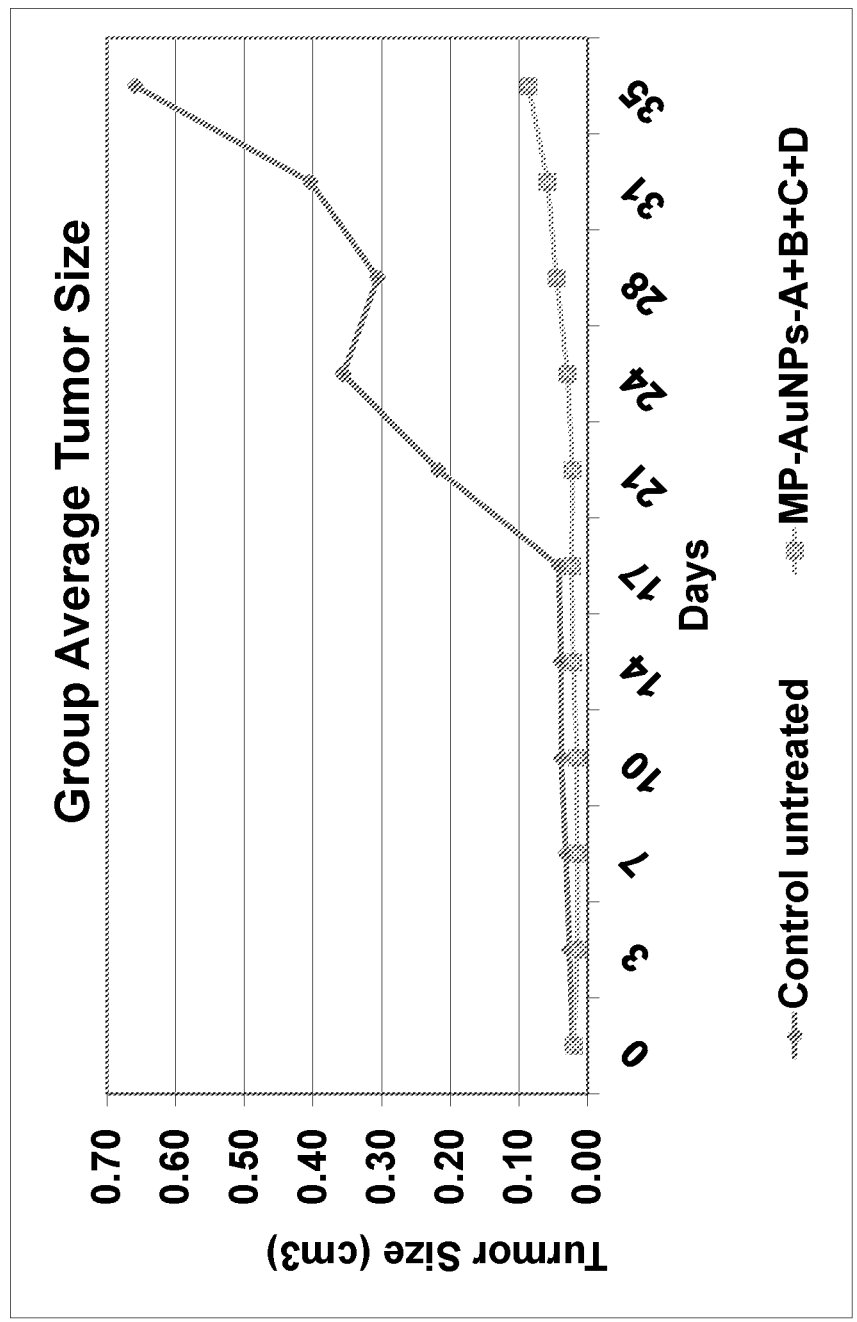
FIG. 44 is test data demonstrating the efficacy of MP-AuNPs A+B+C+D to control or reduce tumor size in human prostate tumor bearing SCID mice; where: A=Gooseberry, B=Mango peel, C=curcumin, D=Gum Arabic.

FIG. 44 is data showing the Therapeutic effects of MP-AuNPs-A+B+C+D to control or reduce tumor size in human prostate tumor bearing SCID mice. Animals were randomized and treated orally on day 0. Treatment was given twice per week; n=5, where MPD=MP-AuNPs-A+B+C+D drug.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A method for forming Ayurvedic encapsulated gold nanoparticles, the method comprising:
   mixing dried gooseberry
   or mango peel into a liquid medium to form a reducing agent solution including an extract of gooseberry phytochemicals or mango peel phytochemicals;
   mixing gold salts into the reducing agent solution;
   permitting reaction of the gold salts, in the absence of any other reducing agent, to form a nanoparticle solution of stabilized, biocompatible Ayurvedic encapsulated gold nanoparticles.

2. The method of claim 1, wherein the liquid medium consists of distilled (and/or de-ionized water) water, an alcoholic medium or a mixture of water and alcohol.

3. The method of claim 1, wherein the gold salts consist of non-radioactive $AuCl_4$.

4. The method of claim 1, wherein the concentration of gooseberry in the reducing agent solution is in the range of 1-3 or 100-200 mM.

5. The method of claim 4, wherein the concentration for gold salt weight is in the range of 4-8 mg, with 6-10 mg of gooseberry powder, in 6-10 ml distilled water.

6. The method of claim 5, wherein said permitting reaction is conducted at an agent solution temperature of 25° C.-28° C.

7. The method of claim 1, wherein the concentration of mango peel in the reducing agent solution is sufficient to ensure complete consumption of the gold salts.

8. The method of claim 1, further comprising removing non-reactants from the solution after said permitting reaction.

9. The method of claim 1, wherein said mixing mixes gooseberry and said mixing further comprises mixing gum Arabic into the liquid medium.

10. The method of claim 9, further comprising, after said permitting, adding (B) Mango peel phytochemicals, (C) Curcumin extract, (D) gum arabic.

11. The method of claim 1, wherein said mixing mixes mango peel product, and further comprising, after said permitting, adding (B) gooseberry phytochemicals, (C) Curcumin extract, (D) gum arabic.

12. A method of therapy, comprising intraperitoneally injecting, intravenously injecting, or orally administering the nanoparticle solution formed according to claim 1.

13. The method of claim 1, further comprising processing the nanoparticle solution of stabilized, biocompatible Ayurvedic encapsulated gold nanoparticles to form a dry powder or dry capsule Ayurvedic encapsulated gold nanoparticle drug.

14. A method of therapy, comprising orally administering the dry powder or dry capsule formed according to claim 13.

15. An Ayurvedic medicine consisting of a non-radioactive gold nanoparticle encapsulated with phytochemical existent in mango peel or gooseberry in a dry powder or capsule with curcumin extract and gum arabic.

* * * * *